(12) United States Patent
Liao et al.

(10) Patent No.: US 10,463,653 B2
(45) Date of Patent: *Nov. 5, 2019

(54) USE OF RING-FUSED BICYCLIC PYRIDYL DERIVATIVES AS FGFR4 INHIBITORS

(71) Applicant: NOVARTIS AG, Basel (CH)

(72) Inventors: Lv Liao, Shanghai (CN); Jing Xiong, Shanghai (CN)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/190,087

(22) Filed: Nov. 13, 2018

(65) Prior Publication Data

US 2019/0076412 A1 Mar. 14, 2019

Related U.S. Application Data

(63) Continuation of application No. 15/516,443, filed as application No. PCT/US2015/053677 on Oct. 2, 2015, now abandoned.

(30) Foreign Application Priority Data

Oct. 3, 2014 (CN) .................. PCT/CN2014/088094

(51) Int. Cl.
| | |
|---|---|
| *A61K 31/4375* | (2006.01) |
| *A61K 31/4545* | (2006.01) |
| *A61K 31/496* | (2006.01) |
| *A61P 35/00* | (2006.01) |
| *A61K 31/55* | (2006.01) |

(52) U.S. Cl.
CPC ...... *A61K 31/4375* (2013.01); *A61K 31/4545* (2013.01); *A61K 31/496* (2013.01); *A61K 31/55* (2013.01); *A61P 35/00* (2018.01)

(58) Field of Classification Search
CPC ............ A61K 31/4375; A61K 31/4545; A61K 31/496; A61K 31/55; A61P 35/00
USPC .................................................. 514/253.04
See application file for complete search history.

(56) References Cited

U.S. PATENT DOCUMENTS

| | | | |
|---|---|---|---|
| 5,866,586 A | 2/1999 | Forbes et al. | |
| 6,048,861 A | 4/2000 | Askew et al. | |
| 6,140,338 A | 10/2000 | Naya et al. | |
| 6,407,241 B1 | 6/2002 | Jensen et al. | |
| 7,098,332 B2 | 8/2006 | Liu et al. | |
| 7,115,750 B1 | 10/2006 | Kato et al. | |
| 7,368,444 B2 | 5/2008 | Seko et al. | |
| 8,293,746 B2 | 10/2012 | Bold et al. | |
| 8,481,531 B2 | 7/2013 | Saxty et al. | |
| 9,266,883 B2 * | 2/2016 | Buschnnann | A61K 31/444 |
| 9,533,988 B2 * | 1/2017 | Buschmann | A61K 31/444 |
| 9,802,917 B2 * | 10/2017 | Buschnnann | C07C 51/412 |
| 9,896,449 B2 | 2/2018 | Buschmann et al. | |
| 10,130,629 B2 * | 11/2018 | Buschnnann | A61K 31/4439 |
| 2004/0209902 A1 | 10/2004 | Lin et al. | |
| 2005/0101600 A1 | 5/2005 | Seko et al. | |
| 2005/0107399 A1 | 5/2005 | Boman et al. | |
| 2006/0004010 A1 | 1/2006 | Habashita et al. | |
| 2006/0178399 A1 | 8/2006 | Nishizawa et al. | |
| 2007/0015812 A1 | 1/2007 | Boehringer et al. | |
| 2008/0287445 A1 | 11/2008 | Coats et al. | |
| 2008/0312248 A1 | 12/2008 | Bold et al. | |
| 2009/0131403 A1 | 5/2009 | Kusuda et al. | |
| 2010/0086518 A1 | 4/2010 | Heise et al. | |
| 2010/0190782 A1 | 7/2010 | Baell et al. | |
| 2011/0150833 A1 | 6/2011 | Feng et al. | |
| 2011/0172217 A1 | 7/2011 | Fujioka et al. | |
| 2012/0028954 A1 | 2/2012 | Goff et al. | |
| 2012/0035171 A1 | 2/2012 | Saxty et al. | |
| 2012/0220600 A1 | 8/2012 | Aichholz et al. | |
| 2012/0252780 A1 | 10/2012 | Ng et al. | |
| 2014/0018358 A1 | 1/2014 | Shukla et al. | |
| 2014/0288053 A1 | 9/2014 | Berdini et al. | |
| 2014/0296233 A1 | 10/2014 | D'Agostino et al. | |
| 2014/0315902 A1 | 10/2014 | Sun et al. | |

(Continued)

FOREIGN PATENT DOCUMENTS

| | | |
|---|---|---|
| JP | 2012-180344 | 9/2012 |
| WO | WO 99/41239 | 8/1999 |

(Continued)

OTHER PUBLICATIONS

Berge et al Journal of Pharmaceutical Sciences, 1977, 66, 1-19 (Year: 1977).*

(Continued)

*Primary Examiner* — Yevgeny Valenrod

(74) *Attorney, Agent, or Firm* — Rimôn, P.C.

(57) ABSTRACT

The present invention relates to therapeutic uses of compounds of formula (1) or a pharmaceutically acceptable salt thereof.

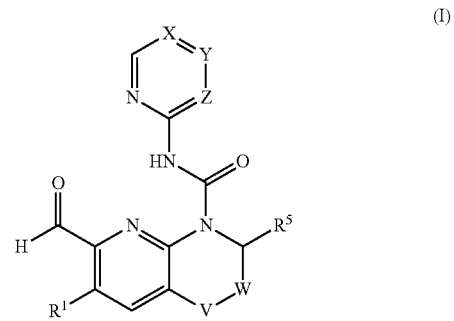

(I)

4 Claims, No Drawings

(56) References Cited

U.S. PATENT DOCUMENTS

| | | |
|---|---|---|
| 2015/0259358 A1 | 9/2015 | Pinto et al. |
| 2015/0274671 A1 | 10/2015 | Pinto et al. |
| 2015/0290235 A1 | 10/2015 | Gros et al. |
| 2016/0075666 A1 | 3/2016 | Angibaud et al. |
| 2016/0130237 A1 | 5/2016 | Reynolds et al. |
| 2016/0176825 A1 | 6/2016 | Gray et al. |
| 2016/0199371 A1 | 7/2016 | Futami et al. |
| 2017/0174652 A1 | 6/2017 | Bifulco et al. |
| 2017/0182123 A1 | 6/2017 | Ling et al. |
| 2018/0185341 A1* | 7/2018 | Buschmann ....... A61K 31/4545 |

FOREIGN PATENT DOCUMENTS

| | | |
|---|---|---|
| WO | WO 2004/078163 | 9/2004 |
| WO | WO 2007/146230 | 12/2007 |
| WO | WO 2010/129467 | 11/2010 |
| WO | WO 2011/093501 | 8/2011 |
| WO | WO 2011/111880 | 9/2011 |
| WO | WO 2014/011900 | 1/2014 |
| WO | WO 2018/083603 | 5/2018 |

OTHER PUBLICATIONS

French et al., "Targeting FGFR4 Inhibits Hepatocellular Carcinoma in Preclinical Mouse Models". PLoS One. 2012; 7(5): e36713. Epub May 15, 2012.

Hubbard et al., "Evidence for a common mechanism of SIRT1 regulation by allosteric activators", Science. Mar. 8, 2013; 339(6124): 1216-1219.

Mellor, "Targeted inhibition of the FGF19-FGFR4 pathway in hepatocellular carcinoma; translational safety considerations", Liver Int. Jul. 2014; 34(6): e1-9. Epub Jan. 24, 2014.

Zhou et al., "A Structure-Guided Approach to Creating Covalent FGFR Inhibitors", Chem Biol., Mar. 26, 2010; pp. 285-295.

Zhao et al., "FGF19 promotes epithelial-mesenchymal transition in hepatocellular carcinoma cells by modulating the GSK3β/β-catenin signaling cascade via FGFR4 activation", Oncotarget, Mar. 22, 2016, 7(12): 13575-13586, Epub Oct. 20, 2015.

Repana et al., "Targeting FGF19/FGFR4 Pathway: A Novel Therapeutic Strategy for Hepatocellular Carcinoma", Diseases, Oct. 28, 2015; pp. 294-305.

* cited by examiner

USE OF RING-FUSED BICYCLIC PYRIDYL DERIVATIVES AS FGFR4 INHIBITORS

CROSS-REFERENCE TO RELATED APPLICATIONS

This application is a continuation of U.S. application Ser. No. 15/516,443, filed on Apr. 3, 2017, which is a 35 U.S.C. § 371 of International Patent Application No. PCT/US2015/053677, filed on Oct. 2, 2015, which claims the benefit of International Patent Application No. PCT/CN2014/088094, filed on Oct. 3, 2014. The contents of all of which are incorporated by reference herein in their entireties.

FIELD OF THE INVENTION

The invention provides the use of bicyclic pyridyl derivatives compounds in methods of treating disease.

BACKGROUND OF THE INVENTION

Normal growth, as well as tissue repair and remodeling, require specific and delicate control of activating growth factors and their receptors. Fibroblast Growth Factors (FGFs) constitute a family of over twenty structurally related polypeptides that are developmentally regulated and expressed in a wide variety of tissues. FGFs stimulate proliferation, cell migration and differentiation and play a major role in skeletal and limb development, wound healing, tissue repair, hematopoiesis, angiogenesis, and tumorigenesis (reviewed in Ornitz, Novartis Found Symp 232: 63-76; discussion 76-80, 272-82 (2001)).

The biological action of FGFs is mediated by specific cell surface receptors belonging to the Receptor Protein Tyrosine Kinase (RPTK) family of protein kinases. These proteins consist of an extracellular ligand binding domain, a single transmembrane domain and an intracellular tyrosine kinase domain which undergoes phosphorylation upon binding of FGF. Four FGFRs have been identified to date: FGFR1 (also called Fig, fms-like gene, fit-2, bFGFR, N-bFGFR or Cek1), FGFR2 (also called Bek-Bacterial Expressed Kinase-, KGFR, Ksam, Ksaml and Cek3), FGFR3 (also called Cek2) and FGFR4. All mature FGFRs share a common structure consisting of an amino terminal signal peptide, three extracellular immunoglobulin-like domains (Ig domain I, Ig domain II, Ig domain Ill), with an acidic region between Ig domains (the "acidic box" domain), a transmembrane domain, and intracellular kinase domains (Ullrich and Schlessinger, Cell 61: 203, 1990; Johnson and Williams (1992) Adv. Cancer Res. 60: 1-41). The distinct FGFR isoforms have different binding affinities for the different FGF ligands.

Alterations in FGFRs have been associated with a number of human cancers including myeloma, breast, stomach, colon, bladder, pancreatic and hepatocellular carcinomas. Recently, it was reported that FGFR4 may play an important role in liver cancer in particular (PLoS One, 2012, volume 7, 36713). Other studies have also implicated FGFR4 or its ligand FGF19 in other cancer types including breast, glioblastoma, prostate, rhabdomyosarcoma, gastric, ovarian, lung, colon (Int. J. Cancer 1993; 54:378-382; Oncogene 2010; 29:1543-1552; Cancer Res 2010; 70:802-812; Cancer Res 2011; 71:4550-4561; Clin Cancer Res 2004; 10:6169-6178; Cancer Res 2013; 73:2551-2562; Clin Cancer Res 2012; 18:3780-3790; J. Clin. Invest. 2009; 119:3395-3407; Ann Surg Oncol 2010; 17:3354-61; Cancer 2011; 117:5304-13; Clin Cancer Res 2013; 19:809-820; PNAS 2013; 110: 12426-12431; Oncogene 2008; 27:85-97).

Therapies involving FGFR4 blocking antibodies have been described for instance in WO2009/009173, WO2007/136893, WO2012/138975, WO2010/026291, WO2008/052798 and WO2010/004204. WO2014/144737 and WO2014/011900 also describe low molecular weight FGFR4 inhibitors.

Given the numerous therapies available to an individual having a particular disease, a determination of the factors that influence, for example, response to a particular drug, could be used to provide a patient with a personalized treatment regime. Such personalized treatment regimens offer the potential to maximize therapeutic benefit to the patient while minimizing related side effects that can be associated with alternative and less effective treatment regimens.

SUMMARY OF THE INVENTION

The present invention aims to address the need for more adapted and effective treatment regimens using FGFR4 inhibitors. The invention provides compounds, pharmaceutically acceptable salts thereof, pharmaceutical compositions thereof, which compounds are FGFR4 inhibitors, for use in methods of treating, preventing, or ameliorating cancers.

In particular, the invention relates to methods of treating, preventing or ameliorating solid malignancies in a patient, wherein the solid malignancies are characterized by positive expression of certain biomarkers.

Various embodiments of the invention are described herein.

Within certain aspects, provided herein is a compound of formula (I) or a pharmaceutically acceptable salt thereof:

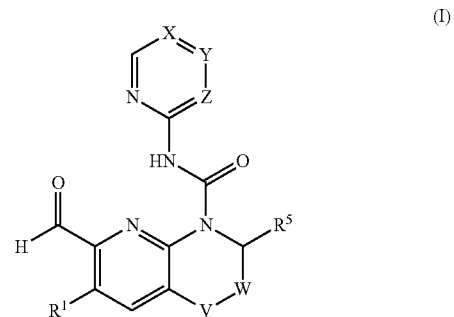

(I)

for use in the treatment of solid malignancies characterized by positive FGFR4 and KLB expression, or positive FGFR4 and FGF19 expression, or positive FGFR4, KLB and FGF19 expression.

DETAILED DESCRIPTION OF THE INVENTION

The invention provides, in a first aspect, a compound of formula (I) or a pharmaceutically acceptable salt thereof

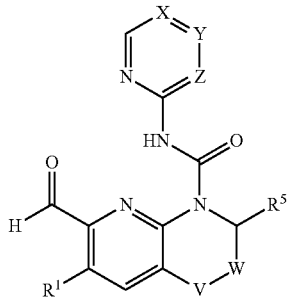

(I)

wherein
V is selected from $CH_2$, O, CH(OH);
W is selected from $CH_2$, $CH_2CH_2$, bond;
X is $C(R^X)$ or N;
Y is $C(R^Y)$ or N;
Z is CH or N;
wherein when X is N, Y and Z are not N;
wherein when Y is N, X and Z are not N;
wherein when Z is N, X and Y are not N;
$R^X$ is selected from hydrogen, halogen, halo$C_1$-$C_3$alkyl, cyano, $C_1$-$C_6$alkyl, hydroxy$C_1$-$C_6$alkyl;
$R^Y$ is selected from hydrogen, halogen, $C_1$-$C_3$alkyl, $C_1$-$C_6$alkoxy, hydroxy$C_1$-$C_3$alkoxy, $NR^{Y1}R^{Y2}$, cyano, $C_1$-$C_3$alkoxy$C_1$-$C_3$alkoxy, $C_1$-$C_3$alkoxy-halo$C_1$-$C_3$alkoxy, di($C_1$-$C_3$alkyl)amino$C_1$-$C_6$alkoxy, $O$—$(CH_2)_{0-1}$—$R^{Y3}$, $CR^{Y6}R^{Y7}$, $S$—$C_1$-$C_3$alkyl, halo$C_1$-$C_6$alkoxy optionally substituted with hydroxy;
or
$R^X$ and $R^Y$ together with the ring to which they are attached form a bicyclic aromatic ring system optionally further comprising one or two heteroatoms selected from N, O, or S, which ring system is optionally substituted with $C_1$-$C_3$alkyl;
$R^{Y1}$ is hydrogen and
$R^{Y2}$ is selected from $C_1$-$C_6$alkyl; hydroxy$C_1$-$C_6$alkyl; halo$C_1$-$C_6$alkyl optionally substituted with hydroxy; $C_1$-$C_4$alkoxy$C_1$-$C_6$alkyl; halo$C_1$-$C_3$alkoxy$C_1$-$C_6$alkyl; $(CH_2)_{0-1}$—$R^{Y4}$; di($C_1$-$C_3$alkyl)amino$C_1$-$C_6$alkyl substituted with hydroxy; bicyclo$C_5$-$C_8$alkyl optionally substituted with hydroxy$C_1$-$C_3$alkyl; phenyl substituted with $S(O)_2$—CH$(CH_3)_2$; $C_2$-$C_3$alkylsulfonic acid;
or
$R^{Y1}$ and $R^{Y2}$ together with the N atom to which they are attached form a saturated or unsaturated non-aromatic 6-membered heterocyclic ring which may contain an O atom, which ring may be substituted once or twice by $R^{Y5}$;
$R^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with $C_1$-$C_3$alkyl and/or oxo;
$R^{Y4}$ is a 4-, 5- or 6-membered saturated heterocyclic ring comprising at least one heteroatom selected from N, O, or S, which ring is optionally substituted with $C_1$-$C_3$alkyl;
$R^{Y5}$ is independently selected from $C_1$-$C_3$alkyl, hydroxy, di($C_1$-$C_3$alkyl)amino$C_1$-$C_3$alkyl,
or
two $R^{Y5}$ attached at the same carbon atom form together with the carbon atom to which they are attached a 5-membered saturated heterocyclic ring comprising at least one heteroatom selected from N, O or S, which ring is substituted once or more than once with $C_1$-$C_3$alkyl;

$R^{Y6}$ and $R^{Y7}$ together with the carbon atom to which they are attached form a 6-membered saturated or unsaturated non-aromatic heterocyclic ring comprising one heteroatom selected from N, O or S;
$R^1$ is selected from hydrogen; halogen; $C_1$-$C_3$alkyl; halo$C_1$-$C_3$alkyl; hydroxy$C_1$-$C_3$alkyl; $C_3$-$C_6$cycloalkyl; $CH_2NR^2R^3$; $CH(CH_3)NR^2R^3$; $C_1$-$C_3$alkoxy$C_1$-$C_3$alkyl; $CH_2CO_2H$; $C(O)H$; $C_1$-$C_3$alkoxy; a 5- or 6-membered saturated heterocyclic or aromatic heterocyclic ring comprising at least one heteroatom selected from N, O or S, which ring is optionally substituted once or more than once with a group independently selected from $C_1$-$C_3$alkyl, halo$C_1$-$C_3$alkyl, oxetanyl or oxo;
$R^2$ is selected from $C_1$-$C_3$alkyl, di($C_1$-$C_3$alkyl)amino$C_1$-$C_3$alkyl;
$R^3$ is selected from $C_1$-$C_3$alkyl, $C(O)C_1$-$C_3$alkyl, $C(O)$—$CH_2$—OH, $C(O)$—$CH_2$—O—$CH_3$, $C(O)$—$CH_2$—$N(CH_3)_2$, $S(O)_2CH_3$;
or
$R^2$ and $R^3$ together with the N atom to which they are attached form a saturated 5- or 6-membered ring optionally comprising one additional heteroatom selected from N, N-oxide, O or S, which ring may be substituted once or more than once with $R^4$;
$R^4$ is independently selected from $C_1$-$C_3$alkyl, di($C_1$-$C_3$alkyl)amino, $C(O)CH_3$, hydroxy;
or
two $R^4$ attached at the same carbon atom form together with the carbon atom to which they are attached a 4-, 5- or 6-membered non-aromatic heterocyclic ring comprising at least one heteroatom selected from N, O or S;
or
two $R^4$ attached at the same ring atom form an oxo group;
$R^5$ is selected from hydrogen or $C_1$-$C_3$alkyl
for use in the treatment of solid malignancies characterized by positive FGFR4 and KLB expression, or positive FGFR4 and FGF19 expression, or positive FGFR4, KLB and FGF19 expression.

Unless specified otherwise, the terms "compounds of the present invention" or "compounds of the invention" or "compounds used in the present invention" refer to compounds of formula (I), (Ia), (Ia-1) and salts thereof as defined herein, as well as all stereoisomers (including diastereoisomers and enantiomers), rotamers, tautomers, isomeric internal addition products and isotopically labeled compounds (including deuterium substitutions), as well as inherently formed moieties.

Unless otherwise defined, in the present description, a compound of formula (I) refers to:

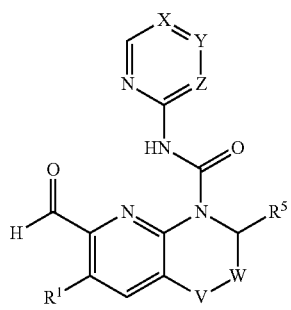

(I)

wherein
V is selected from CH$_2$, O, CH(OH);
W is selected from CH$_2$, CH$_2$CH$_2$, bond;
X is C(R$^X$) or N;
Y is C(R$^Y$) or N;
Z is CH or N;
wherein when X is N, Y and Z are not N;
wherein when Y is N, X and Z are not N;
wherein when Z is N, X and Y are not N;
R$^X$ is selected from hydrogen, halogen, haloC$_1$-C$_3$alkyl, cyano, C$_1$-C$_6$alkyl, hydroxyC$_1$-C$_6$alkyl;
R$^Y$ is selected from hydrogen, halogen, C$_1$-C$_3$alkyl, C$_1$-C$_6$alkoxy, hydroxyC$_1$-C$_3$alkoxy, NR$^{Y1}$R$^{Y2}$, cyano, C$_1$-C$_3$alkoxyC$_1$-C$_3$alkoxy, C$_1$-C$_3$alkoxy-haloC$_1$-C$_3$alkoxy, di(C$_1$-C$_3$alkyl)aminoC$_1$-C$_6$alkoxy, O—(CH$_2$)$_{0-1}$—R$^{Y3}$, CR$^{Y6}$R$^{Y7}$, S—C$_1$-C$_3$alkyl, haloC$_1$-C$_6$alkoxy optionally substituted with hydroxy;
or
R$^X$ and R$^Y$ together with the ring to which they are attached form a bicyclic aromatic ring system optionally further comprising one or two heteroatoms selected from N, O, or S, which ring system is optionally substituted with C$_1$-C$_3$alkyl;
R$^{Y1}$ is hydrogen and
R$^{Y2}$ is selected from C$_1$-C$_6$alkyl; hydroxyC$_1$-C$_6$alkyl; haloC$_1$-C$_6$alkyl optionally substituted with hydroxy; C$_1$-C$_4$alkoxyC$_1$-C$_6$alkyl; haloC$_1$-C$_3$alkoxyC$_1$-C$_6$alkyl; (CH$_2$)$_{0-1}$—R$^{Y4}$; di(C$_1$-C$_3$alkyl)aminoC$_1$-C$_6$alkyl substituted with hydroxy; bicycloC$_5$-C$_8$alkyl optionally substituted with hydroxyC$_1$-C$_3$alkyl; phenyl substituted with S(O)$_2$—CH(CH$_3$)$_2$; C$_2$-C$_3$alkylsulfonic acid;
or
R$^{Y1}$ and R$^{Y2}$ together with the N atom to which they are attached form a saturated or unsaturated non-aromatic 6-membered heterocyclic ring which may contain an O atom, which ring may be substituted once or twice by R$^{Y5}$;
R$^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with C$_1$-C$_3$alkyl and/or oxo;
R$^{Y4}$ is a 4-, 5- or 6-membered saturated heterocyclic ring comprising at least one heteroatom selected from N, O, or S, which ring is optionally substituted with C$_1$-C$_3$alkyl;
R$^{Y5}$ is independently selected from C$_1$-C$_3$alkyl, hydroxy, di(C$_1$-C$_3$alkyl)aminoC$_1$-C$_3$alkyl,
or
two R$^{Y5}$ attached at the same carbon atom form together with the carbon atom to which they are attached a 5-membered saturated heterocyclic ring comprising at least one heteroatom selected from N, O or S, which ring is substituted once or more than once with C$_1$-C$_3$alkyl;
R$^{Y6}$ and R$^{Y7}$ together with the carbon atom to which they are attached form a 6-membered saturated or unsaturated non-aromatic heterocyclic ring comprising one heteroatom selected from N, O or S;
R$^1$ is selected from hydrogen; halogen; C$_1$-C$_3$alkyl; haloC$_1$-C$_3$alkyl; hydroxyC$_1$-C$_3$alkyl; C$_3$-C$_6$cycloalkyl; CH$_2$NR$^2$R$^3$; CH(CH$_3$)NR$^2$R$^3$; C$_1$-C$_3$alkoxyC$_1$-C$_3$alkyl; CH$_2$CO$_2$H; C(O)H; C$_1$-C$_3$alkoxy; a 5- or 6-membered saturated heterocyclic or aromatic heterocyclic ring comprising at least one heteroatom selected from N, O or S, which ring is optionally substituted once or more than once with a group independently selected from C$_1$-C$_3$alkyl, haloC$_1$-C$_3$alkyl, oxetanyl or oxo;
R$^2$ is selected from C$_1$-C$_3$alkyl, di(C$_1$-C$_3$alkyl)aminoC$_1$-C$_3$alkyl;

R$^3$ is selected from C$_1$-C$_3$alkyl, C(O)C$_1$-C$_3$alkyl, C(O)—CH$_2$—OH, C(O)—CH$_2$—O—CH$_3$, C(O)—CH$_2$—N(CH$_3$)$_2$, S(O)$_2$CH$_3$;
or
R$^2$ and R$^3$ together with the N atom to which they are attached form a saturated 5- or 6-membered ring optionally comprising one additional heteroatom selected from N, N-oxide, O or S, which ring may be substituted once or more than once with R$^4$;
R$^4$ is independently selected from C$_1$-C$_3$alkyl, di(C$_1$-C$_3$alkyl)amino, C(O)CH$_3$, hydroxy;
or
two R$^4$ attached at the same carbon atom form together with the carbon atom to which they are attached a 4-, 5- or 6-membered non-aromatic heterocyclic ring comprising at least one heteroatom selected from N, O or S;
or
two R$^4$ attached at the same ring atom form an oxo group;
R$^5$ is selected from hydrogen or C$_1$-C$_3$alkyl.

Unless otherwise defined, in the present description, a compound of formula (Ia) refers to:

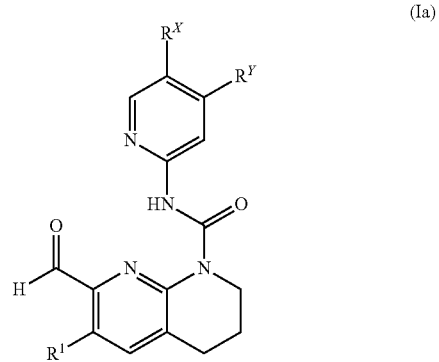

(Ia)

wherein
R$^X$ is selected from hydrogen, halogen, haloC$_1$-C$_3$alkyl, cyano, C$_1$-C$_6$alkyl, hydroxyC$_1$-C$_6$alkyl;
R$^Y$ is selected from hydrogen, halogen, C$_1$-C$_3$alkyl, C$_1$-C$_6$alkoxy, hydroxyC$_1$-C$_3$alkoxy, NR$^{Y1}$R$^{Y2}$, cyano, C$_1$-C$_3$alkoxyC$_1$-C$_3$alkoxy, C$_1$-C$_3$alkoxy-haloC$_1$-C$_3$alkoxy, di(C$_1$-C$_3$alkyl)aminoC$_1$-C$_6$alkoxy, O—(CH$_2$)$_{0-1}$—R$^{Y3}$, CR$^{Y6}$R$^{Y7}$, S—C$_1$-C$_3$alkyl, haloC$_1$-C$_6$alkoxy optionally substituted with hydroxy;
or
R$^X$ and R$^Y$ together with the ring to which they are attached form a bicyclic aromatic ring system optionally further comprising one or two heteroatoms selected from N, O, or S, which ring system is optionally substituted with C$_1$-C$_3$alkyl;
R$^{Y1}$ is hydrogen and
R$^{Y2}$ is selected from C$_1$-C$_6$alkyl; hydroxyC$_1$-C$_6$alkyl; haloC$_1$-C$_6$alkyl optionally substituted with hydroxyl; C$_1$-C$_4$alkoxyC$_1$-C$_6$alkyl; haloC$_1$-C$_3$alkoxyC$_1$-C$_6$alkyl; (CH$_2$)$_{0-1}$—R$^{Y4}$; di(C$_1$-C$_3$alkyl)aminoC$_1$-C$_6$alkyl substituted with hydroxy; bicycloC$_5$-C$_8$alkyl optionally substituted with hydroxyC$_1$-C$_3$alkyl; phenyl substituted with S(O)$_2$—CH(CH$_3$)$_2$; C$_2$-C$_3$alkylsulfonic acid;
or
R$^{Y1}$ and R$^{Y2}$ together with the N atom to which they are attached form a saturated or unsaturated non-aromatic 6-membered heterocyclic ring which may contain an O atom, which ring may be substituted once or twice by R$^{Y5}$;

R$^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with C$_1$-C$_3$alkyl and/or oxo;

R$^{Y4}$ is a 4-, 5- or 6-membered saturated heterocyclic ring comprising at least one heteroatom selected from N, O, or S, which ring is optionally substituted with C$_1$-C$_3$alkyl;

R$^{Y5}$ is independently selected from C$_1$-C$_3$alkyl, hydroxy, di(C$_1$-C$_3$alkyl)aminoC$_1$-C$_3$alkyl, or two R$^{Y5}$ attached at the same carbon atom form together with the carbon atom to which they are attached a 5-membered saturated heterocyclic ring comprising at least one heteroatom selected from N, O or S, which ring is substituted with C$_1$-C$_3$alkyl;

R$^{Y6}$ and R$^{Y7}$ together with the carbon atom to which they are attached form a 6-membered saturated or unsaturated non-aromatic heterocyclic ring comprising one heteroatom selected from N, O or S;

R$^1$ is selected from hydrogen, halogen, C$_1$-C$_3$alkyl, haloC$_1$-C$_3$alkyl, hydroxyC$_1$-C$_3$alkyl, C$_3$-C$_6$cycloalkyl, CH$_2$NR$^2$R$^3$, CH(CH$_3$)NR$^2$R$^3$, C$_1$-C$_3$alkoxyC$_1$-C$_3$alkyl, CH$_2$CO$_2$H, C(O)H;

R$^2$ is selected from C$_1$-C$_3$alkyl, di(C$_1$-C$_3$alkyl)aminoC$_1$-C$_3$alkyl;

R$^3$ is selected from C$_1$-C$_3$alkyl, C(O)C$_1$-C$_3$alkyl, C(O)—CH$_2$—OH, C(O)—CH$_2$—O—CH$_3$, C(O)—CH$_2$—N(CH$_3$)$_2$, S(O)$_2$CH$_3$;

or

R$^2$ and R$^3$ together with the N atom to which they are attached form a saturated 5- or 6-membered ring optionally comprising one additional heteroatom selected from N, N-oxide, O or S, which ring may be substituted once or more than once with R$^4$;

R$^4$ is independently selected from C$_1$-C$_3$alkyl, di(C$_1$-C$_3$alkyl)amino, C(O)CH$_3$, hydroxy;

or two R$^4$ attached at the same carbon atom form together with the carbon atom to which they are attached a 4-, 5- or 6-membered non-aromatic heterocyclic ring comprising at least one heteroatom selected from N, O or S;

or two R$^4$ attached at the same ring atom form an oxo group.

Unless otherwise defined, in the present description, a compound of formula (Ia-1) refers to:

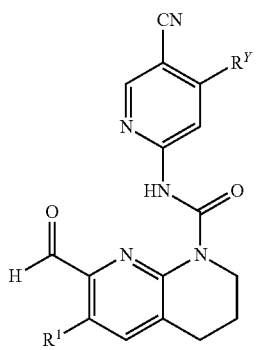

(Ia-1)

wherein

R$^Y$ is selected from hydrogen, halogen, C$_1$-C$_3$alkyl, C$_1$-C$_6$alkoxy, hydroxyC$_1$-C$_3$alkoxy, NR$^{Y1}$R$^{Y2}$, cyano, C$_1$-C$_3$alkoxyC$_1$-C$_3$alkoxy, C$_1$-C$_3$alkoxy-haloC$_1$-C$_3$alkoxy, di(C$_1$-C$_3$alkyl)aminoC$_1$-C$_6$alkoxy, O—(CH$_2$)$_{0-1}$—R$^{Y3}$, CR$^{Y6}$R$^{Y7}$, S—C$_1$-C$_3$alkyl, haloC$_1$-C$_6$alkoxy optionally substituted with hydroxy;

R$^{Y1}$ is hydrogen and

R$^{Y2}$ is selected from C$_1$-C$_6$alkyl; hydroxyC$_1$-C$_6$alkyl; haloC$_1$-C$_6$alkyl optionally substituted with hydroxyl; C$_1$-C$_4$alkoxyC$_1$-C$_6$alkyl; haloC$_1$-C$_3$alkoxyC$_1$-C$_6$alkyl; (CH$_2$)$_{0-1}$—R$^{Y4}$; di(C$_1$-C$_3$alkyl)aminoC$_1$-C$_6$alkyl substituted with hydroxy; bicycloC$_5$-C$_8$alkyl optionally substituted with hydroxyC$_1$-C$_3$alkyl; phenyl substituted with S(O)$_2$—CH(CH$_3$)$_2$; C$_2$-C$_3$alkylsulfonic acid;

or

R$^{Y1}$ and R$^{Y2}$ together with the N atom to which they are attached form a saturated or unsaturated non-aromatic 6-membered heterocyclic ring which may contain an O atom, which ring may be substituted once or twice by R$^{Y5}$;

R$^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with C$_1$-C$_3$alkyl and/or oxo;

R$^{Y4}$ is a 4-, 5- or 6-membered saturated heterocyclic ring comprising at least one heteroatom selected from N, O, or S, which ring is optionally substituted with C$_1$-C$_3$alkyl;

R$^{Y5}$ is independently selected from C$_1$-C$_3$alkyl, hydroxy, di(C$_1$-C$_3$alkyl)aminoC$_1$-C$_3$alkyl, or two R$^{Y5}$ attached at the same carbon atom form together with the carbon atom to which they are attached a 5-membered saturated heterocyclic ring comprising at least one heteroatom selected from N, O or S, which ring is substituted with C$_1$-C$_3$alkyl;

R$^{Y6}$ and R$^{Y7}$ together with the carbon atom to which they are attached form a 6-membered saturated or unsaturated non-aromatic heterocyclic ring comprising one heteroatom selected from N, O or S;

R$^1$ is selected from hydrogen, halogen, C$_1$-C$_3$alkyl, haloC$_1$-C$_3$alkyl, hydroxyC$_1$-C$_3$alkyl, C$_3$-C$_6$cycloalkyl, CH$_2$NR$^2$R$^3$, CH(CH$_3$)NR$^2$R$^3$, C$_1$-C$_3$alkoxyC$_1$-C$_3$alkyl, CH$_2$CO$_2$H, C(O)H;

R$^2$ is selected from C$_1$-C$_3$alkyl, di(C$_1$-C$_3$alkyl)aminoC$_1$-C$_3$alkyl;

R$^3$ is selected from C$_1$-C$_3$alkyl, C(O)C$_1$-C$_3$alkyl, C(O)—CH$_2$—OH, C(O)—CH$_2$—O—CH$_3$, C(O)—CH$_2$—N(CH$_3$)$_2$, S(O)$_2$CH$_3$;

or

R$^2$ and R$^3$ together with the N atom to which they are attached form a saturated 5- or 6-membered ring optionally comprising one additional heteroatom selected from N, N-oxide, O or S, which ring may be substituted once or more than once with R$^4$;

R$^4$ is independently selected from C$_1$-C$_3$alkyl, di(C$_1$-C$_3$alkyl)amino, C(O)CH$_3$, hydroxy;

or two R$^4$ attached at the same carbon atom form together with the carbon atom to which they are attached a 4-, 5- or 6-membered non-aromatic heterocyclic ring comprising at least one heteroatom selected from N, O or S;

or two R$^4$ attached at the same ring atom form an oxo group.

In particular, the compounds of formula (I), (Ia), (Ia-1) are able to readily form tautomers and isomeric internal addition products as depicted below.

For instance, compounds of the invention where R$^1$ is hydroxymethyl, CH$_2$CO$_2$H, 4-piperidinyl e.g. compounds (I-1), (I-2) and (I-5), may be in the form as depicted below (compounds (I-1a), (I-2a) and (I-5a)).

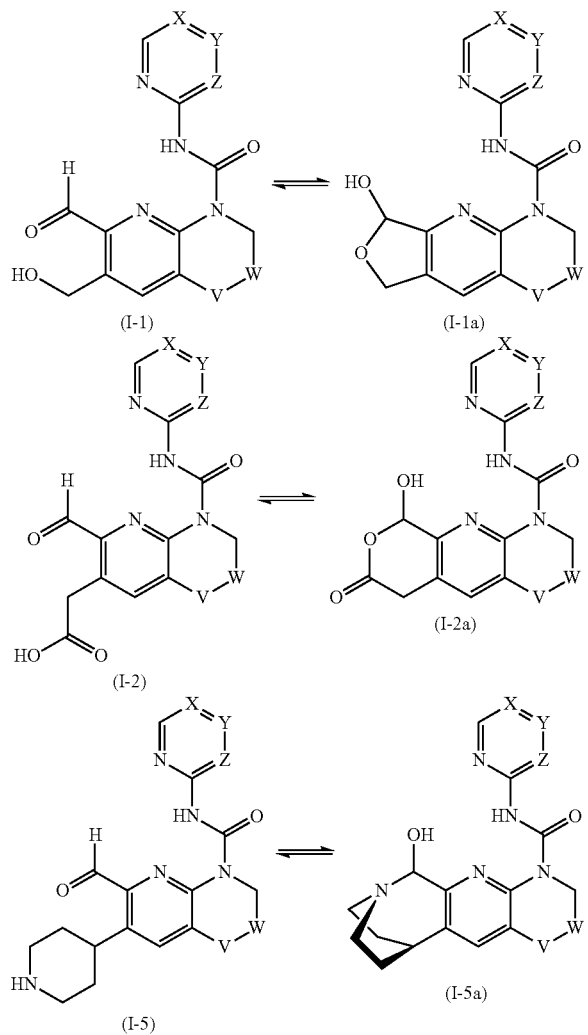

Thus, the compounds (I-1), (I-2), (I-5) and their isomers (I-1a), (I-2a), (I-5a) wherein V, W, X, Y and Z are as defined herein, also form part of the invention.

The presence of tautomers or isomeric internal additional products can be identified by a person of skill in the art with tools such as NMR.

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_1$-$C_4$alkyl" is to be construed accordingly. The term "$C_1$-$C_3$alkyl" is to be construed accordingly.

Examples of $C_1$-$C_6$alkyl include, but are not limited to, methyl, ethyl, n-propyl, 1-methylethyl (iso-propyl), n-butyl, n-pentyl and 1,1-dimethylethyl (t-butyl).

As used herein, the term "hydroxy$C_1$-$C_6$alkyl" refers to a radical of formula —$R_a$—OH, wherein $R_a$ is $C_{1-6}$alkyl as defined above. Examples of hydroxy$C_1$-$C_6$alkyl include, but are not limited to, hydroxymethyl, 2-hydroxy-ethyl, 2-hydroxy-propyl, 3-hydroxy-propyl and 5-hydroxy-pentyl.

As used herein, the term "$C_3$-$C_6$cycloalkyl" refers to saturated monocyclic hydrocarbon groups of 3-6 carbon atoms. Examples of $C_3$-$C_6$cycloalkyl include cyclopropyl, cyclobutyl, cyclopentyl and cyclohexyl.

As used herein, the term "$C_1$-$C_6$alkoxy" refers to a radical of the formula —$OR_a$ where $R_a$ is a $C_1$-$C_6$alkyl radical as generally defined above. The term "$C_1$-$C_3$alkoxy" is to be construed accordingly.

Examples of $C_1$-$C_6$alkoxy include, but are not limited to, methoxy, ethoxy, propoxy, isopropoxy, butoxy, isobutoxy, pentoxy, and hexoxy.

As used herein, the term "$C_1$-$C_4$alkoxy$C_1$-$C_6$alkyl" refers to a radical of the formula —$R_b$—O—$R_a$ where $R_a$ is a $C_1$-$C_4$alkyl radical and $R_b$ is a $C_1$-$C_6$alkyl radical as defined above. The term "$C_1$-$C_3$alkoxy$C_1$-$C_6$alkyl" is to be construed accordingly. The oxygen atom may be bonded to any carbon atom in either alkyl radical. Examples of $C_1$-$C_4$alkoxy$C_1$-$C_6$alkyl include, but are not limited to, methoxy-methyl, methoxy-ethyl, ethoxy-ethyl, 1-ethoxy-propyl and 2-methoxy-butyl.

"Halogen" or "halo" refers to bromo, chloro, fluoro or iodo.

As used herein, the term "halogen$C_1$-$C_6$alkyl" or "halo$C_1$-$C_6$alkyl" refers to $C_1$-$C_6$alkyl radical, as defined above, substituted by one or more halo radicals, as defined above. Examples of halogen$C_1$-$C_6$alkyl include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "halo$C_1$-$C_3$alkoxy" refers to $C_1$-$C_3$alkoxy as defined above, substituted by one or more halo radicals, as defined above. Examples of halo$C_1$-$C_3$alkoxy include, but are not limited to, trifluoromethoxy, difluoromethoxy, trifluoroethoxy.

As used herein, the term "hydroxy$C_1$-$C_3$alkoxy" refers to a $C_1$-$C_3$alkoxy radical as defined above, wherein one of the hydrogen atoms of the $C_1$-$C_3$alkoxy radical is replaced by OH. Examples of hydroxy$C_1$-$C_3$alkoxy include, but are not limited to, hydroxymethoxy, hydroxyethoxy.

As used herein, the term "$C_1$-$C_3$alkoxy$C_1$-$C_3$alkoxy" refers to a $C_1$-$C_3$alkoxy radical as defined above, wherein one of the hydrogen atoms of the $C_{1-3}$alkoxy radical is replaced by —O—$C_1$-$C_3$alkyl.

Examples of $C_1$-$C_3$alkoxy$C_1$-$C_3$alkoxy include, but are not limited to, methoxymethoxy, ethoxymethoxy.

As used herein, the term "$C_1$-$C_3$alkoxy-halo$C_1$-$C_3$alkoxy" refers to a halo$C_1$-$C_3$alkoxy radical as defined above, wherein one of the hydrogen atoms of the halo$C_1$-$C_3$alkoxy radical is replaced by —O—$C_1$-$C_3$alkyl. Examples of $C_1$-$C_3$alkoxy-halo$C_1$-$C_3$alkoxy include, but are not limited to, methoxytrifluoropropyloxy.

As used herein, the term "di($C_1$-$C_3$alkyl)amino$C_1$-$C_6$alkyl" refers to a radical of the formula —$R_{a1}$—N($R_{a2}$)—$R_{a2}$ where $R_{a1}$ is a $C_1$-$C_6$alkyl radical as defined above and each $R_{a2}$ is a $C_1$-$C_3$alkyl radical, which may be the same or different, as defined above. The nitrogen atom may be bonded to any carbon atom in any alkyl radical. As described herein, the "di$C_1$-$C_3$alkylamino$C_1$-$C_6$alkyl" may be substituted with hydroxy.

As used herein, the term "di($C_1$-$C_3$alkyl)amino$C_1$-$C_6$alkoxy" refers to a radical of the formula —$R_a$—N($R_{a2}$)—$R_{a2}$ where $R_{a1}$ is a $C_1$-$C_6$alkoxy radical as defined above and each $R_{a2}$ is a $C_1$-$C_3$alkyl radical, which may be the same or different, as defined above.

As used herein, the term "6-membered saturated heterocyclic ring comprising one heteroatom selected from N, O or S" includes piperidyl, tetrahydropyranyl and tetrahydrothiopyranyl.

As used herein, the term "6-membered unsaturated non-aromatic heterocyclic ring comprising one heteroatom selected from N, O or S" includes, but is not limited to, tetrahydropyridinyl, dihydropyranyl, dihydrothiopyranyl.

As used herein, the term "a 4-, 5-, or 6-membered saturated heterocyclic ring comprising at least one heteroatom selected from N, O or S" includes as examples, but is not limited to, azetidinyl, oxetanyl, pyrrolidyl, tetrahydrofuryl, tetrahydrothienyl, piperidyl, piperazinyl, tetrahydropyranyl, morpholinyl.

As used herein, the term "5-membered saturated heterocyclic ring" includes as example, but is not limited to, pyrrolidine.

As used herein, the term "a saturated 5- or 6-membered ring optionally comprising one additional heteroatom selected from N, O or S" in relation to the embodiments where $R^2$ and $R^3$ together with the N atom to which they are attached form said ring, includes as examples, but is not limited to, pyrrolidine, oxazolidine, piperazine, morpholine, thiomorpholine rings.

As used herein, the term a "4-, 5- or 6-membered non-aromatic heterocyclic ring comprising at least one heteroatom selected from N, O or S" includes 4-, 5-, or 6-membered saturated heterocyclic ring comprising at least one heteroatom selected from N, O or S as defined herein. It also includes 4-, 5-, or 6-membered unsaturated heterocyclic ring comprising at least one heteroatom selected from N, O or S.

As used herein, the term "bicyclic aromatic ring system optionally further comprising one or two heteroatoms selected from N, O or S" includes, but is not limited to, imidazopyridine and isothiazolopyridine.

As used herein, the term "bicyclo$C_5$-$C_8$alkyl" refers to bicyclic hydrocarbon groups comprising 5 to 8 carbon atoms including, but not limited to, bicyclo[2.1.1]hexyl, bicyclo[1.1.1]pentyl, bicyclo[2.2.1]heptanyl, bicyclo[2.2.2]octyl.

As used herein, the term "optionally substituted" as used in the description of $R^Y$, $R^X$ and $R^Y$ together, $R^{Y2}$, $R^{Y3}$, $R^{Y4}$ includes unsubstituted or substituted once or twice.

As used herein, the term "substituted" as used, for example in the description of $R^{Y2}$, two $R^Y$, includes substituted once or twice, preferably once.

As used herein, the term "more than once" when referring to substituent $R^4$, includes 2, 3, 4, 5, or 6 times. Preferably, it includes 2 or 3 times.

As used herein, the term "solid malignancies" refers to non-hematological malignancies.

As used herein, the term "FGFR4" refers to fibroblast growth factor receptor 4, also known as CD334, JTK2, TKF (gene ID: 2264).

As used herein, the term "FGF19" refers to fibroblast growth factor 19 (gene ID: 9965)

As used herein, the term "KLB" refers to the beta-klotho protein (gene ID: 152831).

As used herein, the term "biomarkers of the invention" refers to any of FGFR4, KLB and FGF19.

Any positive expression in FGFR4, KLB and/or FGF19 as described herein can be assessed by methods known to the skilled person such as e.g. RT-qPCR, Western blotting, ELISA, immunohistochemistry. For example, any positive expression in FGFR4, KLB and/or FGF19 can be assayed by detecting for expression of the RNA levels of FGFR4, KLB and/or FGF19 or detecting expression of the FGFR4, KLB and/or FGF19 protein product by methods known to the skilled person. It is within the reach of the skilled person to determine a positive expression of FGFR4, FGF19 and/or KLB.

For example, the positive expression in FGFR4, KLB and/or FGF19 can be assessed as described in the examples.

The term "assaying" is used to refer to the act of identifying, screening, probing or determining, which act may be performed by any conventional means. For example, a sample may be assayed for the presence of a particular biomarker by using an ELISA assay, a Northern blot, imaging, etc. to detect whether a specific biomarker is present in the sample. The terms "assaying" and "determining" contemplate a transformation of matter, e.g., a transformation of a biological sample, e.g., a blood sample or other tissue sample, from one state to another by means of subjecting that sample to physical testing. Further, as used herein, the terms "assaying" and "determining" are used to mean testing and/or measuring. The phrase "assaying a biological sample from the patient for the presence or the positive expression of FGF19 or FGF19 and KLB or FGFR4, FGF19 and/or KLB" and the like is used to mean that a sample may be tested (either directly or indirectly) for either the presence or absence of a given biomarker or for the level of a particular biomarker. It will be understood that the positive expression of a biomarker FGFR4, KLB and/or FGF19 in a substance denotes one probability and the absence of a substance denotes a different probability, then either the presence or the absence of such substance may be used to guide a therapeutic decision.

As used herein, "selecting" and "selected" in reference to a patient is used to mean that a particular patient is specifically chosen from a larger group of patients on the basis of (due to) the particular patient having a predetermined criteria. Similarly, "selectively treating" refers to providing treatment to a patient having a particular disease, where that patient is specifically chosen from a larger group of patients on the basis of the particular patient having a predetermined criterion. Similarly, "selectively administering" refers to administering a drug to a patient that is specifically chosen from a larger group of patients on the basis of (due to) the particular patient having a predetermined criterion. By selecting, selectively treating and selectively administering, it is meant that a patient is delivered a personalized therapy based on the patient's particular biology, rather than being delivered a standard treatment regimen based solely on the patient having a particular disease. Selecting, in reference to a method of treatment as used herein, does not refer to fortuitous treatment of a patient that has the biomarker, but rather refers to the deliberate choice to administer treatment to a patient based on the patient having positive expression of the biomarker. Thus, selective treatment differs from standard treatment, which delivers a particular drug to all patients, regardless of their biomarker.

As used herein, "likelihood" and "likely" is a measurement of how probable an event is to occur. It may be used interchangeably with "probability". Likelihood refers to a probability that is more than speculation, but less than certainty. Thus, an event is likely if a reasonable person using common sense, training or experience concludes that, given the circumstances, an event is probable. In some embodiments, once likelihood has been ascertained, the patient may be treated (or treatment continued, or treatment proceed with a dosage increase) with the test compound. In one embodiment, the "likelihood" and "likely" denote a chance in percent of how probable an event is to occur.

The phrase "increased likelihood" refers to an increase in the probability that an event will occur. For example, some methods herein allow prediction of whether a patient will display an increased likelihood of responding to treatment with the test molecule or an increased likelihood of responding better to treatment with the test molecule. In one embodiment the increased likelihood means that there is more than 50% chance, more than 60% chance, more than 70% or more than 80% chance that an event will occur. Equally, a decreased likelihood means, that the chance is lower than 50%, lower than 60%, lower than 70% or lower than 80%, respectively, that an event will occur.

In an embodiment of the invention, there is provided a compound of formula (Ia) or a pharmaceutically acceptable salt thereof for use in the treatment of solid malignancies characterized by positive FGFR4 and KLB expression, or positive FGFR4 and FGF19 expression, or positive FGFR4, KLB and FGF19 expression.

In an embodiment of the invention, there is provided a compound of formula (Ia) or a pharmaceutically acceptable salt thereof

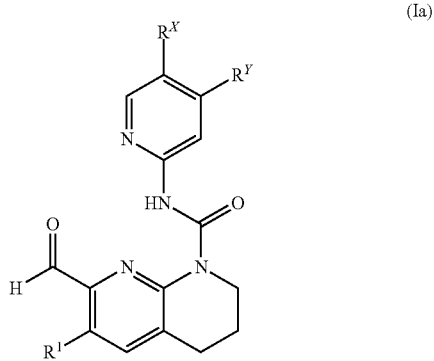

(Ia)

wherein $R^X$ is selected from halogen, haloC$_1$-C$_3$alkyl, cyano;

$R^Y$ is selected from hydrogen, halogen, C$_1$-C$_3$alkyl, C$_1$-C$_6$alkoxy, haloC$_1$-C$_3$alkoxy, hydroxyC$_1$-C$_3$alkoxy, NR$^{Y1}$R$^{Y2}$, C$_1$-C$_3$alkoxyC$_1$-C$_3$alkoxy, C$_1$-C$_3$alkoxy-haloC$_1$-C$_3$alkoxy, O—(CH$_2$)$_{0-1}$—R$^{Y3}$;

$R^{Y1}$ is hydrogen and $R^{Y2}$ is selected from C$_1$-C$_6$alkyl, hydroxyC$_1$-C$_6$alkyl, C$_1$-C$_3$alkoxyC$_1$-C$_6$alkyl, (CH$_2$)$_{0-1}$—R$^{Y4}$, haloC$_1$-C$_6$alkyl optionally substituted with hydroxyl;

$R^{Y3}$ is a 4-, 5- or 6-membered saturated heterocyclic ring comprising at least one heteroatom selected from N, O or S, which ring is optionally substituted with C$_1$-C$_3$alkyl;

$R^{Y4}$ is a 4-, 5-, or 6-membered saturated heterocyclic ring comprising at least one heteroatom selected from N, O or S, which ring is optionally substituted with C$_1$-C$_3$alkyl;

$R^1$ is selected from hydrogen, halogen, C$_1$-C$_3$alkyl, haloC$_1$-C$_3$alkyl, hydroxyC$_1$-C$_3$alkyl, C$_3$-C$_6$cycloalkyl, CH$_2$NR$^2$R$^3$, CH(CH$_3$)NR$^2$R$^3$;

$R^2$ is C$_1$-C$_3$alkyl and $R^3$ is selected from C$_1$-C$_3$alkyl, C(O)—C$_1$-C$_3$alkyl or $R^2$ and $R^3$ together with the N atom to which they are attached form a saturated 5- or 6-membered ring optionally comprising one additional heteroatom selected from N, O or S, which ring may be substituted once or more than once with $R^4$;

$R^4$ is independently selected from C$_1$-C$_3$alkyl, di(C$_1$-C$_3$alkyl)amino or two R$_4$ attached at the same carbon atom form an oxo group for use in the treatment of solid malignancies characterized by positive FGFR4 expression or positive FGFR4 and KLB expression, or positive FGFR4 and FGF19 expression, or positive FGFR4, KLB and FGF19 expression.

In an embodiment of the invention, there is provided a compound of formula (Ia-1) or a pharmaceutically acceptable salt thereof for use in the treatment of solid malignancies characterized by positive FGFR4 and KLB expression, or positive FGFR4 and FGF19 expression, or positive FGFR4, KLB and FGF19 expression.

In an embodiment of the invention, there is provided a compound of formula (Ia-1) or a pharmaceutically acceptable salt thereof

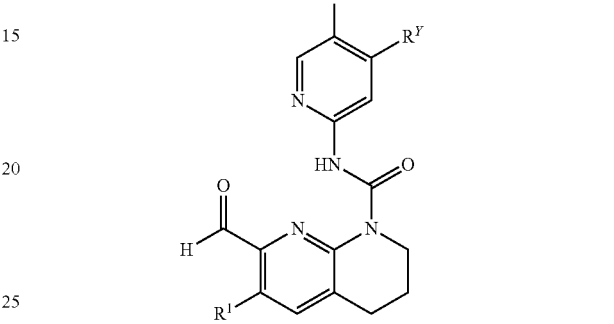

(Ia-1)

wherein $R^Y$ is selected from hydrogen, halogen, C$_1$-C$_3$alkyl, C$_1$-C$_6$alkoxy, haloC$_1$-C$_3$alkoxy, hydroxyC$_1$-C$_3$alkoxy, NR$^{Y1}$R$^{Y2}$, C$_1$-C$_3$alkoxyC$_1$-C$_3$alkoxy, C$_1$-C$_3$alkoxy-haloC$_1$-C$_3$alkoxy, O—(CH$_2$)$_{0-1}$—R$^{Y3}$;

$R^{Y1}$ is hydrogen and $R^{Y2}$ is C$_1$-C$_6$alkyl, hydroxyC$_1$-C$_6$alkyl, C$_1$-C$_4$alkoxyC$_1$-C$_6$alkyl, (CH$_2$)$_{0-1}$-R$^{Y4}$haloC$_1$-C$_6$alkyl optionally substituted with hydroxyl;

$R^{Y3}$ is a 4-, 5- or 6-membered saturated heterocyclic ring comprising at least one heteroatom selected from N, O or S, which ring is optionally substituted with C$_1$-C$_3$alkyl;

$R^{Y4}$ is a 4-, 5-, or 6-membered saturated heterocyclic ring comprising at least one heteroatom selected from N, O or S, which ring is optionally substituted with C$_1$-C$_3$alkyl;

$R^1$ is selected from hydrogen, halogen, C$_1$-C$_3$alkyl, haloC$_1$-C$_3$alkyl, hydroxyC$_1$-C$_3$alkyl, C$_3$-C$_6$cycloalkyl, CH$_2$NR$^2$R$^3$, CH(CH$_3$)NR$^2$R$^3$;

$R^2$ is C$_1$-C$_3$alkyl and $R^3$ is selected from C$_1$-C$_3$alkyl, C(O)—C$_1$-C$_3$alkyl or $R^2$ and $R^3$ together with the N atom to which they are attached form a saturated 5- or 6-membered ring optionally comprising one additional heteroatom selected from N, O or S, which ring may be substituted once or more than once with $R^4$;

$R^4$ is independently selected from C$_1$-C$_3$alkyl, di(C$_1$-C$_3$alkyl)amino or two R$_4$ attached at the same carbon atom form an oxo group for use in the treatment of solid malignancies characterized by positive FGFR4 and KLB expression, or positive FGFR4 and FGF19 expression, or positive FGFR4, KLB and FGF19 expression.

In an embodiment of the invention, there is provided a compound of formula (Ia-1) or a pharmaceutically acceptable salt thereof

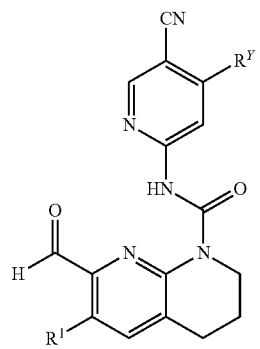

(Ia-1)

wherein $R^Y$ is selected from $NR^{Y1}R^{Y2}$, $C_1$-$C_3$alkoxy$C_1$-$C_3$alkoxy, $O$—$(CH_2)_{0-1}$—$R^{Y3}$;
$R^{Y1}$ is hydrogen and
$R^{Y2}$ is selected from $C_1$-$C_6$alkyl; hydroxy$C_1$-$C_6$alkyl; halo$C_1$-$C_6$alkyl optionally substituted with hydroxyl; $C_1$-$C_4$alkoxy$C_1$-$C_6$alkyl; halo$C_1$-$C_3$alkoxy$C_1$-$C_6$alkyl; $(CH_2)_{0-1}$—$R^{Y4}$; di($C_1$-$C_3$alkyl)amino$C_1$-$C_6$alkyl substituted with hydroxy; bicyclo$C_5$-$C_8$alkyl optionally substituted with hydroxy$C_1$-$C_3$alkyl; phenyl substituted with $S(O)_2$—CH$(CH_3)_2$; $C_2$-$C_3$alkylsulfonic acid;
or
$R^{Y1}$ and $R^{Y2}$ together with the N atom to which they are attached form a saturated or unsaturated non-aromatic 6-membered heterocyclic ring which may contain an O atom, which ring may be substituted once or twice by $R^{Y5}$;
$R^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with $C_1$-$C_3$alkyl and/or oxo;
$R^{Y4}$ is a 4-, 5- or 6-membered saturated heterocyclic ring comprising at least one heteroatom selected from N, O, or S, which ring is optionally substituted with $C_1$-$C_3$alkyl;
$R^{Y5}$ is independently selected from $C_1$-$C_3$alkyl, hydroxy, di($C_1$-$C_3$alkyl)amino$C_1$-$C_3$alkyl,
or
two $R^{Y5}$ attached at the same carbon atom form together with the carbon atom to which they are attached a 5-membered saturated heterocyclic ring comprising at least one heteroatom selected from N, O or S, which ring is substituted with $C_1$-$C_3$alkyl;
$R^{Y6}$ and $R^{Y7}$ together with the carbon atom to which they are attached form a 6-membered saturated or unsaturated non-aromatic heterocyclic ring comprising one heteroatom selected from N, O or S;
$R^1$ is selected from hydrogen, halogen, $C_1$-$C_3$alkyl, halo$C_1$-$C_3$alkyl, hydroxy$C_1$-$C_3$alkyl, $C_3$-$C_6$cycloalkyl, $CH_2NR^2R^3$, $CH(CH_3)NR^2R^3$, $C_1$-$C_3$alkoxy$C_1$-$C_3$alkyl, $CH_2CO_2H$, $C(O)H$;
$R^2$ is selected from $C_1$-$C_3$alkyl, di($C_1$-$C_3$alkyl)amino$C_1$-$C_3$alkyl;
$R^3$ is selected from $C_1$-$C_3$alkyl, $C(O)C_1$-$C_3$alkyl, $C(O)$—$CH_2$—OH, $C(O)$—$CH_2$—O—$CH_3$, $C(O)$—$CH_2$—$N(CH_3)_2$, $S(O)_2CH_3$;
or
$R^2$ and $R^3$ together with the N atom to which they are attached form a saturated 5- or 6-membered ring optionally comprising one additional heteroatom selected from N, N-oxide, O or S, which ring may be substituted once or more than once with $R^4$;

$R^4$ is independently selected from $C_1$-$C_3$alkyl, di($C_1$-$C_3$alkyl)amino, $C(O)CH_3$, hydroxy;
or
two $R^4$ attached at the same carbon atom form together with the carbon atom to which they are attached a 4-, 5- or 6-membered non-aromatic heterocyclic ring comprising at least one heteroatom selected from N, O or S;
or
two $R^4$ attached at the same ring atom form an oxo group
for use in the treatment of solid malignancies characterized by positive FGFR4 and KLB expression, or positive FGFR4 and FGF19 expression, or positive FGFR4, KLB and FGF19 expression.

In an embodiment of the invention, there is provided a compound of formula (Ia-1) or a pharmaceutically acceptable salt thereof

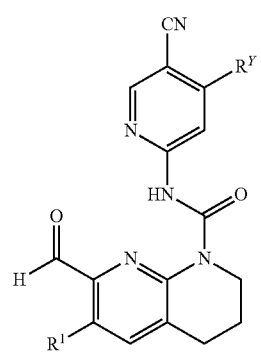

(Ia-1)

wherein
$R^Y$ is selected from $NR^{Y1}R^{Y2}$, $C_1$-$C_3$alkoxy$C_1$-$C_3$alkoxy, $O$—$(CH_2)_{0-1}$—$R^{Y3}$;
$R^{Y3}$ is a 4-, 5- or 6-membered saturated heterocyclic ring comprising at least one heteroatom selected from N, O or S, which ring is optionally substituted with $C_1$-$C_3$alkyl;
$R^{Y1}$ is hydrogen and $R^{Y2}$ is $C_1$-$C_6$alkyl, $C_1$-$C_3$alkoxy$C_1$-$C_6$alkyl, $(CH_2)_{0-1}$—$R^{Y4}$;
$R^{Y4}$ is a 4-, 5-, or 6-membered saturated heterocyclic ring comprising at least one heteroatom selected from N, O or S, which ring is optionally substituted with $C_1$-$C_3$alkyl;
$R^1$ is selected from hydrogen, halogen, $C_1$-$C_3$alkyl, halo$C_1$-$C_3$alkyl, hydroxy$C_1$-$C_3$alkyl, $C_3$-$C_6$cycloalkyl, $CH_2NR^2R^3$, $CH(CH_3)NR^2R^3$;
$R^2$ is $C_1$-$C_3$alkyl and $R^3$ is selected from $C_1$-$C_3$alkyl, $C(O)$—$C_1$-$C_3$alkyl or
$R^2$ and $R^3$ together with the N atom to which they are attached form a saturated 5- or 6-membered ring optionally comprising one additional heteroatom selected from N, O or S, which ring may be substituted once or more than once with $R^4$;
$R^4$ is independently selected from $C_1$-$C_3$alkyl, di($C_1$-$C_3$alkyl)amino or two $R_4$ attached at the same carbon atom form an oxo group
for use in the treatment of solid malignancies characterized by positive FGFR4 and KLB expression, or positive FGFR4 and FGF19 expression, or positive FGFR4, KLB and FGF19 expression.

In an embodiment of the invention, there is provided a compound of formula (Ia-1) or a pharmaceutically acceptable salt thereof

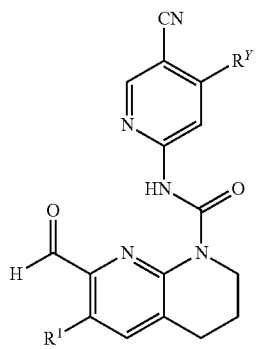

(Ia-1)

wherein $R^Y$ is selected from $NR^{Y1}R^{Y2}$, $C_1$-$C_3$alkoxy$C_1$-$C_3$alkoxy;
$R^{Y1}$ is hydrogen and
$R^{Y2}$ is selected from $C_1$-$C_6$alkyl; hydroxy$C_1$-$C_6$alkyl; halo$C_1$-$C_6$alkyl optionally substituted with hydroxyl; $C_1$-$C_4$alkoxy$C_1$-$C_6$alkyl; halo$C_1$-$C_3$alkoxy$C_1$-$C_6$alkyl; $(CH_2)_{0-1}$—$R^{Y4}$; di($C_1$-$C_3$alkyl)amino$C_1$-$C_6$alkyl substituted with hydroxy; bicyclo$C_5$-$C_8$alkyl optionally substituted with hydroxy$C_1$-$C_3$alkyl; phenyl substituted with $S(O)_2$—CH$(CH_3)_2$; $C_2$-$C_3$alkylsulfonic acid;
or
$R^{Y1}$ and $R^{Y2}$ together with the N atom to which they are attached form a saturated or unsaturated non-aromatic 6-membered heterocyclic ring which may contain an O atom, which ring may be substituted once or twice by $R^{Y5}$;
$R^{Y4}$ is a 4-, 5- or 6-membered saturated heterocyclic ring comprising at least one heteroatom selected from N, O, or S, which ring is optionally substituted with $C_1$-$C_3$alkyl;
$R^{Y5}$ is independently selected from $C_1$-$C_3$alkyl, hydroxy, di($C_1$-$C_3$alkyl)amino$C_1$-$C_3$alkyl,
or
two $R^{Y5}$ attached at the same carbon atom form together with the carbon atom to which they are attached a 5-membered saturated heterocyclic ring comprising at least one heteroatom selected from N, O or S, which ring is substituted with $C_1$-$C_3$alkyl;
$R^1$ is selected from hydrogen, halogen, $C_1$-$C_3$alkyl, halo$C_1$-$C_3$alkyl, hydroxy$C_1$-$C_3$alkyl, $C_3$-$C_6$cycloalkyl, $CH_2NR^2R^3$, $CH(CH_3)NR^2R^3$, $C_1$-$C_3$alkoxy$C_1$-$C_3$alkyl, $CH_2CO_2H$, C(O)H;
$R^2$ is selected from $C_1$-$C_3$alkyl, di($C_1$-$C_3$alkyl)amino$C_1$-$C_3$alkyl;
$R^3$ is selected from $C_1$-$C_3$alkyl, C(O)$C_1$-$C_3$alkyl, C(O)—$CH_2$—OH, C(O)—$CH_2$—O—$CH_3$, C(O)—$CH_2$—N(CH$_3$)$_2$, S(O)$_2$CH$_3$;
or
$R^2$ and $R^3$ together with the N atom to which they are attached form a saturated 5- or 6-membered ring optionally comprising one additional heteroatom selected from N, N-oxide, O or S, which ring may be substituted once or more than once with $R^4$;
$R^4$ is independently selected from $C_1$-$C_3$alkyl, di($C_1$-$C_3$alkyl)amino, C(O)CH$_3$, hydroxy;
or
two $R^4$ attached at the same carbon atom form together with the carbon atom to which they are attached a 4-, 5- or 6-membered non-aromatic heterocyclic ring comprising at least one heteroatom selected from N, O or S;
or
two $R^4$ attached at the same ring atom form an oxo group for use in the treatment of solid malignancies characterized by positive FGFR4 and KLB expression, or positive FGFR4 and FGF19 expression, or positive FGFR4, KLB and FGF19 expression.

In an embodiment of the invention, there is provided a compound of formula (Ia-1) or a pharmaceutically acceptable salt thereof

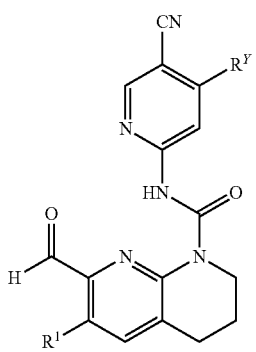

(Ia-1)

wherein
$R^Y$ is selected from $NR^{Y1}R^{Y2}$, $C_1$-$C_3$alkoxy$C_1$-$C_3$alkoxy;
$R^{Y1}$ is hydrogen and $R^{Y2}$ is selected from $C_1$-$C_6$alkyl, $C_1$-$C_3$alkoxy$C_1$-$C_6$alkyl, $(CH_2)_{0-1}$—$R^{Y4}$;
$R^{Y4}$ is a 4-, 5-, or 6-membered saturated heterocyclic ring comprising at least one heteroatom selected from N, O or S, which ring is optionally substituted with $C_1$-$C_3$alkyl;
$R^1$ is selected from $CH_2NR^2R^3$, $CH(CH_3)NR^2R^3$;
$R^2$ is $C_1$-$C_3$alkyl and $R^3$ is selected from $C_1$-$C_3$alkyl, C(O)—$C_1$-$C_3$alkyl or
$R^2$ and $R^3$ together with the N atom to which they are attached form a saturated 5- or 6-membered ring optionally comprising one additional heteroatom selected from N, O or S, which ring may be substituted once or more than once with $R^4$;
$R^4$ is independently selected from $C_1$-$C_3$alkyl, di($C_1$-$C_3$alkyl)amino or two $R_4$ attached at the same carbon atom form an oxo group
for use in the treatment of solid malignancies characterized by positive FGFR4 and KLB expression, or positive FGFR4 and FGF19 expression, or positive FGFR4, KLB and FGF19 expression.

In an embodiment, the compound of formula (I), (Ia) or (Ia-1) used in the present invention is selected from
N-(5-cyanopyridin-2-yl)-7-formyl-3,4-dihydro-1,8-naphthyridine-1(2H)-carboxamide;
N-(5-cyanopyridin-2-yl)-7-formyl-6-(hydroxymethyl)-3,4-dihydro-1,8-naphthyridine-1(2H)-carboxamide;
N-(5-cyano-4-(2-methoxyethoxy)pyridin-2-yl)-7-formyl-6-(hydroxymethyl)-3,4-dihydro-1,8-naphthyridine-1(2H)-carboxamide;
(R)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide;
(S)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide;
N-(5-cyano-4-(2-methoxyethoxy)pyridin-2-yl)-6-(difluoromethyl)-7-formyl-3,4-dihydro-1,8-naphthyridine-1(2H)-carboxamide;
N-(5-cyanopyridin-2-yl)-7-formyl-6-((N-methylacetamido)methyl)-3,4-dihydro-1,8-naphthyridine-1(2H)-carboxamide;

N-(5-cyano-4-((2-methoxyethyl)amino)pyridin-2-yl)-7-formyl-6-(hydroxymethyl)-3,4-dihydro-1,8-naphthyridine-1(2H)-carboxamide;
N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide;
N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide;
N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide;
(R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide or pharmaceutically acceptable salts thereof.

In another embodiment of the present invention, there is provided N-(5-cyanopyridin-2-yl)-7-formyl-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided N-(5-cyanopyridin-2-yl)-7-formyl-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided N-(5-cyanopyridin-2-yl)-7-formyl-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided N-(5-cyanopyridin-2-yl)-7-formyl-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided N-(5-cyanopyridin-2-yl)-7-formyl-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided N-(5-cyanopyridin-2-yl)-7-formyl-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In another embodiment of the present invention, there is provided N-(5-cyanopyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided N-(5-cyanopyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided N-(5-cyanopyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided N-(5-cyanopyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided N-(5-cyanopyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided N-(5-cyanopyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In another embodiment of the present invention, there is provided N-(5-cyano-4-(2-methoxyethoxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided N-(5-cyano-4-(2-methoxyethoxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided N-(5-cyano-4-(2-methoxyethoxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided N-(5-cyano-4-(2-methoxyethoxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided N-(5-cyano-4-(2-methoxyethoxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided N-(5-cyano-4-(2-methoxyethoxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In another embodiment of the present invention, there is provided (R)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided (R)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided (R)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided (R)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided (R)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided (R)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In another embodiment of the present invention, there is provided (S)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided (S)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided (S)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided (S)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided (S)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided (S)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In another embodiment of the present invention, there is provided N-(5-cyano-4-(2-methoxyethoxy)pyridin-2-yl)-6-(difluoromethyl)-7-formyl-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided N-(5-cyano-4-(2-methoxyethoxy)pyridin-2-yl)-6-(difluoromethyl)-7-formyl-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided N-(5-cyano-4-(2-methoxyethoxy)pyridin-2-yl)-6-(difluoromethyl)-7-formyl-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided N-(5-cyano-4-(2-methoxyethoxy)pyridin-2-yl)-6-(difluoromethyl)-7-formyl-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided N-(5-cyano-4-(2-methoxyethoxy)pyridin-2-yl)-6-

(difluoromethyl)-7-formyl-3,4-dihydro-1,8-naphthyridine-1 (2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided N-(5-cyano-4-(2-methoxyethoxy)pyridin-2-yl)-6-(difluoromethyl)-7-formyl-3,4-dihydro-1,8-naphthyridine-1 (2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In another embodiment of the present invention, there is provided N-(5-cyanopyridin-2-yl)-7-formyl-6-((N-methylacetamido)methyl)-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided N-(5-cyanopyridin-2-yl)-7-formyl-6-((N-methylacetamido)methyl)-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided N-(5-cyanopyridin-2-yl)-7-formyl-6-((N-methylacetamido)methyl)-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided N-(5-cyanopyridin-2-yl)-7-formyl-6-((N-methylacetamido)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided N-(5-cyanopyridin-2-yl)-7-formyl-6-((N-methylacetamido)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided N-(5-cyanopyridin-2-yl)-7-formyl-6-((N-methylacetamido)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In another embodiment of the present invention, there is provided N-(5-cyano-4-((2-methoxyethyl)amino)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided N-(5-cyano-4-((2-methoxyethyl)amino)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided N-(5-cyano-4-((2-methoxyethyl)amino)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided N-(5-cyano-4-((2-methoxyethyl)amino)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided N-(5-cyano-4-((2-methoxyethyl)amino)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided N-(5-cyano-4-((2-methoxyethyl)amino)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In another embodiment of the present invention, there is provided N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided N-(5-cyano-4-((2-methoxyethyl)amino)pyridin-2-yl)-7-formyl-6-((4-methyl-2-oxopiperazin-1-yl)methyl)-3, 4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In another embodiment of the present invention, there is provided N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In another embodiment of the present invention, there is provided N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In another embodiment of the present invention, there is provided (R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided (R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and FGF19 expression.

In another embodiment of the present invention, there is provided (R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4, KLB and FGF19 expression.

In another embodiment of the present invention, there is provided (R)—N-(5-cyano-4-((1-methoxypropan-2-yl)oxy)

pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and KLB expression.

In another embodiment of the present invention, there is provided (R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4 and FGF19 expression.

In another embodiment of the present invention, there is provided (R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer, breast cancer, glioblastoma, prostate cancer, rhabdomyosarcoma, gastric cancer, ovarian cancer, lung cancer or colon cancer characterized by positive FGFR4, KLB and FGF19 expression.

In an embodiment of the invention, there is provided a compound of formula (I), (Ia) or (Ia-1) or a pharmaceutically acceptable salt thereof for use in treating a patient having solid malignancies, characterized in that the compound of formula (I) or a pharmaceutically acceptable salt thereof is to be administered to the patient on the basis of said patient having positive FGFR4 and KLB expression, or positive FGFR4 and FGF19 expression, or positive FGFR4, KLB and FGF19 expression.

In an embodiment of the invention, there is provided a compound of formula (I), (Ia) or (Ia-1) or a pharmaceutically acceptable salt thereof for use in treating a patient having solid malignancies, characterized in that
  a. The patient is selected for treatment with a compound of formula (I), (Ia) or (Ia-1) or a pharmaceutically acceptable salt thereof on the basis of the patient having positive FGFR4 and KLB expression, or positive FGFR4 and FGF19 expression, or positive FGFR4, KLB and FGF19 expression; and
  b. Thereafter, a compound of formula (I), (Ia) or (Ia-1) or a pharmaceutically acceptable salt thereof is administered to the patient.

In an embodiment of the invention, there is provided a compound of formula (I), (Ia) or (Ia-1) or a pharmaceutically acceptable salt thereof for use in treating a patient having solid malignancies, characterized in that
  a. A biological sample from a patient is assayed for positive FGFR4 and KLB expression, or positive FGFR4 and FGF19 expression, or positive FGFR4, KLB and FGF19 expression; and
  b. a compound of formula (I), (Ia) or (Ia-1) or a pharmaceutically acceptable salt thereof is administered to the patient on the basis of the biological sample from the patient having positive FGFR4 and KLB expression, or positive FGFR4 and FGF19 expression, or positive FGFR4, KLB and FGF19 expression.

In an embodiment of the invention, there is provided a compound of formula (I), (Ia) or (Ia-1) or a pharmaceutically acceptable salt thereof for use in treating a patient having solid malignancies comprising
  a. Assaying a biological sample from the patient
  b. Determining if the biological sample from the patient is characterized by positive FGFR4 and KLB expression, or by positive FGFR4 and FGF19 expression, or by positive FGFR4, KLB and FGF19 expression, and
  c. If the biological sample is characterized by positive FGFR4 and KLB expression, or by positive FGFR4 and FGF19 expression, or by positive FGFR4, KLB and FGF19 expression, administering a compound of formula (I), (Ia) or (Ia-1) or a pharmaceutically acceptable salt thereof to the patient.

In an embodiment, the invention relates to a method of treating a patient having solid malignancies characterized by positive FGFR4 and KLB expression comprising administering to said patient a therapeutically effective amount of a compound of the present invention or a pharmaceutically acceptable salt thereof.

In an embodiment, the invention relates to a method of treating a patient having solid malignancies characterized by positive FGFR4 and FGF19 expression comprising administering to said patient a therapeutically effective amount of a compound of the present invention or a pharmaceutically acceptable salt thereof.

In an embodiment, the invention relates to a method of treating a patient having solid malignancies characterized by positive FGFR4, KLB and FGF19 expression comprising administering to said patient a therapeutically effective amount of a compound of the present invention or a pharmaceutically acceptable salt thereof.

In an embodiment, the invention relates to a method of selectively treating a patient having solid malignancies, comprising selectively administering a therapeutically effective amount of a compound of the present invention or a pharmaceutically acceptable salt thereof to the patient on the basis of the patient having solid malignancies characterized by positive FGFR4 and KLB expression, or positive FGFR4 and FGF19 expression, or positive FGFR4, KLB and FGF19 expression.

In an embodiment, the invention relates to a method of selectively treating a patient having solid malignancies with a compound of the present invention or a pharmaceutically acceptable salt thereof comprising
  a) Selecting the patient for treatment with a compound of the present invention or a pharmaceutically acceptable salt thereof on the basis of the patient having positive FGFR4 and KLB expression, or positive FGFR4 and FGF19 expression, or positive FGFR4, KLB and FGF19 expression; and
  b) Thereafter, administering a therapeutically effective amount of a compound of the present invention or a pharmaceutically acceptable salt thereof to the patient.

In an embodiment, the invention relates to a method of selectively treating a patient having solid malignancies, comprising
  a) Assaying a biological sample from the patient for FGFR4 and KLB expression, or FGFR4 and FGF19 expression, or FGFR4, KLB and FGF19 expression
  b) Thereafter, selectively administering to the patient a therapeutically effective amount of a compound of the present invention or a pharmaceutically acceptable salt thereof on the basis of the biological sample from the patient having positive FGFR4 and KLB expression, or positive FGFR4 and FGF19 expression, or positive FGFR4, KLB and FGF19 expression.

In an embodiment, the invention relates to a method of selectively treating a patient having solid malignancies, comprising:

1) Assaying a biological sample from the patient for FGFR4 and KLB expression, or FGFR4 and FGF19 expression, or FGFR4, KLB and FGF19 expression;
2) Thereafter, selecting the patient for treatment with a compound of the present invention on the basis of the biological sample from the patient having positive FGFR4 and KLB expression, or positive FGFR4 and FGF19 expression, or positive FGFR4, KLB and FGF19 expression
3) Thereafter, administering a therapeutically effective amount of a compound of the present invention or a pharmaceutically acceptable salt thereof to the patient.

In an embodiment of the invention, the biological sample is selected from blood, plasma and tissue sample. In an embodiment of the invention, the positive expression of FGF19 is assayed from a blood sample. In an embodiment of the invention, the positive expression of FGF19 is assayed from a tissue sample. In an embodiment of the invention, the positive expression of FGFR4 or KLB is assayed from a tissue sample.

The methods of the invention include detecting expression of the biomarker gene product (i.e. FGFR4, KLB, FGF19 gene products) in a sample taken from a patient having solid malignancies and can be performed by detecting, for example, RNA transcribed from the biomarker gene such as mRNA, or polypeptides encoded by the biomarker gene. The level of expression of the biomarker can be used to predict whether a patient will likely respond to a compound as described herein. Those patients that have an increased level of expression of the biomarker compared to a control (referred to also herein as patients having a "positive expression of the biomarker") are selected for treatment with the compound described herein as it is predicted that such a patient has an increased likelihood of responding to such compounds.

Any appropriate sample of cells taken from a patient having solid malignancies can be used. Generally, the sample of cells or tissue sample will be obtained from the subject with solid malignancies by biopsy or surgical resection. In some instances, the sample taken from the patient having solid malignancies may be a blood sample. The sample of, for example tissue, may also be stored in, e.g., RNAlater (Ambion; Austin Tex.) or flash frozen and stored at −80° C. for later use. The biopsied tissue sample may also be fixed with a fixative, such as formaldehyde, paraformaldehyde, or acetic acid/ethanol. The fixed tissue sample may be embedded in wax (paraffin) or a plastic resin. The embedded tissue sample (or frozen tissue sample) may be cut into thin sections. RNA or protein may also be extracted from a fixed or wax-embedded tissue sample or a frozen tissue sample. Once a sample of cells or sample of tissue is removed from the subject with cancer, it may be processed for the isolation of RNA or protein using techniques well known in the art and as described below.

An example of extraction of RNA from a biopsy taken from a patient with solid malignancies can include, for example, guanidium thiocyanate lysis followed by CsCl centrifugation (Chirgwin, et al., Biochemistry 18:5294-5299, 1979). RNA from single cells may be obtained as described in methods for preparing cDNA libraries from single cells (see, e.g., Dulac, Curr. Top. Dev. Biol. 36:245, 1998; Jena, et al., J. Immunol. Methods 190:199, 1996). In one embodiment, the RNA population may be enriched for sequences of interest. Enrichment may be accomplished, for example, by random hexamers and primer-specific cDNA synthesis, or multiple rounds of linear amplification based on cDNA synthesis and template-directed in vitro transcription (see, e.g., Wang, et al., Proc. Natl. Acad. Sci. USA 86:9717, 1989; Dulac, et al., supra; Jena, et al., supra).

In one embodiment, the assaying method includes providing a nucleic acid probe comprising a nucleotide sequence, for example, at least 10, 15, 25 or 40 nucleotides, and up to all or nearly all of the coding sequence which is complementary to a portion of the coding sequence of a nucleic acid sequence of FGFR4, KLB and FGF19; obtaining a tissue sample from a mammal having a cancerous cell; contacting the nucleic acid probe under stringent conditions with RNA obtained from a biopsy taken from a patient (e.g., in a Northern blot, in situ hybridization assay, PCR etc); and determining the amount of hybridization of the probe with RNA. Nucleic acids may be labeled during or after enrichment and/or amplification of RNAs.

In the method of the invention, the step of assaying may comprise a technique as described below. Further examples of assaying are described in the examples.

The biomarkers FGFR4, KLB and FGF19 can be assayed using any method known in the art such as reverse Transcriptase PCR (RT-PCR). This method includes isolating mRNA using any technique known in the art, e.g., by using a purification kit, buffer set and protease from commercial manufacturers, such as Qiagen. The reverse transcription step is typically primed using specific primers, random hexamers, or oligo-dT primers, depending on the circumstances and the goal of expression profiling and the cDNA derived can then be used as a template in the subsequent PCR reaction. TaqMan® RT-PCR can then be performed using, e.g., commercially available equipment.

A more recent variation of the RT-PCR technique is the real time quantitative PCR, which measures PCR product accumulation through a dual-labeled fluorigenic probe (e.g., using TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al, Genome Research 6:986-994 (1996).

In another example, microarrays are used which include one or more probes corresponding to one or more of genes FGFR4, KLB and FGF19. The method includes the production of hybridization patterns of labeled target nucleic acids on the array surface. The resultant hybridization patterns of labeled nucleic acids may be visualized or detected in a variety of ways, with the particular manner of detection selected based on the particular label of the target nucleic acid. Representative detection means include scintillation counting, autoradiography, fluorescence measurement, calorimetric measurement, light emission measurement, light scattering, and the like.

In another example, a TaqMan® Low Density Array (TLDA) card can be used which can include one or more probes corresponding to one or more of genes FGFR4, KLB and FGF19. This method uses a microfluidic card that performs simultaneous real time PCR reactions.

In one example, the method of detection utilizes an array scanner that is commercially available (Affymetrix, Santa Clara, Calif.). The scanner is controlled from a system computer with an interface and easy-to-use software tools. The output may be directly imported into or directly read by a variety of software applications. Scanning devices are described in, for example, U.S. Pat. Nos. 5,143,854 and 5,424,186.

Once the level of expression of the biomarker is assayed it can be compared to a control. A control for comparison can be determined by one skilled in the art. In one example, a control is determined by choosing an expression value that serves as a cut-off value such that the value differentiates between those test samples that have increased biomarker expression, positive expression, from those that do not. In another example, the control can be a test sample taken from a healthy person or a sample such as a tumor sample where the biomarkers do not show expression or do not have increased expression above a normal/basal level.

In one example, the expression of each biomarker is measured and can be converted into an expression value after normalization by the expression level of a housekeeping gene. These expression values then can be used to generate a score which is then compared against a cut-off to select which subjects have positive biomarker expression and therefore are likely to benefit from treatment with compound as described herein.

Alternatively, the presence of a protein product encoded by the biomarkers can be assayed using any appropriate method known in the art and the level of protein product can be compared to a control. Exemplary immunoassays that may be conducted according to the invention include fluorescence polarization immunoassay (FPIA)$_5$ fluorescence immunoassay (FIA), enzyme immunoassay (EIA), nephelometric inhibition immunoassay (NIA), enzyme-linked immunosorbent assay (ELISA), and radioimmunoassay (RIA). An indicator moiety, or label group, may be attached to the subject antibodies and is selected so as to meet the needs of various uses of the method that are often dictated by the availability of assay equipment and compatible immunoassay procedures. General techniques to be used in performing the various immunoassays noted above are known to those of ordinary skill in the art. Alternatively, other methods can be used such as Western blot analysis that includes electrophoretically separating proteins on a polyacrylamide gel, and after staining the separated proteins, the relative amount of each protein can be quantified by assessing its optical density. Alternatively, other methods such as dot-blot assays, FACS or immunohistochemistry can be used.

Typically, antibodies generated against the biomarkers of the invention can be used for visualizing for the presence of a protein of interest and can be labeled, for example, using a reporter molecule such as fluorophores, enzymes, biotin, chemiluminescent molecules, bioluminescent molecules, digoxigenin, avidin, streptavidin or radioisotopes.

Those patients that are determined to have an increased level of biomarker protein product compared to a control are referred to herein as having positive biomarker expression.

In an embodiment of the invention, the solid malignancies are from a cancer selected from liver cancer, breast cancer, glioblastoma, prostate cancer, rhabdomyosarcoma, gastric cancer, ovarian cancer, lung cancer, colon cancer.

In an embodiment, the invention relates to a pharmaceutical composition comprising a compound of the present invention or a pharmaceutically acceptable salt thereof and one or more pharmaceutically acceptable carriers for use in the treatment of solid malignancies characterized by positive FGFR4 and KLB expression, or by positive FGFR4 and FGF19 expression, or by positive FGFR4, KLB and FGF19 expression.

In an embodiment, the invention relates to a method of treating cancer, comprising selectively administering a pharmaceutical composition comprising a compound of the present invention or a pharmaceutically acceptable salt thereof to a patient in need thereof on the basis of said patient having positive FGFR4 and KLB expression, or positive FGFR4 and FGF19 expression, or positive FGFR4, KLB and FGF19 expression.

In an embodiment of the invention, the cancer is selected from liver cancer, breast cancer, glioblastoma, prostate cancer, rhabdomyosarcoma, gastric cancer, ovarian cancer, lung cancer, colon cancer.

In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol;
c) binders, e.g., magnesium aluminum silicate, starch paste, gelatin, tragacanth, methylcellulose, sodium carboxymethylcellulose and/or polyvinylpyrrolidone;
d) disintegrants, e.g., starches, agar, alginic acid or its sodium salt, or effervescent mixtures; and
e) absorbents, colorants, flavors and sweeteners.

In an embodiment, the pharmaceutical compositions are capsules comprising the active ingredient only.

Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs, solutions or solid dispersion. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The pharmaceutical composition used in the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesise the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Abbreviations

| Abbreviation | Description |
| --- | --- |
| aq. | aqueous |
| conc. | concentrated |
| DAST | (diethylamino)sulfur trifluoride |
| dba | dibenzylideneacetone |
| DCM | dichloromethane |
| DIPEA | N,N-diisopropylethylamine, N-ethyl-N-isopropylpropan-2-amine |
| DMA | N,N-dimethylacetamide |
| DMAP | 4-dimethylaminopyridine |
| DMF | N,N-dimethylformamide |
| DMSO | dimethylsulfoxide |
| DMSO-$d_6$ | Hexadeuterodimethyl sulfoxide |
| dppf | 1,1'-bis(diphenylphosphino)ferrocene |
| DSC | Differential scanning calorimetry |
| ESI-MS | Electrospray ionization mass spectroscopy |
| h | hour |
| HPLC | High-performance liquid chromatography |
| KHMDS | Potassium hexamethyldisilazide |
| l/ml | litre/millilitre |
| LC-MS | liquid chromatography and mass spectrometry |
| LHMDS | Lithium hexamethyldisilazide |
| M | molar |
| min | minutes |
| mp | Melting point |
| MW | microwave |
| mw | Molecular weight |
| m/z | mass to charge ratio |
| NBS | N-bromosuccinimide |
| NIS | N-iodosuccinimide |
| NMP | N-methylpyrrolidinone, 1-methyl-2-pyrrolidinone |
| NMR | Nuclear magnetic resonance |
| org. | organic |
| RP | Reverse phase |
| sat | saturated |
| SFC | Supercritical fluid chromatography |
| TFA | trifluoroacetic acid |
| THF | tetrahydrofurane |
| $t_R$ or Rt | Retention time (if not indicated, in minutes) |
| UPLC | Ultra-performance liquid chromatography |

Analytical Details
NMR:

Measurements were performed on a Bruker Ultrashield™ 400 (400 MHz), Bruker Ultrashield™ 600 (600 MHz), 400 MHz DRX Bruker CryoProbe (400 MHz) or a 500 MHz DRX Bruker CryoProbe (500 MHz) spectrometer using or not trimethylsilane as an internal standard. Chemical shifts (d-values) are reported in ppm downfield from tetramethylsilane, spectra splitting pattern are designated as singlet (s), doublet (d), triplet (t), quartet (q), multiplet, unresolved or more overlapping signals (m), broad signal (br). Solvents are given in parentheses.

DSC:

DSC measurements were performed using a DSC Q2000 (TA Instruments, New Castle, Del., USA) equipped with a DSC Refrigerated Cooling System (TA Instruments, New Castle, Del., USA). Data were treated mathematically using the resident Universal Analysis® Software. Calibration for temperature and heat of fusion was carried out with indium as reference material. The samples were analyzed in open aluminium pans and scanned under a nitrogen purge with a heating rate of 10° C./min from 20 to 300° C.

UPLC-MS 1:
System: Waters Acquity UPLC with Waters SQ detector.
Column: Acquity HSS T3 1.8 μm 2.1×50 mm.
Flow: 1.2 ml/min. Column temperature: 50° C.
Gradient: from 2 to 98% B in 1.4 min, A=water+0.05% formic acid+3.75 mM ammonium acetate, B=acetonitrile+0.04% formic acid.

UPLC-MS 3:
System: Waters Acquity UPLC with Waters SQ detector.
Column: Acquity HSS T3 1.8 μm 2.1×50 mm.
Flow: 1.0 ml/min. Column temperature: 60° C.
Gradient: from 5 to 98% B in 1.4 min, A=water+0.05% formic acid+3.75 mM ammonium acetate, B=acetonitrile+0.04% formic acid.

UPLC-MS 6:
System: Waters Acquity Ultra Performance with Waters SQ detector.
Column: Acquity HSS T3 1.8 μm 2.1×50 mm.
Flow: 1.0 ml/min. Column temperature: 60° C.
Gradient: from 5 to 98% B in 1.4 min, A=water+0.05% formic acid+3.75 mM ammonium acetate, B=acetonitrile+0.04% formic acid.

UPLC-MS 7:
System: Waters Acquity Ultra Performance with Waters SQ detector.
Column: Acquity HSS T3 1.8 μm 2.1×50 mm.
Flow: 1.0 ml/min. Column temperature: 60° C.
Gradient: from 5 to 98% B in 1.4 min, A=water+0.05% formic acid+3.75 mM ammonium acetate, B=acetonitrile+0.04% formic acid.

Preparative Methods:
Flash Chromatography System:
System: Teledyne ISCO, CombiFlash Rf.
Column: pre-packed RediSep® Rf cartridges.
Samples were absorbed on Isolute, or on silica gel, or applied as solutions.

Supercritical Fluid Chromatography (SFC 1):
System: Waters SFC 100 prep-system with a Waters 2998 Photodiode Array (PDA) Detector and a
Waters 3100 Mass detector.
Column dimension: 250×30 mm.
Columns:

| Manufacturer | code | Name | Particle size | Pore size |
|---|---|---|---|---|
| Princeton | PPU | Propyl-pyridyl-urea | 5 μm | 100 Å |
| | 4EP | 4 Ethylpyridine | 5 μm | 60 Å |
| | DEAP | Diethylaminopropyl | 5 μm | 60 Å |
| Reprosil | NH2 | Amino | 5 μm | 100 Å |
| | DNH | Diamino | 5 μm | 100 Å |
| | SiOH | Silica | 5 μm | 100 Å |
| Waters | Hilic | Atlantis Silica OBD | 5 μm | 100 Å |

Flow: 100 ml/min 120 bar back pressure
Gradient: optimized gradient elution using supercritical $CO_2$/MeOH.

Reversed Phase HPLC (RP 4):
System: Gilson preparative HPLC system with UV-triggered collection system (254 nm).
Column: Sunfire Prep C18 OBD 5 μm 30×100 cm, temperature 25° C.

Gradient: gradient from 5-40% acetonitrile in water containing 0.1% TFA over 20 minutes, flow rate 30 ml/min.

Example 3: N-(5-cyanopyridin-2-yl)-7-formyl-3,4-dihydro-1,8-naphthyridine-1(2H)-carboxamide

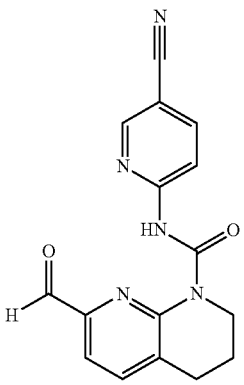 [SMILES: N#Cc1ccc(NC(=O)N2CCCc3ccc(C=O)nc32)nc1]

A solution of N-(5-cyanopyridin-2-yl)-7-(dimethoxymethyl)-3,4-dihydro-1,8-naphthyridine-1(2H)-carboxamide (intermediate 2, 150 mg, 0.424 mmol) in THF (3 ml) was treated with water (2.25 ml) and HCl conc. (0.75 ml). The reaction mixture was stirred for 15 min at room temperature. The reaction was quenched by addition of sat. aq. $NaHCO_3$ (gas evolution) and extracted with DCM (3×). The combined organic layers were washed with brine, dried over $Na_2SO_4$, filtered and concentrated under reduced pressure. The crude material was purified by normal phase chromatography (12 g silica gel cartridge, heptanes/EtOAc 100:0 to 0:100) to give the title compound as a white solid.

$^1$H NMR (400 MHz, DMSO-$d_6$) δ 13.86 (s, 1H), 9.96 (d, 1H), 8.80 (dd, 1H), 8.27 (dd, 1H), 8.22 (dd, 1H), 7.94 (d, 1H), 7.68 (d, 1H), 4.30-3.96 (m, 2H), 2.95 (t, 2H), 2.03-1.90 (m, 2H).

(UPLC-MS 1) $t_R$ 0.98 min; ESI-MS 308.1 $[M+H]^+$.

Intermediate 2: N-(5-cyanopyridin-2-yl)-7-(dimethoxymethyl)-3,4-dihydro-1,8-naphthyridine-1(2H)-carboxamide A solution of phenyl 7-(dimethoxymethyl)-3,4-dihydro-1,8-naphthyridine-1(2H)-carboxylate (intermediate 3, 262 mg, 0.798 mmol) and 2-amino-5-cyanopyridine (190 mg, 1.60 mmol) in THF (7.5 ml) at −15° C. under argon was treated drop wise with LHMDS (1 M in THF, 1.60 ml, 1.60 mmol). The reaction mixture was stirred at −15° C. for 25 min and then quenched by addition of sat. aq. $NH_4Cl$ and extracted with EtOAc (2×). The combined org. layers were washed with brine, dried over $Na_2SO_4$, filtered and concentrated under reduced pressure. The crude material was purified by normal phase chromatography (12 g silica gel cartridge, heptanes/EtOAc 100:0 to 0:100) to give the title compound as a white solid. (UPLC-MS 1) $t_R$ 1.09 min; ESI-MS 354.1 $[M+H]^+$.

Intermediate 3: phenyl 7-(dimethoxymethyl)-3,4-dihydro-1,8-naphthyridine-1(2H)-carboxylate A solution of 7-(dimethoxymethyl)-1,2,3,4-tetrahydro-1,8-naphthyridine (intermediate 4, 2 g, 9.60 mmol) and diphenylcarbonate (4.11 g, 19.21 mmol) in THF (40 ml) at −15°

C. was treated with LHMDS (1M in THF, 13.3 ml, 13.3 mmol) over 0.5 h. The reaction mixture was quenched with sat. aq. NH₄Cl, extracted with EtOAc (2×). The combined organic layers were washed with brine, dried over Na₂SO₄, filtered and concentrated under reduced pressure. The crude product was purified by normal phase chromatography (80 g silica gel cartridge, heptanes/EtOAc 100:0 to 25:75) to give the title compound as a pale yellow solid. ¹H-NMR (400 MHz, DMSO-d₆) δ 7.65 (d, 1H), 7.46-7.38 (m, 2H), 7.27-7.18 (m, 4H), 5.17 (s, 1H), 3.87-3.80 (m, 2H), 3.26 (s, 6H), 2.83 (t, 2H), 2.00-1.92 (m, 2H).

Intermediate 4: 7-(dimethoxymethyl)-1,2,3,4-tetra-hydro-1,8-naphthyridine

The procedure described in *J. Org. Chem.*, 2004, 69 (6), pp 1959-1966 was used. Into a 5-l pressure tank reactor (5 atm) was placed 2-(dimethoxymethyl)-1,8-naphthyridine (intermediate 5, 200 g, 979 mmol), ethanol (3 l), PtO₂ (12 g). The reactor was evacuated and flushed three times with nitrogen, followed by flushing with hydrogen. The mixture was stirred overnight at 23° C. under an atmosphere of hydrogen. This reaction was repeated four times. The solids were filtered out and the resulting mixture was concentrated under vacuum to give the title compound as a yellow solid.

¹H-NMR (400 MHz, DMSO-d₆) δ 7.14 (d, 1H), 6.51 (d, 1H), 6.47-6.41 (m, 1H), 4.98 (s, 1H), 3.28-3.19 (m, 2H), 3.23 (s, 6H), 2.64 (t, 2H), 1.73-1.79 (m, 2H).

Intermediate 5:
2-(dimethoxymethyl)-1,8-naphthyridine

The procedure described in *J. Org. Chem.*, 2004, 69 (6), pp 1959-1966 was used. Into a 20 l 4-necked round-bottom flask was placed 2-aminopyridine-3-carbaldehyde (1000 g, 8.19 mol), 1,1-dimethoxypropan-2-one (1257 g, 10.64 mol), ethanol (10 l), and water (2 l). This was followed by the addition of a solution of sodium hydroxide (409.8 g, 10.24 mol) in water (1000 ml) drop wise with stirring at 0-15° C. The solution was stirred for 3 h at 0-20° C. and then concentrated under vacuum. The resulting solution was extracted with 3×1200 ml of ethyl acetate and the organic layers were combined. The mixture was dried over sodium sulfate and concentrated under vacuum. The residue was washed with 3×300 ml of hexane and the solid was collected by filtration. This resulted in the title compound as a yellow solid. ¹H-NMR (400 MHz, DMSO-d₆) δ 9.11 (dd, 1H), 8.53 (d, 1H), 8.50 (dd, 1H), 7.73 (d, 1H), 7.67 (dd, 1H), 5.44 (s, 1H), 3.41 (s, 6H).

Example 27: N-(5-cyanopyridin-2-yl)-7-formyl-6-(hydroxymethyl)-3,4-dihydro-1,8-naphthyridine-1 (2H)-carboxamide

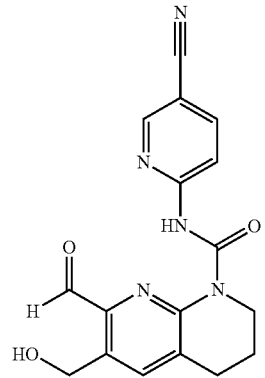

From intermediate 25, reacted in an analogous manner to the preparation of Example 18.

¹H NMR (400 MHz, DMSO-d₆) indicated a partially overlapping mixture of the title compound (minor) and the corresponding 5-membered ring lactol (Major) in a ~1:3.1 ratio as determined by integration of the signals at 13.93 and 13.48 ppm. Major: δ 13.48 (s, 1H), 8.77-8.74 (m, 1H), 8.31-8.20 (m, 2H), 7.73 (s, 1H), 7.05 (d, 1H), 6.19 (d, 1H), 5.09-5.01 (m, 1H), 4.95-4.87 (m, 1H), 4.06-3.88 (m, 2H), 2.88 (t, 2H), 2.02-1.86 (m, 2H); minor: 13.93 (s, 1H), 10.09 (s, 1H), 8.82-8.78 (m, 1H), 8.31-8.20 (m, 2H), 8.06-8.01 (m, 1H), 5.51 (t, 1H), 4.95-4.87 (m, 2H), 4.06-3.88 (m, 2H), 2.98 (t, 2H), 2.02-1.86 (m, 2H).

(UPLC-MS 3) $t_R$ 0.81, 0.86; ESI-MS 338.1, 338.1 [M+H]⁺.

Intermediate 25: N-(5-cyanopyridin-2-yl)-7-(dimethoxymethyl)-6-(hydroxymethyl)-3,4-dihydro-1,8-naphthyridine-1(2H)-carboxamide To a solution of 6-bromo-N-(5-cyanopyridin-2-yl)-7-(dimethoxymethyl)-3,4-dihydro-1,8-naphthyridine-1(2H)-carboxamide (intermediate 2H, 171 mg, 0.396 mmol) in THF (5 ml) at −78° C., was added MeLi (1.6 M in Et₂O, 0.247 ml, 0.396 mmol), the solution was stirred for 5 min. Then, n-BuLi (1.6 M in hexane, 0.272 ml, 0.435 mmol) was added and the solution was stirred for 20 min. Then, DMF (0.184 ml, 2.37 mmol) was added. The reaction mixture was stirred at −78° C. for 1.5 h and then allowed to warm to room temperature. The reaction mixture was poured into sat. aq. NH₄Cl and extracted twice with DCM. The organic phase was then dried over Na₂SO₄, filtered and evaporated. The residue was purified by normal phase chromatography (12 g gold silica gel cartridge, heptanes/EtOAc 100:0 to 0:100). The N-(5-cyanopyridin-2-yl)-7-(dimethoxymethyl)-6-formyl-3,4-dihydro-1,8-naphthyridine-1(2H)-carboxamide containing fraction were concentrated. The residue was dissolved in MeOH (1.5 ml) and DCM (1.5 ml) and treated with NaBH₄ (5.32 mg, 0.141 mmol). The reaction mixture was stirred at room temperature for 30 min, then poured into sat. aq. NH₄Cl and extracted with DCM (3×). The combined organic phases were then dried over Na₂SO₄, filtered and evaporated. The crude material was purified by normal phase chromatography (4 g silica gel cartridge, heptanes/EtOAc 100:0 to 0:100) followed by a reverse phase chromatography (13 g C18 cartridge, 0.1% TFA in water/acetonitrile 80:20 to 0:100). The product containing fractions were treated with sat. aq. Na₂CO₃, concentrated until the organic solvent had been removed extracted with DCM (3×). The combined organic layers were dried over Na₂SO₄, filtered and evaporated to give the title compound as a colorless resin. (UPLC-MS 3) $t_R$ 0.92 min; ESI-MS 384.1 [M+H]⁺.

Reference Example 18: 7-formyl-6-(hydroxymethyl)-N-(5-(trifluoromethyl)pyridin-2-yl)-3,4-dihydro-1,8-naphthyridine-1(2H)-carboxamide

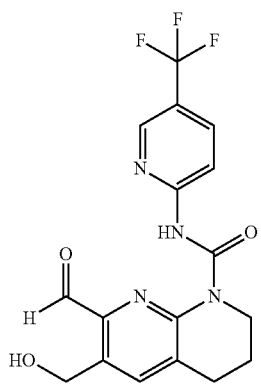 [SMILES: O=Cc1nc2c(cc1CO)CCCN2C(=O)Nc1ccc(C(F)(F)F)cn1]

A solution of 7-(dimethoxymethyl)-6-(hydroxymethyl)-N-(5-(trifluoromethyl)pyridin-2-yl)-3,4-dihydro-1,8-naphthyridine-1(2H)-carboxamide (intermediate 14, 18 mg, 0.042 mmol) in THF (0.8 ml) was treated with water (0.6 ml) and conc. HCl (0.2 ml) and stirred for 15 min. The reaction mixture was quenched by addition of sat. aq. NaHCO₃ (gas evolution), extracted with DCM (3×). The combined organic layers were dried over anhydrous Na₂SO₄, filtered and concentrated under reduced pressure. The crude material was triturated with EtOAc/heptanes 10:1, filtered and dried under vacuum to give the title compound as a white solid.

¹H NMR (400 MHz, DMSO-d₆) indicated a partially overlapping mixture of the title compound (Minor) and the corresponding 5-membered ring lactol (Major) in a ~1:2.1 ratio as determined by integration of the signals at 13.87 and 13.38 ppm. δ Major: 13.38 (s, 1H), 8.69-8.66 (m, 1H), 8.28 (d, 1H), 8.19 (td, 1H), 7.73 (s, 1H), 7.02 (d, 1H), 6.19 (dd, 1H), 5.09-5.01 (m, 1H), 4.94-4.87 (m, 1H), 4.06-3.89 (m, 2H), 2.89 (t, 2H), 2.00-1.88 (m, 2H); Minor: 13.87 (s, 1H), 10.11 (s, 1H), 8.75-8.72 (m, 1H), 8.28 (d, 1H), 8.19 (td, 1H), 8.03 (s, 1H), 5.50 (t, 1H), 4.94-4.87 (m, 2H), 4.06-3.89 (m, 2H), 2.98 (t, 2H), 2.00-1.88 (m, 2H).

(UPLC-MS 1) $t_R$ 0.97, 1.05; ESI-MS 381.1, 381.1 [M+H]⁺.

Reference Intermediate 14: 7-(dimethoxymethyl)-6-(hydroxymethyl)-N-(5-(trifluoromethyl)pyridin-2-yl)-3,4-dihydro-1,8-naphthyridine-1(2H)-carboxamide A solution of 6-bromo-7-(dimethoxymethyl)-N-(5-(trifluoromethyl)pyridin-2-yl)-3,4-dihydro-1,8-naphthyridine-1(2H)-carboxamide (intermediate 2D, 100 mg, 0.210 mmol) in THF (2 ml) at −78° C. under argon was treated drop wise with n-BuLi (1.5 M in hexane, 0.309 ml, 0.463 mmol). The resulting brown solution was stirred for 2 min and then DMF (0.1 ml, 1.29 mmol) was added. The resulting yellow solution was stirred at −78° C. for 15 min. The reaction mixture was quenched by addition of sat. aq. NH₄Cl, warmed to room temperature and extracted with EtOAc (2×). The combined organic layers were washed with brine, dried over Na₂SO₄, filtered and concentrated under reduced pressure. The residue was purified by normal phase chromatography (12 g silica gel cartridge, heptanes/EtOAc 100:0 to 0:100) the 7-(dimethoxymethyl)-6-formyl-N-(5-(trifluoromethyl)pyridin-2-yl)-3,4-dihydro-1,8-naphthyridine-1(2H)-carboxamide containing fractions were concentrated to give a white solid. This material was dissolved in MeOH (2 ml) and DCM (1 ml), treated at room temperature with NaBH₄ (6.36 mg, 0.168 mmol) and stirred for 0.5 h. The reaction mixture was quenched with sat. aq. NH₄Cl and extracted with DCM (3×). The combined organic layers were dried over Na₂SO₄, filtered and concentrated under reduced pressure. The crude material was purified by normal phase chromatography (12 g silica gel cartridge, heptanes/EtOAc 100:0 to 0:100) the product containing fractions were concentrated to give the title compound as a white solid. (UPLC-MS 1) $t_R$ 1.10 min; ESI-MS 421.0 [M+H]⁺.

Reference Intermediate 2D: 6-bromo-7-(dimethoxymethyl)-N-(5-(trifluoromethyl)pyridin-2-yl)-3,4-dihydro-1,8-naphthyridine-1(2H)-carboxamide From intermediate 11 and 5-(trifluoromethyl)pyridin-2-amine, reacted in an analogous manner to the preparation of intermediate 2. ¹H NMR (400 MHz, DMSO-d₆) δ ppm 13.56 (s, 1H) 8.70-8.75 (m, 1H) 8.26 (d, 1H) 8.16 (dd, 1H) 7.99 (s, 1H) 5.59 (s, 1H) 3.91-3.98 (m, 2H) 3.39 (s, 6H) 2.85 (t, 2H) 1.86-1.96 (m, 2H).

Intermediate 11: phenyl 6-bromo-7-(dimethoxymethyl)-3,4-dihydro-1,8-naphthyridine-1(2H)-carboxylate A solution of 6-bromo-7-(dimethoxymethyl)-1,2,3,4-tetrahydro-1,8-naphthyridine (intermediate 12, 2.28 g, 7.94 mmol) and diphenylcarbonate (2.13 g, 9.93 mmol) in THF (40 ml) at −17° C. was treated drop wise over 5 min with LHMDS (1M in THF, 8.34 ml, 8.34 mmol). The yellow reaction mixture was stirred for 30 min, quenched with sat. aq. NH₄Cl and extracted with EtOAc (2×). The combined organic layers were washed with brine, dried over Na₂SO₄, filtered and concentrated under reduced pressure. The crude was purified by normal phase chromatography (80 g silica gel cartridge, heptanes/EtOAc 100:0 to 0:100) to give the title compound as a white solid. ¹H NMR (400 MHz, DMSO-d₆) δ 7.94 (s, 1H) 7.37-7.45 (m, 2H) 7.19-7.28 (m, 3H) 5.46 (s, 1H) 3.80-3.87 (m, 2H) 3.29 (s, 6H) 2.84 (t, 2H) 1.90-2.00 (m, 2H).

Reference Intermediate 12: 6-bromo-7-(dimethoxymethyl)-1,2,3,4-tetrahydro-1,8-naphthyridine Into a 3 l 4-necked round-bottom flask was placed 7-(dimethoxymethyl)-1,2,3,4-tetrahydro-1,8-naphthyridine (intermediate 4, 114.6 g, 550.3 mmol) in acetonitrile (2 l). This was followed by the addition of NBS (103 g, 578 mol) in portions with stirring at 25° C. The resulting solution was stirred for 30 min at 25° C. The resulting mixture was concentrated under vacuum and the residue was diluted with 1000 ml of diethylether. The mixture was washed with 3×100 ml of ice/water. The aqueous phase was extracted with 2×100 ml of diethylether and the organic layers were combined. The resulting mixture was washed with 1×100 ml of brine, dried over sodium sulfate and concentrated under vacuum to give the title compound as a light yellow solid. LC-MS: (ES, m/z): 286.03 [M+H]⁺. ¹H-NMR: (300 MHz, CDCl₃) δ 1.86-1.94 (2H, m), 2.70-2.74 (2H, m), 3.9-3.43 (2H, m), 3.47 (6H, s), 5.23 (1H, s), 5.58 (1H, s), 7.29 (1H, s).

Example 39: N-(5-cyano-4-(2-methoxyethoxy)pyridin-2-yl)-7-formyl-6-(hydroxymethyl)-3,4-dihydro-1,8-naphthyridine-1(2H)-carboxamide

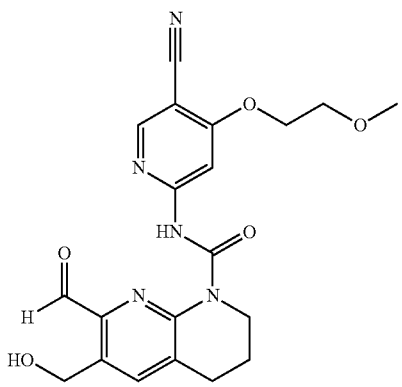 [SMILES: COCCOc1cc(NC(=O)N2CCCc3cc(CO)c(C=O)nc32)ncc1C#N]

To a solution of 6-(((tert-butyldimethylsilyl)oxy)methyl)-N-(5-cyano-4-(2-methoxyethoxy)pyridin-2-yl)-7-(dimethoxymethyl)-3,4-dihydro-1,8-naphthyridine-1(2H)-carboxamide (intermediate 37, 98 mg, 0.171 mmol) in THF (1 ml) and H₂O (1 ml) was added conc. HCl (0.5 ml), the reaction mixture was stirred at room temperature for 6 h. The reaction mixture was poured into sat. aq. NaHCO₃ and extracted with DCM (2×). The organic phase was then dried over Na₂SO₄, filtered and evaporated. Trituration of the crude material in EtOAc/heptanes followed by drying under vacuum furnished the title compound as a colorless powder.

¹H NMR (400 MHz, DMSO-d₆) indicated a partially overlapping mixture of the title compound (Minor) and the corresponding 5-membered ring lactol (Major) in a ~1:2.8 ratio as determined by integration of the signals at 13.90 and 13.42 ppm. δ Major: 13.42 (s, 1H), 8.55 (s, 1H), 7.97 (s, 1H), 7.73 (s, 1H), 7.02-7.10 (m, 1H), 6.14-6.23 (m, 1H), 5.05 (dd, 1H), 4.86-4.94 (m, 1H) 4.29-4.38 (m, 2H), 3.88-4.03 (m, 2H), 3.71-3.77 (m, 2H), 2.88 (t, 2H), 1.86-2.00 (m, 2H). Minor: 13.90 (s, 1H), 10.07 (s, 1H), 8.60 (s, 1H), 8.04 (s, 1H), 7.95 (s, 1H), 5.51 (t, 1H), 4.86-4.94 (m, 2H), 4.29-4.38 (m, 2H), 3.88-4.03 (m, 2H), 3.71-3.77 (m, 2H), 2.98 (t, 2H), 1.86-2.00 (m, 2H).

(UPLC-MS 3) $t_R$ 0.87, 0.91; ESI-MS 412.2, 412.2 [M+H]⁺.

Intermediate 37: 6-(((tert-butyldimethylsilyl)oxy)methyl)-N-(5-cyano-4-(2-methoxyethoxy)pyridin-2-yl)-7-(dimethoxymethyl)-3,4-dihydro-1,8-naphthyridine-1(2H)-carboxamide To a solution of phenyl 6-(((tert-butyldimethylsilyl)oxy)methyl)-7-(dimethoxymethyl)-3,4-dihydro-1,8-naphthyridine-1(2H)-carboxylate (intermediate 38, 206 mg, 0.436 mmol) and 6-amino-4-(2-methoxyethoxy)nicotinonitrile (intermediate 20, 93 mg, 0.479 mmol) in THF (3 ml) at −78° C. was slowly added LHMDS (1 M in THF, 0.959 ml, 0.959 mmol). The reaction mixture was stirred at −78° C. for 30 min, then allowed to warm to room temperature. The reaction mixture was poured into sat. aq. NH₄Cl and extracted twice with DCM. The organic phase was then dried over Na₂SO₄, filtered and evaporated. The crude material was purified by normal phase chromatography (12 g silica gel cartridge, heptanes/EtOAc 100:0 to 50:50) followed by reverse phase chromatography (43 g C18 cartridge, 0.1% TFA in water/acetonitrile 90:10 to 0:100) to give the title compound as an off-white solid. (UPLC-MS 3) $t_R$ 1.59 min; ESI-MS 572.3 [M+H]⁺.

Intermediate 38: phenyl 6-(((tert-butyldimethylsilyl)oxy)methyl)-3,4-dihydro-1,8-naphthyridine-1(2H)-carboxylate To a solution of 6-(((tert-butyldimethylsilyl)oxy)methyl)-7-(dimethoxymethyl)-1,2,3,4-tetrahydro-1,8-naphthyridine (intermediate 39, 8.49 g, 24.1 mmol) and diphenyl carbonate (5.42 g, 25.3 mmol) in THF (130 ml) at −78° C. was added slowly LHMDS (1 M in THF, 25.3 ml, 25.3 mmol). The reaction mixture was stirred at −78° C. for 30 min, then allowed to warm to room temperature. The reaction mixture was poured into sat. aq. NH₄Cl and extracted twice with DCM. The combined organic phases were then dried over Na₂SO₄, filtered and concentrated. The crude material was purified by normal phase chromatography (330 g silica gel cartridge, heptanes/EtOAc 100:0 to 50:50) to give the title compound as a light yellow oil. ¹H NMR (400 MHz, DMSO-d₆) δ 7.68 (s, 1H), 7.37-7.45 (m, 2H), 7.19-7.27 (m, 3H), 5.17 (s, 1H), 4.84 (s, 2H), 3.80-3.86 (m, 2H), 3.27 (s, 6H), 2.84 (t, 2H), 1.91-2.02 (m, 2H), 0.91 (s, 9H), 0.08 (s, 6H).

Intermediate 39: 6-(((tert-butyldimethylsilyl)oxy)methyl)-7-(dimethoxymethyl)-1,2,3,4-tetrahydro-1,8-naphthyridine To a solution of (2-(dimethoxymethyl)-5,6,7,8-tetrahydro-1,8-naphthyridin-3-yl)methanol (intermediate 40, 6.5 g, 27.3 mmol) in DCM (100 ml) and DMF (25 ml) at 0° C. were added DIPEA (7.15 ml, 40.9 mmol), tert-butylchlorodimethylsilane (4.93 g, 32.7 mmol) and DMAP (0.067 g, 0.546 mmol). The reaction mixture was then stirred for 1 h at room temperature, then poured into sat. aq. NaHCO₃ and extracted twice with DCM. The combined organic phases were dried over Na₂SO₄, filtered and evaporated. The crude material was purified by normal phase chromatography (120 g silica gel cartridge, heptanes/EtOAc 95:5 to 0:100) to give the title compound as a light yellow oil which solidified upon standing to give an off-white powder. (UPLC-MS 3) $t_R$ 1.10 min; ESI-MS 353.3 [M+H]⁺.

Intermediate 40: (2-(dimethoxymethyl)-5,6,7,8-tetrahydro-1,8-naphthyridin-3-yl)methanol To a solution of 2-(dimethoxymethyl)-5,6,7,8-tetrahydro-1,8-naphthyridine-3-carbaldehyde (intermediate 41, 10 g, 38.2 mmol) in MeOH (120 ml) and DCM (60 ml) was added NaBH₄ (1.16 g, 30.6 mmol). The reaction mixture was stirred at room temperature for 30 min, then slowly quenched with sat. aq. NH₄Cl and concentrated until the organic solvents had been mostly removed. The resulting mixture was extracted with DCM (4×). The combined organic phases were dried over Na₂SO₄, filtered and evaporated. The crude material was purified by normal phase chromatography (330 g silica gel cartridge, DCM/(DCM/

MeOH 9/1) 100:0 to 45:55) to give the title compound as a yellow oil. (UPLC-MS 3) $t_R$ 0.38 min; ESI-MS 239.2 [M+H]$^+$.

Intermediate 41: 2-(dimethoxymethyl)-5,6,7,8-tetrahydro-1,8-naphthyridine-3-carbaldehyde To a solution of 6-bromo-7-(dimethoxymethyl)-1,2,3,4-tetrahydro-1,8-naphthyridine (intermediate 12, 15.0 g, 52.2 mmol) in THF (400 ml) at −78° C. under argon, was added MeLi (1.6 M in Et$_2$O, 32.6 ml, 52.2 mmol), the solution was stirred for 5 min, then n-BuLi (1.6 M in hexane, 35.9 ml, 57.5 mmol) was added slowly and the solution was stirred for 20 min. THF (100 ml) was added to the reaction at −78° C. Subsequently, n-BuLi (1.6 M in hexane, 49.0 ml, 78 mmol) was added and the reaction mixture was stirred for 20 min, then again n-BuLi (1.6 M in hexane, 6.53 ml, 10.45 mmol) was added and the mixture was stirred for 10 min at −78° C. DMF (2.10 ml, 27.2 mmol) was added and the reaction mixture was stirred at −78° C. for 45 min, then it was allowed to warm to room temperature, poured into sat. aq. NH$_4$Cl and extracted twice with DCM. The combined organic phases were dried over Na$_2$SO$_4$, filtered and evaporated to give the title compound as an orange oil. (UPLC-MS 3) $t_R$ 0.63 min; ESI-MS 237.2 [M+H]$^+$.

Intermediate 12: 6-bromo-7-(dimethoxymethyl)-1,2,3,4-tetrahydro-1,8-naphthyridine Into a 3 l 4-necked round-bottom flask was placed 7-(dimethoxymethyl)-1,2,3,4-tetrahydro-1,8-naphthyridine (intermediate 4, 114.6 g, 550.3 mmol) in acetonitrile (2 l). This was followed by the addition of NBS (103 g, 578 mol) in portions with stirring at 25° C. The resulting solution was stirred for 30 min at 25° C. The resulting mixture was concentrated under vacuum and the residue was diluted with 1000 ml of diethylether. The mixture was washed with 3×100 ml of ice/water. The aqueous phase was extracted with 2×100 ml of diethylether and the organic layers were combined. The resulting mixture was washed with 1×100 ml of brine, dried over sodium sulfate and concentrated under vacuum to give the title compound as a light yellow solid. LC-MS: (ES, m/z): 286.03 [M+H]$^+$. $^1$H-NMR: (300 MHz, CDCl$_3$) δ 1.86-1.94 (2H, m), 2.70-2.74 (2H, m), 3.9-3.43 (2H, m), 3.47 (6H, s), 5.23 (1H, s), 5.58 (1H, s), 7.29 (1H, s).

Intermediate 20: 6-amino-4-(2-methoxyethoxy)nicotinonitrile

A solution of KHMDS in THF (1M, 48.1 ml, 48.1 mmol) was added to a solution of 2-methoxy ethanol (1.68 g, 21.88 mmol) in THF (90 ml) at room temperature. After 2 minutes 6-amino-4-fluoronicotinonitrile (intermediate 21, 3.00 g, 21.9 mmol) was added and the reaction mixture stirred for 16 h at room temperature. The reaction mixture was partitioned between saturated aqueous NH$_4$Cl and EtOAc, extracted with EtOAc (2×), the combined EtOAc layers were washed with brine, dried over MgSO$_4$ and evaporated. The residue was triturated with EtOAc and the title compound obtained by filtration as a beige solid. $^1$H NMR (400 MHz, DMSO-d$_6$) δ 8.14 (s, 1H), 6.91 (s, br, 2H), 6.03 (s, 1H), 4.19-4.13 (m, 2H), 3.34-3.28 (m, 2H), 2.51 (s, 3H).

Intermediate 21: 6-amino-4-fluoronicotinonitrile 4-fluoro-5-iodopyridin-2-amine (intermediate 22, 240 g, 1 mol), zinc cyanide (125 g, 1.05 mol), zinc (13 g, 0.2 mol), Pd$_2$(dba)$_3$ (25 g, 25 mmol) and dppf (55 g, 0.1 mol) in DMA (800 ml) were degassed and charged into the round bottom flask under nitrogen. The mixture was stirred at 100° C. for 3 h. The reaction mixture was diluted with 5% NaHCO$_3$ (2 l), extracted with EtOAc (4×600 ml). The combined organic layers were washed with 5% NaOH (1 l), dried over Na$_2$SO$_4$, concentrated to 700 ml. The resulting organic phase was eluted through silica gel column with EtOAc (1.7 l). The combined organic filtrate was washed with 2 M HCl (3×800 ml). The pH of the aqueous phase was adjusted to 10 with saturated NaHCO$_3$. The aqueous phase was extracted whit DCM (3×500 ml). The combined DCM was dried over Na$_2$SO$_4$ and concentrated. The residue was further purified by column chromatography (eluted with pentane: EtOAc 10:1 to 3:2) followed by recrystallization from pentane/EtOAc 3/1 to give the title compound as white solid. $^1$H NMR (400 MHz, DMSO-d$_6$) δ 8.40 (d, 1H), 7.40 (s, 2H), 6.34 (d, 1H).

Intermediate 22: 4-fluoro-5-iodopyridin-2-amine

A suspension of 4-fluoropyridin-2-amine (336 g, 2.5 mol) and NIS (745 g, 2.75 mol) in MeCN (9 l) was treated with TFA (114 g, 1 mol). The reaction mixture was then stirred at room temperature for 8 h. The reaction mixture was diluted with EtOAc (10 l), washed with sat. aq. Na$_2$S$_2$O$_3$ (2×5 l), brine (4×5 l). The combined organic layers were dried over Na$_2$SO$_4$, filtered and concentrated to get the crude product. The crude product was purified by recrystallization from EtOAc/pentane (1/10) to afford the title compound as a white solid. $^1$H NMR (400 MHz, DMSO-d$_6$) δ 8.14 (d, 1H), 6.45 (s, 2H), 6.33 (d, 1H).

Example 49: (R)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide

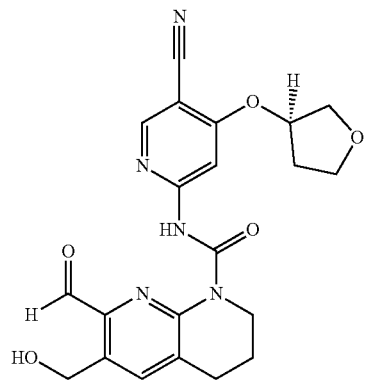 [SMILES: N#Cc1cnc(NC(=O)N2CCCc3cc(CO)c(C=O)nc32)cc1O[C@@H]1CCOC1]

From intermediate 37H, reacted in an analogous manner to the preparation of Example 39.

(UPLC-MS 3) $t_R$ 0.85, 0.90; ESI-MS 424.2, 424.2 [M+H]$^+$.

Intermediate 37H: (R)-6-(((tert-butyldimethylsilyl)oxy)methyl)-N-(5-cyano-4-((tetrahydrofuran-3-yl)oxy)pyridin-2-yl)-7-(dimethoxymethyl)-3,4-dihydro-1,8-naphthyridine-1(2H)-carboxamide From intermediates 38 and 47, reacted in an analogous manner to the preparation of intermediate 37. (UPLC-MS 3) $t_R$ 1.59 min; ESI-MS 584.3 [M+H]$^+$.

Intermediate 47: (R)-6-amino-4-((tetrahydrofuran-3-yl)oxy)nicotinonitrile (R)-tetrahydrofuran-3-ol (161 mg, 1.82 mmol) was treated at room temperature with KHMDS (1 M in THF, 1.09 ml, 1.09 mmol). The reaction mixture was stirred for 2 min. Then, the mixture was added to a solution of 6-amino-4-fluoronicotinonitrile (intermediate 21, 50 mg, 0.365 mmol) in NMP (0.5 ml). The resulting dark brown solution was stirred at room temperature for 1 h 50 min. The reaction mixture was quenched with sat. aq. NH$_4$Cl and extracted 2× with EtOAc. The combined organic layers were dried over Na$_2$SO$_4$, filtered and concentrated. The crude material was purified by normal phase chromatography (4 g silica gel cartridge, DCM/(DCM/(1 M NH$_3$ in MeOH) 9/1) 100:0 to 0:100) to give the title compound as a brown solid. (UPLC-MS 3) $t_R$ 0.48 min; ESI-MS 206.1 [M+H]$^+$.

Example 50: (S)—N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide

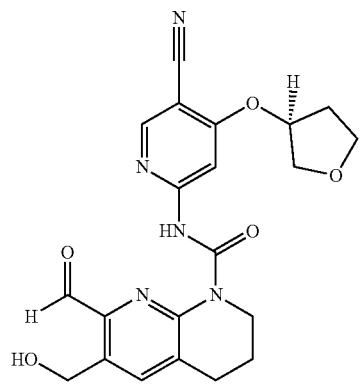 [SMILES: N#Cc1cnc(NC(=O)N2CCCc3cc(CO)c(C=O)nc32)cc1O[C@H]1CCOC1]

From intermediate 37I, reacted in an analogous manner to the preparation of Example 39.

(UPLC-MS 3) $t_R$ 0.85, 0.89; ESI-MS 424.2, 424.2 [M+H]$^+$.

Intermediate 37I: (S)-6-(((tert-butyldimethylsilyl)oxy)methyl)-N-(5-cyano-4-((tetrahydrofuran-3-yl)oxy)pyridin-2-yl)-7-(dimethoxymethyl)-3,4-dihydro-1,8-naphthyridine-1(2H)-carboxamide From intermediates 38 and 47, reacted in an analogous manner to the preparation of intermediate 37. (UPLC-MS 3) $t_R$ 1.59 min; ESI-MS 584.3 [M+H]$^+$.

Example 63: N-(5-cyano-4-(2-methoxyethoxy)pyridin-2-yl)-6-(difluoromethyl)-7-formyl-3,4-dihydro-1,8-naphthyridine-1(2H)-carboxamide

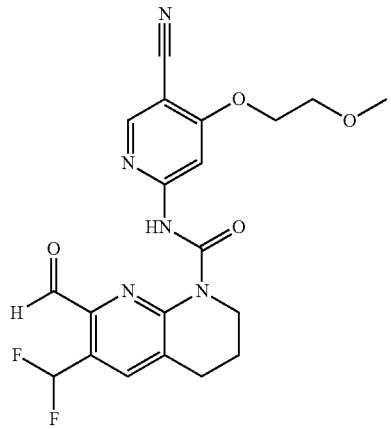 [SMILES: COCCOc1cc(NC(=O)N2CCCc3cc(C(F)F)c(C=O)nc32)ncc1C#N]

From intermediate 37L, reacted in an analogous manner to the preparation of Example 3.

$^1$H NMR (400 MHz, DMSO-d$_6$) δ 13.66 (s, 1H), 10.01 (s, 1H), 8.62 (s, 1H), 8.17 (s, 1H), 7.94 (s, 1H), 7.57 (t, 1H), 4.33-4.39 (m, 2H), 3.97-4.05 (m, 2H), 3.72-3.78 (m, 2H), 3.35 (s, 3H), 3.01 (t, 2H), 1.93-2.03 (m, 2H).

(UPLC-MS 3) $t_R$ 1.16; ESI-MS 432.2 [M+H]$^+$.

Intermediate 37L: N-(5-cyano-4-(2-methoxyethoxy)pyridin-2-yl)-6-(difluoromethyl)-7-(dimethoxymethyl)-3,4-dihydro-1,8-naphthyridine-1(2H)-carboxamide From intermediates 54 and 20, reacted in an analogous manner to the preparation of intermediate 37. (UPLC-MS 3) $t_R$ 1.25 min; ESI-MS 478.2 [M+H]$^+$.

Intermediate 54: phenyl 6-(difluoromethyl)-7-(dimethoxymethyl)-3,4-dihydro-1,8-naphthyridine-1(2H)-carboxylate To a solution of phenyl 7-(dimethoxymethyl)-6-formyl-3,4-dihydro-1,8-naphthyridine-1(2H)-carboxylate (intermediate 51B, 100 mg, 0.281 mmol) in DCM (2.5 ml) was added DAST (0.185 ml, 1.40 mmol), the solution was stirred at room temperature for 2 h, then DAST (0.037 ml, 0.281 mmol) was added and the reaction mixture was stirred for 1 h. The reaction mixture was poured into sat. aq. NaHCO$_3$ and extracted twice with DCM. The organic phase was then dried over Na$_2$SO$_4$, filtered and evaporated. The crude material was purified by normal phase chromatography (4 g silica gel cartridge, heptanes/EtOAc 95:5 to 50:50) to give the title compound as a yellow resin.

(UPLC-MS 3) $t_R$ 1.19 min; ESI-MS 379.5 [M+H]$^+$.

An alternative synthesis of phenyl 6-(difluoromethyl)-7-(dimethoxymethyl)-3,4-dihydro-1,8-naphthyridine-1(2H)-carboxylate is outlined below:

A solution of LHMDS in THF (1.6M, 6.64 ml, 10.63 mmol) was added drop wise to a solution of 6-(difluoromethyl)-7-(dimethoxymethyl)-1,2,3,4-tetrahydro-1,8-naphthyridine (intermediate 101, 1.7 g, 6.25 mmol) and diphenylcarbonate (1.41 g, 6.57 mmol) in THF (20 ml) at −78° C. The reaction mixture was stirred for 30 minutes at −78° C., then for 18 h at room temperature, partitioned between saturated aqueous NH₄Cl and DCM, extracted DCM (2×), dried over Na₂SO₄ and evaporated. The residue was preabsorbed onto isolute and purified by normal phase chromatography using a 40 g RediSep® silica column, eluting with a gradient from heptane to 50% EtOAc in heptane. Product containing fractions were combined and evaporated to give the title compound as a white solid.

(UPLC-MS 7) $t_R$ 1.19 min; ESI-MS 379.4 [M+H]$^+$.

Intermediate 51B: phenyl 7-(dimethoxymethyl)-6-formyl-3,4-dihydro-1,8-naphthyridine-1(2H)-carboxylate From intermediate 41 reacted in an analogous manner to the preparation of intermediate 51.

(UPLC-MS 3) $t_R$ 1.08 min; ESI-MS 357.2 [M+H]$^+$.

Reference Intermediate 51: phenyl 7-(dimethoxymethyl)-6-iodo-3,4-dihydro-1,8-naphthyridine-1(2H)-carboxylate A solution of 7-(dimethoxymethyl)-6-iodo-1,2,3,4-tetrahydro-1,8-naphthyridine (intermediate 52, 97 mg, 0.290 mmol) and diphenyl carbonate (74.6 mg, 0.348 mmol) in THF (2.5 ml) at −78° C. was treated with LHMDS (1 M in THF, 0.334 ml, 0.334 mmol) and stirred for 2 h. The reaction was then allowed to warm to room temperature over 20 min, quenched by addition of sat. aq. NH₄Cl and extracted with DCM (2×). The organic layer was dried over Na₂SO₄, filtered and concentrated. The crude material was purified by normal phase chromatography (12 g silica gel cartridge, heptanes/EtOAc 100:0 to 0:100) to give the title compound as a white solid. (UPLC-MS 3) $t_R$ 1.19 min; ESI-MS 455.1 [M+H]$^+$.

Reference Intermediate 52: 7-(dimethoxymethyl)-6-iodo-1,2,3,4-tetrahydro-1,8-naphthyridine A solution of 7-(dimethoxymethyl)-1,2,3,4-tetrahydro-1,8-naphthyridine (intermediate 4, 1 g, 4.8 mmol) in MeCN (15 ml) was treated with NIS (1.13 g, 5.04 mmol), stirred for 4 h in a flask covered with aluminum foil. Them, the reaction mixture was concentrated. The residue was treated with Et₂O and DCM, washed with water (2×) and brine, dried over Na₂SO₄, filtered and concentrated. The crude material was purified by normal phase chromatography (80 g silica gel cartridge, heptanes/EtOAc 100:0 to 0:100) to give the title compound as a yellow oil. (UPLC-MS 3) $t_R$ 0.73 min; ESI-MS 335.3 [M+H]$^+$.

Example 68: N-(5-cyanopyridin-2-yl)-7-formyl-6-((N-methylacetamido)methyl)-3,4-dihydro-1,8-naphthyridine-1(2H)-carboxamide

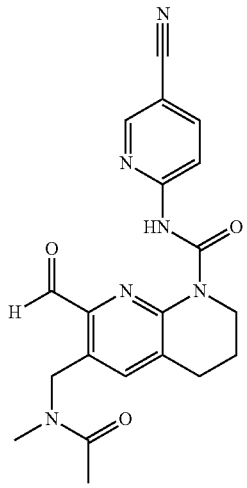 [SMILES: CC(=O)N(C)Cc1cc2c(nc1C=O)N(C(=O)Nc1ccc(C#N)cn1)CCC2]

From intermediate 59, reacted in an analogous manner to the preparation of Example 3.

¹H NMR (400 MHz, DMSO-d₆) δ 13.91 (s, 0.75H), 13.89 (s, 0.25H), 10.12 (s, 0.75H), 10.09 (s, 0.25H), 8.85-8.78 (m, 1H), 8.31-8.19 (m, 2H), 7.58 (s, 0.75H), 7.55 (s, 0.25H), 4.95 (s, 0.5H), 4.87 (s, 1.5H), 4.04-3.94 (m, 2H), 3.02-2.91 (m, 4.25H), 2.83 (s, 0.75H), 2.12 (s, 2.25H), 2.00-1.89 (m, 2.75H). 3:1 mixture of romaters.

(UPLC-MS 3) $t_R$ 0.91; ESI-MS 393.2 [M+H]$^+$.

Intermediate 59: N-(5-cyanopyridin-2-yl)-7-(dimethoxymethyl)-6-((N-methylacetamido)methyl)-3,4-dihydro-1,8-naphthyridine-1(2H)-carboxamide To a solution of N-(5-cyanopyridin-2-yl)-7-(dimethoxymethyl)-6-((methylamino)methyl)-3,4-dihydro-1,8-naphthyridine-1(2H)-carboxamide (intermediate 60, 14.5 mg, 0.037 mmol) in DCM (0.5 ml) was added Et₃N (10.2 μl, 0.073 mmol) and acetic anhydride (6.9 μl, 0.073 mmol). The reaction mixture was stirred at room temperature for 30 min, poured into sat. aq. NaHCO₃ and extracted with DCM (2×). The organic phase was then dried over Na₂SO₄, filtered and concentrated. The crude material was purified by normal phase chromatography (4 g silica gel cartridge, DCM/(DCM/MeOH 9/1) 100:0 to 0:100) to give the title compound as an off-white solid. (UPLC-MS 3) $t_R$ 0.98 min; ESI-MS 439.3 [M+H]$^+$.

Intermediate 60: N-(5-cyanopyridin-2-yl)-7-(dimethoxymethyl)-6-((methylamino)methyl)-3,4-dihydro-1,8-naphthyridine-1(2H)-carboxamide A tube was charged with methylamine hydrochloride (7.79 mg, 0.115 mmol) followed by methylamine (2 M in MeOH, 0.058 ml, 0.115 mmol) and NaCNBH₃ (14.5 mg, 0.231 mmol). Then, a suspension of N-(5-cyanopyridin-2-yl)-7-(dimethoxymethyl)-6-formyl-3,4-dihydro-1,8-naphthyridine-1(2H)-carboxamide (intermediate 36, 22 mg, 0.058 mmol) in MeOH (1 ml) was added, the tube was sealed and the reaction mixture was stirred at 70° C. for 1 h. The reaction mixture was quenched with water and concentrated until the organic solvents had mostly been removed. Water was added and the mixture was extracted with DCM (3×). The organic phase was then dried over $Na_2SO_4$, filtered and evaporated. The crude material was purified by normal phase chromatography (4 g silica gel cartridge, DCM/(DCM/(7 M $NH_3$ in MeOH) 9/1) 100:0 to 50:50) to give the title compound as a yellow resin. (UPLC-MS 3) $t_R$ 0.72 min; ESI-MS 397.3 $[M+H]^+$.

Intermediate 36: N-(5-cyanopyridin-2-yl)-7-(dimethoxymethyl)-6-formyl-3,4-dihydro-1,8-naphthyridine-1(2H)-carboxamide To a solution of 6-bromo-N-(5-cyanopyridin-2-yl)-7-(dimethoxymethyl)-3,4-dihydro-1,8-naphthyridine-1(2H)-carboxamide (intermediate 2H, 300 mg, 0.694 mmol) in THF (10 ml) at −78° C., was added MeLi (1.6 M in $Et_2O$, 0.434 ml, 0.694 mmol), the solution was stirred for 5 min, then n-BuLi in (1.6 M in hexane, 0.477 ml, 0.763 mmol) was added and the solution was stirred for 20 min. Then, DMF (0.322 ml, 4.16 mmol) was added, the reaction mixture was stirred at −78° C. for 1 h and then allowed to warm to room temperature. The reaction mixture was poured into sat. aq. $NH_4Cl$ and extracted twice with DCM. The combined organic phase was then dried over $Na_2SO_4$, filtered and evaporated. The crude material was purified by normal phase chromatography (40 g gold silica gel cartridge, heptanes/EtOAc 95:5 to 0:100) to give the title compound as a colorless powder.
(UPLC-MS 3) $t_R$ 1.10 min; ESI-MS 382.2 $[M+H]^+$.

Intermediate 2H: 6-bromo-N-(5-cyanopyridin-2-yl)-7-(dimethoxymethyl)-3,4-dihydro-1,8-naphthyridine-1(2H)-carboxamide From intermediate 11 and 2-amino-5-cyanopyridine, reacted in an analogous manner to the preparation of intermediate 2. (UPLC-MS 1) $t_R$ 1.18 min, ESI-MS 432.0, 434.0 $[M+H]^+$.

Example 80: N-(5-cyano-4-((2-methoxyethyl)amino)pyridin-2-yl)-7-formyl-6-(hydroxymethyl)-3,4-dihydro-1,8-naphthyridine-1(2H)-carboxamide

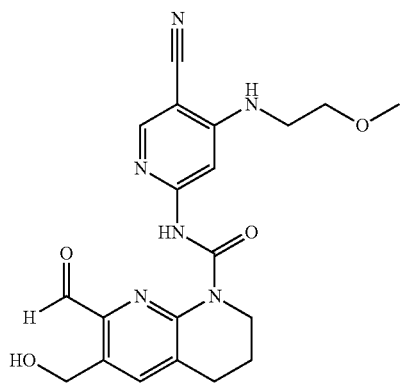 [SMILES: COCCNc1cc(NC(=O)N2CCCc3cc(CO)c(C=O)nc32)ncc1C#N]

A solution of 6-(((tert-butyldimethylsilyl)oxy)methyl)-N-(5-cyano-4-((2-methoxyethyl)amino)pyridin-2-yl)-7-(dimethoxymethyl)-3,4-dihydro-1,8-naphthyridine-1(2H)-carboxamide (intermediate 74, 3.10 g, 5.43 mmol) in THF (40 ml) was treated with $H_2O$ (30 ml) followed by dropwise addition of conc. HCl (10 ml) and stirred for 40 min. The reaction mixture was quenched by addition of sat. aq. $NaHCO_3$ (gas evolution) and then extracted with DCM (3×). The combined organic layers were washed with brine, dried over anhydrous $Na_2SO_4$, filtered and concentrated under reduced pressure. The residue was treated with EtOAc (25 ml) and sonicated until a white suspension was obtained. Then, heptanes (25 ml) was added and the resulting suspension was filtered. The solid was washed with heptanes and dried under vacuum to give the title compound as a white solid.
$^1$H NMR (400 MHz, DMSO-$d_6$) indicated a partially overlapping mixture of the title compound (Minor) and the corresponding 5-membered ring lactol (Major) in a ~1:2.5 ratio as determined by integration of the signals at 13.52 and 13.01 ppm. δ Major: 13.01 (s, 1H), 8.22 (s, 1H), 7.70 (s, 1H), 7.54 (s, 1H), 7.01 (d, 1H), 6.91 (t, 1H), 6.16 (dd, 1H), 5.04 (dd, 1H), 4.92-4.85 (m, 1H), 4.01-3.87 (m, 2H), 3.56-3.50 (m, 2H), 3.43-3.35 (m, 2H), 3.30-3.28 (m, 3H), 2.87 (t, 2H), 2.00-1.83 (m, 2H); Minor: 13.52 (s, 1H), 10.05 (s, 1H), 8.26 (s, 1H), 8.02 (s, 1H), 7.52 (s, 1H), 6.96 (t, 1H), 5.47 (t, 1H), 4.92-4.85 (m, 2H), 4.01-3.87 (m, 2H), 3.56-3.50 (m, 2H), 3.43-3.35 (m, 2H), 3.30-3.28 (m, 3H), 2.96 (t, 2H), 2.00-1.83 (m, 2H).
(UPLC-MS 3) $t_R$ 0.82, ESI-MS 411.2, $[M+H]^+$.

Intermediate 74: 6-(((tert-butyldimethylsilyl)oxy)methyl)-N-(5-cyano-4-((2-methoxyethyl)amino)pyridin-2-yl)-7-(dimethoxymethyl)-3,4-dihydro-1,8-naphthyridine-1(2H)-carboxamide A solution of phenyl 6-(((tert-butyldimethylsilyl)oxy)methyl)-7-(dimethoxymethyl)-3,4-dihydro-1,8-naphthyridine-1(2H)-carboxylate (intermediate 38, 2.98 g, 6.29 mmol) and 6-amino-4-((2-methoxyethyl)amino)nicotinonitrile (intermediate 75, 1.10 g, 5.72 mmol) in THF (45 ml) at −70° C. (dry ice/2-PrOH bath, internal temperature) under argon was treated with LHMDS (1 M in THF, 12.6 ml, 12.6 mmol). The resulting solution was stirred with cooling for 35 min. The cooling bath was then removed and the reaction mixture was allowed to warm to −25° C., before being re-cooled to −70° C. The resulting solution was quenched with sat. aq. $NH_4Cl$, allowed to warm to room temperature and extracted twice with EtOAc/heptanes 1:1. The combined organic layers were washed with brine, dried over $Na_2SO_4$, filtered and concentrated under reduced pressure. The crude material was purified by normal phase chromatography (80 g silica gel cartridge, heptanes/EtOAc 100:0 to 0:100). The product containing fractions were concentrated and dried under vacuum to give the title compound as a white solid. (UPLC-MS 3) $t_R$ 1.60; ESI-MS 571.4 $[M+H]^+$.
$^1$H NMR (400 MHz, $CDCl_3$-d) δ 13.81 (s, 1H), 8.23 (s, 1H), 7.74 (s, 1H), 7.57 (s, 1H), 5.45 (s, 1H), 5.26 (br s, 1H), 4.87 (s, 2H), 4.07-3.99 (m, 2H), 3.63 (t, 2H), 3.52-3.38 (m, 11H), 2.86 (t, 2H), 2.05-1.94 (m, 2H), 0.95 (s, 9H), 0.12 (s, 6H).

Intermediate 75: 6-amino-4-((2-methoxyethyl)amino)nicotinonitrile

A solution of 6-amino-4-fluoronicotinonitrile (intermediate 21, 1.10 g, 8.02 mmol) in DMA (20 ml) was treated with 2-methoxyethylamine (2.07 ml, 24.1 mmol) and DIPEA (4.20 mL, 24.1 mmol), heated to 50° C. and stirred for 15 h. The reaction mixture was cooled to room temperature and concentrated. The crude material was purified by normal phase chromatography (24 g silica gel cartridge, heptanes/EtOAc 100:0 to 0:100). The product containing fractions were concentrated and dried under vacuum to give the title compound as an off-white solid.

An alternative synthesis of 6-amino-4-((2-methoxyethyl)amino)nicotinonitrile is outlined below: To tert-butyl N-{5-cyano-4-[(2-methoxyethyl)amino]pyridin-2-yl}carbamate (intermediate 287, 7 g) was added 30-36% aqueous HCl (40 ml), the mixture stirred at room temperature for 30 minutes and monitored by chromatography until complete conversion. The solution was then basified with 20-30% NaOH solution to pH=9-10 and filtered to give a white solid. The solid was added to ethyl acetate (15 ml) and heated to 50-55° C. to form a clear solution. The solution was then cooled to 3-6° C., stirred for 2-3 h and filtered. The wet cake was then dried to give the title compound as a white solid. $^1$H NMR (400 MHz, DMSO-$d_6$) δ 7.92 (s, 1H), 6.39 (s, 2H), 6.15 (t, 1H), 5.61 (s, 1H), 3.46 (t, 2H), 3.27 (s, 3H), 3.24 (q, 2H). (UPLC-MS 3) $t_R$ 0.62; ESI-MS 193.1 [M+H]$^+$.

Example 83: N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide

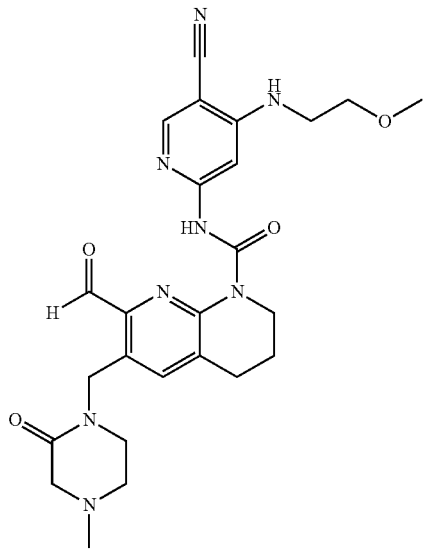 [SMILES: COCCNc1cc(NC(=O)N2CCCc3cc(CN4CCN(C)CC4=O)c(C=O)nc32)ncc1C#N]

Concentrated hydrochloric acid (0.40 ml) was added to a solution of N-(5-cyano-4-((2-methoxyethyl)amino)pyridin-2-yl)-7-(dimethoxymethyl)-6-((4-methyl-2-oxopiperazin-1-yl)methyl)-3,4-dihydro-1,8-naphthyridine-1(2H)-carboxamide (intermediate 80, 470 mg, 0.808 mmol) in THF (3 ml) and water (1 ml) at room temperature. After stirring for 3 h at room temperature saturated aqueous NaHCO$_3$ was added, the mixture extracted with DCM (3×), the organic layers dried over Na$_2$SO$_4$ and evaporated. The residue was sonicated with EtOAc (6 ml) and pentane (6 ml) and then filtered. The white solid obtained was then dissolved in DCM (6 ml), EtOAc added (3 ml), the solution warmed, sealed and allowed to stand at room temperature for 2 h. Filtration and drying gave the title compound as a white solid.
$^1$H NMR (400 MHz, DMSO-$d_6$) δ 13.43 (s, 1H), 10.06 (s, 1H), 8.24 (s, 1H), 7.49 (s, 1H), 7.47 (s, 1H), 6.96 (t, br, 1H), 4.86 (s, 2H), 3.96-3.90 (m, 2H), 3.52-3.46 (m, 2H), 3.39-3.33 (m, 2H), 3.30-3.21 (m, 2H), 3.37 (s, 3H), 3.02 (s, 2H), 2.93-2.86 (m, 2H), 2.61-2.56 (m, 2H), 2.21 (s, 3H), 1.95-1.85 (m, 2H).
(UPLC-MS 6) $t_R$ 0.70, ESI-MS 507.2, [M+H]$^+$.

The following salts were prepared from the above free base form of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide by precipitation with the appropriate counterions.

Malate with 1:1 stoichiometry (mw 640.66), mp (DSC) 181.1° C. (onset): Acetone (2 ml) was added to a mixture of malic acid (26.4 mg, 0.197 mmol) and N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg, 0.197 mmol) and the mixture heated on a mini-block with heating-cooling cycles from 55 to 5° C. for 7 repeat cycles (heating rate: 1.5° C./min, cooling rate: 0.25° C./min). The white solid was collected by centrifugation and dried for 18 h at 40° C. to give the title salt.

Tartrate with 1:0.5 stoichiometry (mw 581.72), mp (DSC) 176.7° C. (onset). A solution of tartaric acid (75.7 mg) in methanol (5 ml) was prepared at room temperature (0.1 M). A portion of the 0.1 M tartaric acid in acetone solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in methanol (4 ml) and the mixture sonicated for 1 minute then heated at 55° C. with stirring for 2 h. The white solid was then collected by filtration, washing 2× with methanol (2 ml), and dried for 18 h at 40° C. under vacuum to give the title salt.

Tartrate with 1:1 stoichiometry (mw 656.66), mp (DSC) 169.9° C. (onset): A solution of tartaric acid (75.7 mg) in acetone (5 ml) was prepared at room temperature (0.1 M). A portion of the 0.1 M tartaric acid in acetone solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in methanol (4 ml) and the mixture sonicated for 1 minute then heated at 55° C. with stirring for 2 h. The white solid was then collected by filtration, washing 2× with acetone (2 ml), and dried for 18 h at 40° C. under vacuum to give the title salt.

Citrate with 1:0.5 stoichiometry (mw 602.73), mp (DSC) 168.4° C. (onset): A solution of citric acid (96.9 mg) in acetone (5 ml) was prepared at room temperature (0.1 M). A portion of the 0.1 M citric acid in acetone solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in methanol (4 ml) and the mixture sonicated for 1 minute then heated at 55° C. with stirring for 2 h. The white solid was then collected by filtration, washing 2× with acetone (2 ml), and dried for 18 h at 40° C. under vacuum to give the title salt.

Citrate with 1:1 stoichiometry (mw 698.70), mp (DSC) 168.8° C. (onset): A solution of citric acid (96.9 mg) in acetone (5 ml) was prepared at room temperature (0.1 M). A portion of the 0.1 M citric acid in acetone solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in acetone (4 ml) and the mixture sonicated for 1 minute then heated at 55° C. with stirring for 2 h before slowly cooling to room temperature. The white solid was then collected by filtration, washing 2× with acetone (2 ml), and dried for 18 h at 40° C. under vacuum to give the title salt.

Alternatively, N-(5-cyano-4-((2-m ethoxyethyl)amino) pyridin-2-yl)-7-formyl-6-((4-methyl-2-oxopiperazin-1-yl) methyl)-3,4-dihydro-1,8-naphthyridine-1(2H)-carboxamide (6.5 g, 12.83 mmol) was placed in a 500 ml 4-flask reactor. 49 ml of glacial acetic acid was added and the resulting suspension was stirred at 23° C. until a clear mixture was obtained. In a separate flask, anhydrous 2-hydroxypropane-1,2,3-tricarboxylic acid (2.59 g, 13.47 mmol, 1.05 equiv.) was dissolved in 49 ml of glacial acetic acid at 50° C. until a clear solution was obtained. This solution was then added at 23° C. to the N-(5-cyano-4-((2-methoxyethyl)amino)pyridin-2-yl)-7-formyl-6-((4-methyl-2-oxopiperazin-1-yl) methyl)-3,4-dihydro-1,8-naphthyridine-1(2H)-carboxamide solution previously prepared. This mixture was stirred for 30 min at 23° C. and then added dropwise over 1 h to 192 ml of ethyl acetate warmed to 75° C. The temperature remained constant over the addition. At the end of the addition, the temperature of the mixture was cooled slowly to 23° C. and let 16 h at this temperature under gentle stirring. The suspension was cooled to 5-10° C. and filtered. The cake was washed with 15 ml of ethyl acetate and 15 ml of acetone. The wet cake (ca 8.5 g) was transferred in a 500 ml flask containing 192 ml of dry acetone. The resulting suspension was refluxed for 24 h. The suspension was filtered and the cake was washed with 2 times 15 ml of dry acetone then dried at 50° C. under vacuum for several hours to give the title salt.

Intermediate 80: N-(5-cyano-4-((2-methoxyethyl) amino)pyridin-2-yl)-7-(dimethoxymethyl)-6-((4-methyl-2-oxopiperazin-1-yl)methyl)-3,4-dihydro-1, 8-naphthyridine-1(2H)-carboxamide A solution of 6-amino-4-((2-methoxyethyl)amino)nicotinonitrile (intermediate 75, 481 mg, 2.50 mmol) in anhydrous DMF (1.5 ml) was added drop wise over 10 minutes to a mixture of di(1H-1,2,4-triazol-1-yl)methanone (410 mg, 2.50 mmol) and DMF (1.5 ml) cooled at 0° C. After stirring for 45 minutes at 0° C. the reaction mixture was allowed to warm to room temperature and after a further 90 minutes at room temperature a solution of 1-((2-(dimethoxymethyl)-5,6,7,8-tetrahydro-1,8-naphthyridin-3-yl)methyl)-4-methyl-piperazin-2-one (intermediate 81, 418 mg, 1.00 mmol) in DMF (2 ml) was added. The reaction mixture was stirred for 17.5 h at room temperature, quenched by the addition of MeOH and evaporated. The residue was applied to a 80 g RediSep® silica column as a DCM solution and purified by normal phase chromatography, eluting with a gradient from DCM to 2% MeOH in DCM. Product containing fractions were combined and evaporated to give the title compound as an orange foam. $^1$H NMR (400 MHz, DMSO-d$_6$) δ 13.50 (s, 1H), 8.27 (s, 1H), 7.52 (s, 1H), 7.39 (s, 1H), 6.93 (t, 1H), 5.45 (s, 1H), 4.65 (s, 2H), 3.94-3.89 (m, 2H), 3.54-3.50 (m, 2H), 3.40-3.35 (m, 2H), 3.38 (s, 6H), 3.29 (s, 3H), 3.20-3.16 (m, 2H), 3.05 (s, 2H), 2.86-2.80 (m, 2H), 2.61-2.55 (m, 2H), 2.22 (s, 3H), 1.94-1.88 (m, 2H). (UPLC-MS 6) $t_R$ 0.72; ESI-MS 553.3 [M+H]$^+$.

Example 92: N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide

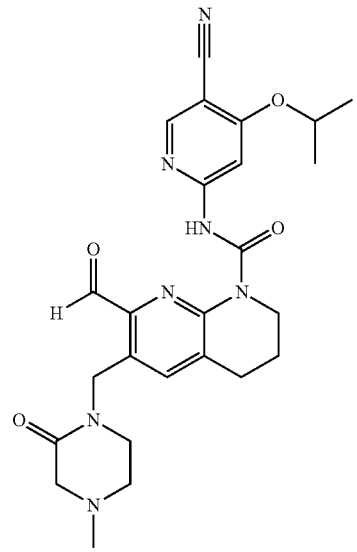 [SMILES: CC(C)Oc1cc(NC(=O)N2CCCc3cc(CN4CCN(C)CC4=O)c(C=O)nc32)ncc1C#N]

Concentrated hydrochloric acid (0.15 ml) was added to a solution of N-(5-cyano-4-isopropoxypyridin-2-yl)-7-(dimethoxymethyl)-6-((4-methyl-2-oxopiperazin-1-yl)methyl)-3,4-dihydro-1,8-naphthyridine-1(2H)-carboxamide (intermediate 95, 188 mg, 0.301 mmol) in THF (1.1 ml) and water (0.4 ml) at room temperature. After stirring for 4 h at room temperature the reaction was assessed to be complete by HPLC/MS and saturated aqueous NaHCO$_3$ was added, the mixture extracted with DCM (3×), the organic layers dried over Na$_2$SO$_4$ and evaporated. The crude residue was sonicated with EtOAc (6 ml) and pentane (6 ml) and then filtered. The white solid obtained was then heated and sonicated with EtOAc added (3 ml). Filtration of the cooled suspension and drying gave the title compound as a white solid.

$^1$H NMR (400 MHz, DMSO-d$_6$) δ 13.78 (s, 1H), 10.09 (s, 1H), 8.55 (s, 1H), 7.91 (s, 1H), 7.52 (s, 1H), 4.86 (s, 2H), 4.83 (septet, 1H), 3.99-3.95 (m, 2H), 3.30-3.25 (m, 2H), 3.04 (s, 2H), 2.94-2.90 (m, 2H), 2.61-2.56 (m, 2H), 2.21 (s, 3H), 1.96-1.88 (m, 2H), 1.36 (d, 6H).

(UPLC-MS 6) recorded in MeOH, $t_R$ 0.83 and 0.88, ESI-MS 492.3 and 534.3, [M+H]$^+$ and [M+MeOH+H]$^+$.

The following salts were prepared from the above free base form of N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide by precipitation with the appropriate counterions.

Tartrate salt with 1:1 stoichiometry (mw 641.63): A solution of L-(+)-tartaric acid in acetone (0.1 M, 2.03 ml, 0.203 mmol) was added to a suspension of N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide (100 mg, 0.203 mmol) in acetone (5 ml) at room temperature. The mixture was warmed to 55° C., maintained at this temperature for 3 h and cooled slowly to room temperature. The white precipitate that formed was washed with acetone and dried to give the title compound.

$^1$H NMR (600 MHz, DMSO-d$_6$) δ 13.80 (s, 1H), 10.11 (s, 1H), 8.59 (s, 1H), 7.95 (s, 1H), 7.56 (s, 1H), 4.91 (s, 2H), 4.86 (septet, 1H), 4.30 (s, 2H), 4.00-3.95 (m, 2H), 3.31-3.26 (m, 2H), 3.08 (s, 2H), 2.96-2.91 (m, 2H), 2.67-2.62 (m, 2H), 2.26 (s, 3H), 1.97-1.89 (m, 2H), 1.40 (d, 6H).

Tosylate salt with 1:1 stoichiometry (mw 663.75): A solution of tosic acid in acetone (0.1 M, 2.03 ml, 0.203 mmol) was added to a suspension of N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide (100 mg, 0.203 mmol) in acetone (5 ml) at room temperature. The mixture was warmed to 55° C., maintained at this temperature for 3 h and cooled slowly to room temperature. The solution was allowed to stand open to the air for 18 h and the precipitate that formed was washed with acetone and dried to give the title compound. H NMR (600 MHz, DMSO-$d_6$) δ 13.81 (s, 1H), 10.10 (s, 1H), 8.59 (s, 1H), 7.95 (s, 1H), 7.68 (s, 1H), 7.48 (d, 2H), 7.12 (d, 2H), 4.97 (s, 2H), 4.86 (septet, 1H), 4.02-3.98 (m, 2H), 3.58-3.53 (br, m, 2H), 3.41 (br, s, 2H), 2.96-2.92 (m, 2H), 2.91 (br, s, 2H), 2.51 (s, 3H), 2.29 (s, 3H), 1.98-1.90 (m, 2H), 1.41 (d, 6H).

Citrate salt with 1:1 stoichiometry (mw 683.68): A solution of citric acid in acetone (0.1 M, 2.03 ml, 0.203 mmol) was added to a suspension of N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide (100 mg, 0.203 mmol) in DCM (2 ml) at room temperature. The mixture was warmed with a bath at 65° C., maintained at this temperature for 10 min and slowly cooled to 5° C. The white precipitate that formed was collected, acetone (5 ml) and EtOH (1 ml) were added and the mixture heated at 50° C. for 3 h. The mixture was cooled to 5° C., filtered and dried to give the title compound.

$^1$H NMR (600 MHz, DMSO-$d_6$) δ 13.82 (s, 1H), 10.11 (s, 1H), 8.59 (s, 1H), 7.95 (s, 1H), 7.57 (s, 1H), 4.91 (s, 2H), 4.86 (septet, 1H), 4.01-3.97 (m, 2H), 3.33-3.28 (m, 2H), 3.14 (s, 2H), 2.97-2.93 (m, 2H), 2.74 (d, 2H), 2.72-2.67 (m, 2H), 2.65 (d, 2H), 2.30 (s, 3H), 1.99-1.91 (m, 2H), 1.40 (d, 6H).

Intermediate 95: N-(5-cyano-4-isopropoxypyridin-2-yl)-7-(dimethoxymethyl)-6-((4-methyl-2-oxopiperazin-1-yl)methyl)-3,4-dihydro-1,8-naphthyridine-1(2H)-carboxamide A mixture of 1-((2-(dimethoxymethyl)-5,6,7,8-tetrahydro-1,8-naphthyridin-3-yl)methyl)-4-methylpiperazin-2-one (intermediate 81, 268 mg, 0.641 mmol), phenyl (5-cyano-4-isopropoxypyridin-2-yl)carbamate (intermediate 96, 834 mg, 1.122 mmol) and DMAP (7.83 mg, 0.064 mmol) in acetonitrile (2.6 ml) was heated at reflux for 3.5 h. The reaction mixture was evaporated and applied to a 24 g RediSep silica column as a DCM solution and purified by normal phase chromatography, eluting with a gradient from DCM to 10% MeOH in DCM. Product containing fractions were combined and evaporated to give the title compound as an off-white solid.

(UPLC-MS 6) $t_R$ 0.92; ESI-MS 538.7 [M+H]$^+$.

Intermediate 96: phenyl (5-cyano-4-isopropoxypyridin-2-yl)carbamate

Phenyl chloroformate (3.89 ml, 31.0 mmol) was added drop wise to a mixture of 6-amino-4-isopropoxynicotinonitrile (intermediate 97, 2.5 g, 14.11 mmol) and pyridine (2.51 ml, 31.0 mmol) in THF (100 ml) at room temperature. The reaction mixture was stirred for 12 h at room temperature, additional pyridine (2.51 ml, 31.0 mmol) added, before stirring for an additional 12 h and then partitioned between EtOAc and saturated aqueous NaHCO$_3$ solution. The organic layer was washed with saturated brine, dried over MgSO$_4$ and evaporated. The residue was triturated with Et$_2$O and the product obtained by filtration as a beige solid. (UPLC-MS 7) $t_R$ 1.09; ESI-MS 298.2 [M+H]$^+$.

Intermediate 97: 6-amino-4-isopropoxynicotinonitrile

A solution of KHMDS (87 g, 438 mmol) was added portionwise to a solution of propan-2-ol (26.3 g, 438 mmol) in THF (250 ml) at room temperature. After 15 min a solution of 6-amino-4-fluoronicotinonitrile (intermediate 21, 30 g, 219 mmol) in THF (200 ml) was added and the reaction mixture stirred for 18 h at room temperature. The reaction mixture was partitioned between saturated aqueous NH$_4$Cl and EtOAc, extracted with EtOAc (2×), the combined EtOAc layers were dried over Na$_2$SO$_4$ and evaporated. The residue was triturated with Et$_2$O and the product obtained by filtration as a yellow solid. $^1$H NMR (400 MHz, DMSO-$d_6$) δ 8.12 (s, 1H), 6.82 (s, 2H), 6.07 (s, 1H), 4.64 (septet, 1H), 1.31 (d, 6H). (UPLC-MS 7) $t_R$ 0.61; ESI-MS 178.1 [M+H]$^+$.

Intermediate 81: 1-((2-(dimethoxymethyl)-5,6,7,8-tetrahydro-1,8-naphthyridin-3-yl)methyl)-4-methyl-piperazin-2-one Sodium triacetoxyborohydride (3.10 g, 14.61 mmol) was added to a mixture of 2-(dimethoxymethyl)-5,6,7,8-tetrahydro-1,8-naphthyridine-3-carbaldehyde (intermediate 41, 2.30 g, 9.74 mmol), ethyl 2-((2-aminoethyl)(methyl)amino) acetate dihydrochloride (intermediate 82, 2.6 g, 14.61 mmol) and triethylamine (6.75 ml, 48.7 mmol) in 1,2-dichloroethane (20 ml) at room temperature. The reaction mixture was stirred for 21 h at room temperature and additional sodium triacetoxyborohydride (2.6 g, 9.74 mmol) was added. After a further 4 h stirring at room temperature, again additional sodium triacetoxyborohydride (1.3 g, 4.87 mmol) was added and the reaction maintained at 4° C. for 2.5 days. The reaction mixture was then warmed to room temperature, saturated aqueous NaHCO$_3$ solution added, the mixture extracted with DCM (3×), the combined organic layers dried over Na$_2$SO$_4$ and evaporated. The residue was applied to a 120 g RediSep® silica column as a DCM solution and purified by normal phase chromatography, eluting with a gradient from DCM to 10% MeOH in DCM. Product containing fractions were combined and evaporated to give the title compound as an orange foam. $^1$H NMR (400 MHz, CDCl$_3$) δ 7.08 (s, 1H), 5.30 (s, br, 1H), 5.20 (s, 1H), 4.69 (s, 2H), 3.44-3.34 (m, 2H), 3.40 (s, 6H), 3.22-3.15 (m, 2H), 3.24 (s, 2H), 2.71-2.64 (m, 2H), 2.58-2.50 (m, 2H), 2.31 (s, 3H), 1.98-1.82 (m, 2H).

(UPLC-MS 6) $t_R$ 0.33; ESI-MS 335.3 [M+H]$^+$.

Intermediate 82: ethyl 2-((2-aminoethyl)(methyl)amino)acetate dihydrochloride Concentrated hydrochloric acid (10 ml) was added to a solution of ethyl 2-((2-((tert-butoxycarbonyl)amino)ethyl)(methyl)amino)acetate (intermediate 83, 3.05 g, 11.13 mmol) in THF (20 ml) and EtOH (100 ml) at room temperature. After stirring 1 h at room temperature the reaction mixture was evaporated, ethanol (20 ml) added, evaporated, further ethanol (50 ml) added and then stirred at 60° C. for 70 min. The cooled reaction mixture was then evaporated to give the title compound as a pale-yellow glass. $^1$H NMR (400 MHz, DMSO-d$_6$) δ 8.58 (s, br, 3H), 4.19 (q, 2H), 4.26-4.15 (m, 2H), 3.44 (s, br, 2H), 3.21 (s, br, 2H), 2.88 (s, 3H), 1.21 (t, 3H).

Intermediate 83: ethyl 2-((2-((tert-butoxycarbonyl)amino)ethyl)(methyl)amino)acetate Ethyl bromoacetate (1.27 ml, 11.48 mmol) was added to a mixture of tert-butyl (2-(methylamino)ethyl)carbamate (2.0 g, 11.48 mmol), triethylamine (4.81 ml) and THF (24 ml) at 0° C. After stirring 24 h at room temperature the reaction mixture was partitioned between saturated aqueous NaHCO$_3$ and DCM, extracted 2× with DCM, the organic layers dried over Na$_2$SO$_4$ and evaporated to give the title compound as a clear pale-yellow oil. $^1$H NMR (400 MHz, CDCl$_3$) δ 5.20 (s, br, 1H), 4.18 (q, 2H), 3.24 (s, 2H), 3.22-3.16 (m, 2H), 2.65-2.61 (m, 2H), 2.38 (s, 3H), 1.42 (s, 9H), 1.24 (t, 3H).

Example 101: N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide

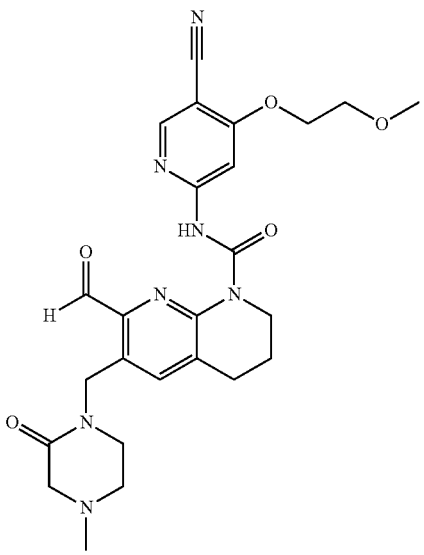 [SMILES: COCCOc1cc(NC(=O)N2CCCc3cc(CN4CCN(C)CC4=O)c(C=O)nc32)ncc1C#N]

Hydrochloric acid (4M, 8.6 ml) was added to a solution of N-(5-cyano-4-(2-methoxyethoxy)pyridin-2-yl)-7-(dimethoxymethyl)-6-((4-methyl-2-oxopiperazin-1-yl)methyl)-3,4-dihydro-1,8-naphthyridine-1(2H)-carboxamide (intermediate 107, 950 mg, 1.72 mmol) in THF (15 ml) at room temperature. After stirring for 4 h at room temperature saturated aqueous NaHCO$_3$ was added, the mixture extracted with DCM (3×), the organic layers dried over MgSO$_4$ and evaporated. The residue was stirred with EtOAc for 20 minutes then diluted with heptane and then filtered to give the title compound as a white solid.
$^1$H NMR (400 MHz, DMSO-d$_6$) δ 13.83 (s, 1H), 10.11 (s, 1H), 8.60 (s, 1H), 7.94 (s, 1H), 7.56 (s, 1H), 4.90 (s, 2H), 4.38-4.32 (m, 2H), 4.01-3.95 (m, 2H), 3.79-3.73 (m, 2H), 3.35 (s, 3H), 3.29-3.23 (m, 2H), 3.06 (s, 2H), 2.97-2.91 (m, 2H), 2.65-2.59 (m, 2H), 2.24 (s, 3H), 1.98-1.92 (m, 2H).
(UPLC-MS 6) t$_R$ 0.81 min, ESI-MS 508.2, [M+H]$^+$.

The following salts were prepared from the above free base form of N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide by precipitation with the appropriate counterions.

Malate with 1:1 stoichiometry (mw 641.63): A solution of L-malic acid (39.6 mg, 0.296 mmol) in acetone (3 ml) was added dropwise to a solution of N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide (150 mg, 0.296 mmol) in acetone (2 ml) at room temperature and the mixture then heated at reflux for 30 minutes. The cooled mixture was left open to the atmosphere until the volume reduced to 3 ml then sealed and stood 18 h at 4° C. The solid was then collected by filtration, washing with Et$_2$O, and dried for 18 h at 40° C. under vacuum to give the title salt as a beige solid.
$^1$H NMR (400 MHz, DMSO-d$_6$) δ 13.78 (s, 1H), 10.06 (s, 1H), 8.58 (s, 1H), 7.89 (s, 1H), 7.54 (s, 1H), 4.84 (s, 2H), 4.33-4.26 (m, 2H), 4.20 (t, 1H). 3.98-3.92 (m, 2H), 3.75-3.66 (m, 2H), 3.31 (s, 3H), 3.26-3.22 (m, 2H), 3.08 (s, 2H), 2.92-2.85 (m, 2H), 2.63-2.51 (m, 3H), 2.42-2.36 (m, 1H), 2.21 (s, 3H), 2.03 (s, 1H), 1.96-1.88 (m, 2H).

Tosylate with 1:1 stoichiometry (mw 679.75): A solution of para-toluene sulphonic acid (49.1 mg, 0.258 mmol) in acetone (3 ml) was added dropwise to a solution of N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide (131 mg, 0.258 mmol) in dichloromethane (5 ml) at to room temperature. After the addition was complete additional dichloromethane (3 ml) was added and the mixture stirred for 5 h at room temperature. The white solid was then collected by filtration, washing with acetone, and dried for 18 h at 40° C. under vacuum to give the title salt.
$^1$H NMR (400 MHz, DMSO-d$_6$) 13.78 (s, 1H), 10.06 (s, 1H), 8.57 (s, 1H), 7.91 (s, 1H), 7.54 (s, 1H), 7.45 (d, 2H), 7.07 (d, 2H), 4.92 (s, 2H), 4.36-4.30 (m, 2H), 4.00-3.95 (m, 3H), 3.76-3.67 (m, 2H), 3.53-3.48 (s, br, 2H), 3.34-3.23 (m, 8H), 2.92-2.85 (m, 4H), 2.23 (s, 3H), 1.97-1.90 (m, 2H).

Tartrate with 1:1 stoichiometry (mw 657.63): A solution of L-(+)-tartaric acid (44 mg, 0.296 mmol) in acetone (5 ml) was added to a suspension of N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide (150 mg, 0.296 mmol) in acetone (5 ml) at room temperature. The mixture was stirred at 50° C. for 30 min, decanted to remove a small amount of insoluble material and cooled slowly to room temperature. The precipitate was collected by filtration and dried under vacuum at 50° C. to give the title compound as a beige solid.
$^1$H NMR (400 MHz, DMSO-d$_6$) δ 13.78 (s, 1H), 10.09 (s, 1H), 8.57 (s, 1H), 7.91 (s, 1H), 7.54 (s, 1H), 4.85 (s, 2H), 4.33-4.26 (m, 2H), 4.25 (s, 2H), 3.98-3.92 (m, 2H), 3.75-3.66 (m, 2H), 3.31 (s, 3H), 3.27-3.23 (m, 2H), 3.08 (s, 2H), 2.92-2.85 (m, 2H), 2.63-2.59 (m, 2H), 2.22 (s, 3H), 1.96-1.88 (m, 2H).

Citrate salt with 1:1 stoichiometry (mw 699.68): A solution of citric acid (0.1 M, 1.97 ml, 0.197 mmol) was added to a suspension of N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide (100 mg, 0.197 mmol) in acetone (5 ml) at room temperature. The mixture was stirred at 55° C. for 3 h, cooled slowly to room temperature, the white precipitate collected by filtration and dried under vacuum to give the title compound.

¹H NMR (600 MHz, DMSO-d₆) δ 13.84 (s, 1H), 10.11 (s, 1H), 8.60 (s, 1H), 7.94 (s, 1H), 7.57 (s, 1H), 4.91 (s, 2H), 4.38-4.32 (m, 2H), 4.02-3.96 (m, 2H), 3.79-3.73 (m, 2H), 3.36 (s, 3H), 3.31-3.25 (m, 2H), 3.14 (s, 2H), 2.98-2.92 (m, 2H), 2.74 (d, 2H), 2.73-2.68 (m, 2H), 2.65 (d, 2H), 2.30 (s, 3H), 1.99-1.93 (m, 2H).

Intermediate 107: N-(5-cyano-4-(2-methoxyethoxy)pyridin-2-yl)-7-(dimethoxymethyl)-6-((4-methyl-2-oxopiperazin-1-yl)methyl)-3,4-dihydro-1,8-naphthyridine-1(2H)-carboxamide A mixture of 1-((2-(dimethoxymethyl)-5,6,7,8-tetrahydro-1,8-naphthyridin-3-yl)methyl)-4-methylpiperazin-2-one (intermediate 81, 1.03 g, 3.08 mmol), phenyl (5-cyano-4-(2-methoxyethoxy)pyridin-2-yl)carbamate (intermediate 108, 2.19 g, 6.16 mmol) and DMAP (753 mg, 6.16 mmol) in DMA (15 ml) was heated at 90° C. for 3.5 h. The cooled reaction mixture was partitioned between EtOAc and, the organic layer dried over MgSO₄ and evaporated. The residue was purified by reversed phase chromatography (RP 4) and the product containing fractions were partitioned between saturated aqueous NaHCO₃ and EtOAc, the organic layer dried over MgSO₄ and vaporated. The residue was then triturated with a mixture of DCM, Et₂O and heptane to give the title compound as a white solid. (UPLC-MS 7) t_R 0.80; ESI-MS 554.4 [M+H]⁺.

Intermediate 108: phenyl (5-cyano-4-(2-methoxyethoxy)pyridin-2-yl)carbamate

Phenyl chloroformate (4.93 ml, 39.3 mmol) was added drop wise to a mixture of 6-amino-4-(2-methoxyethoxy)nicotinonitrile (intermediate 20, 3.45 g, 17.86 mmol) and pyridine (6.35 ml, 79 mmol) in THF (100 ml) at room temperature. The reaction mixture was stirred for 5 h at room temperature and then partitioned between EtOAc and saturated aqueous NaHCO₃ solution, the organic layer washed with saturated brine, dried over MgSO₄ and evaporated. The residue was triturated with EtOAc and the product obtained by filtration as a white solid. (UPLC-MS 7) t_R 0.97; ESI-MS 314.3 [M+H]⁺.

Example 205: (R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide

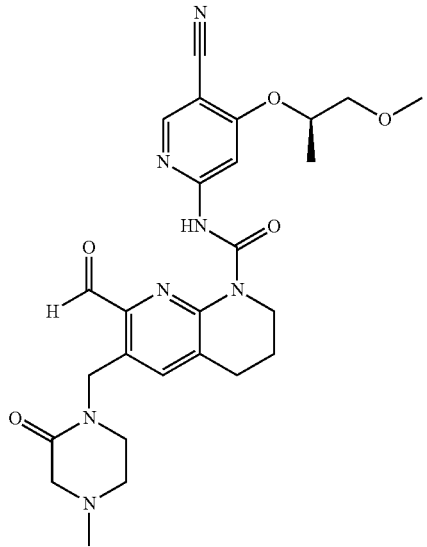 [SMILES: COC[C@@H](C)Oc1cc(NC(=O)N2CCCc3cc(CN4CCN(C)CC4=O)c(C=O)nc32)ncc1C#N]

From intermediates 145 and 81, coupled in an analogous manner to intermediate 236, but using DMF instead of THF, and deprotected in an analogous manner to Example 201. The title compound was obtained as an off-white solid.

¹H NMR (400 MHz, DMSO-d₆) δ 13.84 (s, 1H), 10.12 (s, 1H), 8.61 (s, 1H), 8.00 (s, 1H), 7.57 (s, 1H), 4.91 (s, 2H), 4.87 (m, 1H), 4.00 (m, 2H), 3.59 (m, 2H), 3.33 (s, 3H), 3.29 (m, 2H), 3.07 (s, 2H), 2.95 (m, 2H), 2.63 (m, 2H), 2.25 (s, 3H), 1.95 (m, 2H), 1.34 (d, 3H).

(UPLC-MS 6) t_R 0.82 min, ESI-MS 522.2 [M+H]⁺.

The following salts were prepared from the above free base form of (R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide by precipitation with the appropriate counterions.

Tartrate with 1:1 stoichiometry (mw 671.66): A solution of L-(+)-tartaric acid in acetone (0.1 M, 2.0 ml, 0.200 mmol) was added to a suspension of (R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide (103 mg, 0.197 mmol) in acetone (4 ml) at room temperature. The mixture was warmed to 55° C., maintained at this temperature for 2.5 h with sonication and then cooled slowly to 5° C. The precipitate that formed was collected by filtration and dried under vacuum at 40° C. to give the title compound.

¹H NMR (600 MHz, DMSO-d₆) δ 13.83 (s, 1H), 10.11 (s, 1H), 8.60 (s, 1H), 7.99 (s, 1H), 7.57 (s, 1H), 4.91 (s, 2H), 4.87 (m, 1H), 4.46 (s, 2H), 4.00 (m, 2H), 3.59 (m, 2H), 3.33 (s, 3H), 3.29 (m, 2H), 3.09 (s, 2H), 2.95 (m, 2H), 2.66 (m, 2H), 2.26 (s, 3H), 1.95 (m, 2H), 1.34 (d, 3H).

Tosylate with 1:1 stoichiometry (mw 693.78): A solution of tosic acid in acetone (0.1 M, 2.0 ml, 0.200 mmol) was added to a suspension of (R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide (100 mg, 0.192 mmol) in acetone (4 ml) at room temperature. The mixture was warmed to 55° C., maintained at this temperature for 2.5 h with sonication and then cooled slowly to room temperature. After standing 18 h at 5° C. n-hexane (6 ml) was added, the solid collected by filtration and then dried under vacuum to give the title compound.

¹H NMR (600 MHz, DMSO-d₆) δ 13.80 (s, 1H), 10.09 (s, 1H), 8.59 (s, 1H), 7.98 (s, 1H), 7.68 (s, 1H), 7.41 (d, 2H), 7.07 (d, 2H), 4.96 (s, 2H), 4.86 (m, 1H), 4.00 (m, 2H), 3.58 (m, 2H), 3.53 (m, 2H), 3.36 (br, m, 5H), 3.32 (s, 3H), 2.94 (s, 2H), 2.90 (m, 2H), 2.28 (s, 3H), 1.95 (m, 2H), 1.34 (d, 3H).

Citrate with 1:1 stoichiometry (mw 713.71): A solution of citric acid in acetone (0.1 M, 2.0 ml, 0.200 mmol) was added to a suspension of (R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide (100 mg, 0.192 mmol) in acetone (4 ml) at room temperature. The mixture was warmed to 55° C., maintained at this temperature for 2.5 h with sonication and then cooled slowly to room temperature. After standing 18 h at 5° C. the solid was collected by filtration, washed with acetone and then dried under vacuum to give the title compound.

¹H NMR (600 MHz, DMSO-d₆) δ 13.81 (s, 1H), 10.10 (s, 1H), 8.59 (s, 1H), 7.98 (s, 1H), 7.56 (s, 1H), 4.90 (s, 2H), 4.85 (m, 1H), 3.98 (m, 2H), 3.58 (m, 2H), 3.32 (s, 3H), 3.30 (m, 2H), 3.13 (s, 2H), 2.94 (m, 2H), 2.73 (d, 2H), 2.70 (m, 2H), 2.64 (d, 2H), 2.29 (s, 3H), 1.95 (m, 2H), 1.34 (d, 3H).

Malate with 1:1 stoichiometry (mw 655.58): A solution of L-malic acid in acetone (0.1 M, 2.0 ml, 0.200 mmol) was added to a suspension of (R)—N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide (100 mg, 0.192 mmol) in acetone (4 ml) at room temperature. The mixture was warmed to 55° C., maintained at this temperature for 2.25 h with sonication and then cooled to room temperature. n-Hexane (6 ml) was added, the solid was collected by filtration and then dried under vacuum to give the title compound.

$^1$H NMR (600 MHz, DMSO-$d_6$) δ 13.84 (s, 1H), 10.11 (s, 1H), 8.60 (s, 1H), 7.99 (s, 1H), 7.56 (s, 1H), 4.91 (s, 2H), 4.87 (m, 1H), 4.22 (m, 1H), 3.99 (m, 2H), 3.59 (m, 2H), 3.33 (s, 3H), 3.29 (m, 2H), 3.09 (s, 2H), 2.95 (m, 2H), 2.66 (m, 2H), 2.61 (m, 1H), 2.44 (m, 1H), 2.26 (s, 3H), 1.95 (m, 2H), 1.34 (d, 3H).

Intermediate 145: (R)-phenyl (5-cyano-4-((1-methoxypropan-2-yl)oxy)pyridin-2-yl)carbamate Phenyl chloroformate (1.53 ml, 12.2 mmol) was added drop wise to a mixture of (R)-6-amino-4-((1-methoxypropan-2-yl)oxy)nicotinonitrile (intermediate 146, 1.37 g, 5.55 mmol) and pyridine (0.99 ml, 12.2 mmol) in THF (60 ml) at 0° C. The reaction mixture was stirred for 12 h at room temperature and additional pyridine (0.98 ml, 12.2 mmol) and phenyl chloroformate (1.53 ml, 12.2 mmol) were added. After stirring for a further 36 h at room temperature the reaction mixture was partitioned between EtOAc and saturated aqueous NaHCO$_3$ solution, the organic layer washed with saturated brine, dried over MgSO$_4$ and evaporated. The residue was triturated with Et$_2$O and the product obtained by filtration as a white solid. (UPLC-MS 6) $t_R$ 1.04; ESI-MS 328.4 [M+H]$^+$.

Intermediate 146: (R)-6-amino-4-((1-methoxypropan-2-yl)oxy)nicotinonitrile

A solution of KHMDS in THF (1M, 43.8 ml, 43.8 mmol) was added to a solution of (R)-1-methoxypropanol (4.3 ml, 43.8 mmol) in THF (50 ml) at room temperature under a positive argon pressure. After stirring for 15 minutes at room temperature a solution of 6-amino-4-fluoronicotinonitrile (intermediate 21, 3.0 g, 21.88 mmol) in THF (30 ml) was added drop wise. The reaction mixture was stirred for 65 h at room temperature, partitioned between aqueous NH$_4$Cl and EtOAc, extracted 2× with EtOAc, dried over Na$_2$SO$_4$ and evaporated. The residue was triturated with Et$_2$O to give the title compound as a beige solid. $^1$H NMR (400 MHz, DMSO-$d_6$) δ 8.14 (s, 1H), 6.82 (s, br, 2H), 6.09 (s, 1H), 4.64-4.56 (m, 1H), 3.19 (s, 3H), 3.48 (d, 2H), 1.24 (d, 3H).

Reference Intermediate 236: N-(5-cyanopyridin-2-yl)-2-(dimethoxymethyl)-7,8-dihydro-5H-pyrido[2,3-b]azepine-9(6H)-carboxamide A mixture of 2-(dimethoxymethyl)-6,7,8,9-tetrahydro-5H-pyrido[2,3-b]azepine (intermediate 237, 35 mg, 0.154 mmol), phenyl (5-cyanopyridin-2-yl)carbamate (intermediate 240, 122 mg, 0.509 mmol) and DMAP (28.3 mg, 0.231 mmol) in THF (1.7 ml) was heated at reflux for 23 h. The reaction mixture was diluted with sat. aq. NaHCO$_3$ and extracted with DCM (3×). The combined organic layers were dried over Na$_2$SO$_4$ and evaporated. The crude material was applied to a 40 g RediSep® silica column and purified by normal phase chromatography, eluting with 99:1 DCM/MeOH. Product-containing fractions were combined and evaporated. The residue was triturated with Et$_2$O and the solid removed by filtration. The filtrate was concentrated and the residue triturated with MeOH to give the title compound as a white solid. (UPLC-MS 6) $t_R$ 1.06; ESI-MS 368.1 [M+H]$^+$.

Reference Intermediate 237: 2-(dimethoxymethyl)-6,7,8,9-tetrahydro-5H-pyrido[2,3-b]azepine A microwave vial was charged with a mixture of tert-butyl 2-formyl-7,8-dihydro-5H-pyrido[2,3-b]azepine-9(6H)-carboxylate (intermediate 238, 415 mg, 1.277 mmol) and p-toluenesulfonic acid monohydrate (110 mg, 0.573 mmol) in MeOH (64 ml), sealed and then heated at 135° C. for 3.5 h. The reaction mixture was concentrated and the residue partitioned between sat. aq. NaHCO$_3$ and EtOAc. The aq. phase was extracted with EtOAc (2×)—the combined organic layers were dried over Na$_2$SO$_4$ and evaporated. The crude material was applied to a 120 g RediSep® silica column and purified by normal phase chromatography, eluting with EtOAc. Product-containing fractions were combined and evaporated to give the title compound as a light yellow oil. (UPLC-MS 6) $t_R$ 0.60; ESI-MS 223.1 [M+H]$^+$.

Reference Intermediate 238: tert-butyl 2-formyl-7,8-dihydro-5H-pyrido[2,3-b]azepine-9(6H)-carboxylate Ozone was bubbled through a mixture of tert-butyl 2-vinyl-7,8-dihydro-5H-pyrido[2,3-b]azepine-9(6H)-carboxylate (intermediate 239, 470 mg, 1.66 mmol) in DCM (6.5 ml) at −78° C. After 15 minutes, the intermediate ozonide was treated with dimethyl sulfide (0.86 ml, 11.62 mmol) and then the reaction mixture was slowly warmed to room temperature. After 1.5 h, the mixture was diluted with H$_2$O and extracted with DCM (3×). The combined organic layers were washed with sat. aq. NaHCO$_3$ and brine, dried over Na$_2$SO$_4$ and evaporated to give the crude title compound as a light brown solid. (UPLC-MS 6) $t_R$ 1.04; ESI-MS 277.1 [M+H]$^+$.

Reference Intermediate 239: tert-butyl 2-vinyl-7,8-dihydro-5H-pyrido[2,3-b]azepine-9(6H)-carboxylate A degassed mixture of tert-butyl 2-chloro-7,8-dihydro-5H-pyrido[2,3-b]azepine-9(6H)-carboxylate (690 mg, 2.44 mmol), potassium trifluoro(vinyl)borate (344 mg, 2.44 mmol), PdCl$_2$(dppf).CH$_2$Cl$_2$ (199 mg, 0.244 mmol) and Cs$_2$CO$_3$ (2.00 g, 6.1 mmol) in THF (50 ml) and H$_2$O (10 ml) was heated at 80° C. for 3.5 h. The reaction mixture was diluted with H$_2$O and extracted with DCM (2×). The combined organic layers were dried over Na$_2$SO$_4$ and evaporated. The crude material was applied to a 120 g RediSep® silica column and purified by normal phase chromatography, eluting with 1:3 EtOAc/heptanes. Product-containing fractions were combined and evaporated to give the title compound as an off-white solid. (UPLC-MS 6) $t_R$ 1.18; ESI-MS 275.2 [M+H]$^+$.

Reference Intermediate 240: phenyl (5-cyanopyridin-2-yl)carbamate

From 2-amino-5-cyanopyridine, reacted in an analogous manner to the preparation of intermediate 108. (UPLC-MS 6) $t_R$ 0.92; ESI-MS 240.1 [M+H]$^+$.

Reference Example 201: N-(5-cyanopyridin-2-yl)-2-formyl-7,8-dihydro-5H-pyrido[2,3-b]azepine-9(6H)-carboxamide

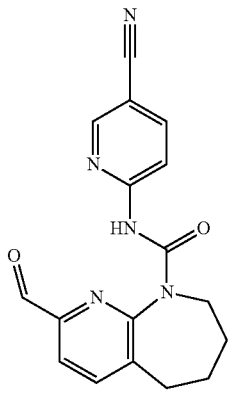 [SMILES: N#Cc1ccc(NC(=O)N2CCCCc3ccc(C=O)nc32)nc1]

Concentrated hydrochloric acid (0.65 ml) was added to a solution of N-(5-cyanopyridin-2-yl)-2-(dimethoxymethyl)-7,8-dihydro-5H-pyrido[2,3-b]azepine-9(6H)-carboxamide (reference intermediate 236, 29 mg, 0.079 mmol) in THF (0.9 ml) at room temperature. After stirring for 1 h at room temperature sat. aq. NaHCO$_3$ was added and the mixture extracted with DCM (3×). The combined organic layers were washed with brine, dried over Na$_2$SO$_4$ and evaporated. The residue was triturated with Et$_2$O to give the title compound as a white solid.

$^1$H NMR (400 MHz, DMSO-d$_6$) δ 10.00 (br s, 1H), 9.88 (s, 1H), 8.67 (m, 1H), 8.20 (m, 1H), 8.11 (d, 1H), 8.04 (d, 1H), 7.84 (s, 1H), 3.73 (m, 2H), 2.91 (m, 2H), 1.82 (m, 2H), 1.72 (m, 2H). (UPLC-MS 6) t$_R$ 0.93 min, ESI-MS 322.1 [M+H]$^+$.

Cell Proliferation Assay

Methylene Blue Staining Proliferation Assay (MBS):

The effect of compounds on cell proliferation is assessed using HuH-7 hepatocellular carcinoma cells obtained from the Japanese Collection of Research Bioresources Cell Bank (Cat# JCRB0403) and cultured in the vendor-recommended medium (DMEM high glucose (Amimed Cat#1-26F01-1), 10% foetal calf serum (Invitrogen Cat#16140-071), 1 mM sodium pyruvate (Amimed Cat#5-60F00-H), 1× Penicillin/Streptomycin (Amimed Cat#4-01F00-H)) at 37° C. in a humidified 5% CO$_2$ incubator. Specifically, 5000 cells/well were seeded in 96-well tissue culture plates (TPP Cat#92696) in a total media volume of 100 µl/well and increasing compound dilutions or DMSO were added 24 hours thereafter in triplicates. 72 hours after compound addition, cells were fixed by adding 25 µL/well of 20% glutaraldehyde (Sigma Aldrich Cat# G400-4) and incubated for 10 minutes at room temperature. Cells were washed three times with H$_2$O, 200 µL/well and stained with 100 µL/well 0.05% methylene blue (ABCR GmbH Cat# AB117904) for 10 minutes at room temperature. Cells were washed 3 times with H2O, 200 µL/well and then lysed by adding 200 µL/well of 3% HCl (Fluka Cat#84422) for 30 minutes at room temperature with shaking. Optical density was measured at A650 nm. The concentration of compound providing 50% of proliferation inhibition with respect to DMSO-treated cells was determined (IC$_{50}$) using XLFit software.

The effect of compounds on cell proliferation using Hep 3B2.1-7 hepatocellular carcinoma cells, FU97 gastric cancer cells, JHH7 hepatocellular carcinoma cells or JHH6 hepatocellular carcinoma cells is assessed as above. Hep 3B2.1-7, FU97, JHH7 or JHH6 are obtained from the Japanese Collection of Research Bioresources Cell Bank. Hep 3B2.1-7 cells are cultured in EMEM+10% FCS+1 mM Na pyruvate+2 mM L-glutamine and 2000 cells/well are seeded for the proliferation assay. FU97 cells are cultured in DMEM high glucose+10% FCS+1 mM Na pyruvate+4 mM L-glutamine+1×ITS and 2000 cells/well are seeded for the proliferation assay. JHH6 and JHH7 cells are cultured in William's E+10% FCS+2 mM L-glutamine and 3000 cells are seeded for the proliferation assay.

CellTiter Glo (CTG) Assay:

The functional effect of compounds on cell proliferation is assessed using HuH-7 hepatocellular carcinoma cells obtained from the Japanese Collection of Research Bioresources Cell Bank (Cat# JCRB0403) and cultured in the vendor-recommended medium (DMEM high glucose (Amimed Cat#1-26F01-1), 10% foetal calf serum (Invitrogen Cat#16140-071), 1 mM sodium pyruvate (Amimed Cat#5-60F00-H), 1× Penicillin/Streptomycin (Amimed Cat#4-01F00-H)) at 37° C. in a humidified 5% CO$_2$ incubator. Compound-mediated suppression of cell proliferation/viability is assessed by quantification of cellular ATP levels using the CellTiter-Glo (CTG) reagent (Promega, Cat# G7573). Briefly, cells are seeded at 3,000 cells/well/80 µl fresh medium into tissue-culture-treated 96-well plates (Costar Cat#3904), followed by addition of 20 µl medium containing compound dilutions at 5-fold their final intended concentration. Dose-response effects are assessed by 3-fold serial dilutions of the test compound, starting at 10 µM. Following incubation of the cells for 3 days at 37° C. and 5% CO$_2$, the effect of inhibitors on cell viability is quantified following addition of 50 µl CTG and luminescence measurement (integration time: 500 ms) as per vendor manual, using a correspondingly equipped multi-mode plate reader (M200Pro, TECAN, Switzerland). For data analysis, the assay background value determined in wells containing medium, but no cells, is subtracted from all data points. To enable differentiation of cytotoxic from cytostatic compounds, the number of viable cells is assessed relative to that observed at the time of compound addition using a separate cell plate (day 0). The effect of a particular test compound concentration on cell proliferation/viability is expressed as percentage of the background- and day 0-corrected luminescence reading obtained for cells treated with vehicle only (DMSO, 0.1% f.c.), which is set as 100%, whereas the luminescence reading for wells containing medium only, but no cells, is set as −100%. Compound concentrations leading to half-maximal growth inhibition (GI50) are determined using standard four parameter curve fitting (XLfit 5.2, IDBS, UK).

| Example | HUH7 proliferation (nM) | | Hep3B proliferation (nM) | JHH7 proliferation (nM) | FU97 proliferation (nM) |
| --- | --- | --- | --- | --- | --- |
| | MBS | CTG | MBS | MBS | MBS |
| 3 | >3000 | >3000 | nd | nd | nd |
| 27 | >3000 | n.d. | 719 | >3,000 | nd |
| 39 | 123 | 569 | >3,000 | >3,000 | nd |
| 49 | n.d. | 463 | nd | nd | nd |
| 50 | 270.3 | 436 | 453 | 484 | 234 |
| 63 | 106 | n.d. | >3,000 | >3,000 | nd |
| 68 | 1092 | n.d. | >3,000 | >3,000 | nd |
| 80 | 72 | 168 | 73 | 150 | 96 |
| 83 | 12 | 60.9 | 1 | 9 | 23 |
| 92 | n.d. | 38 | nd | nd | nd |

| | HUH7 proliferation (nM) | | Hep3B proliferation (nM) | JHH7 proliferation (nM) | FU97 proliferation (nM) |
|---|---|---|---|---|---|
| Example | MBS | CTG | MBS | MBS | MBS |
| 101 | 82 | 142 | 21 | nd | nd |
| 205 | 14.0 | 17.8 | 5 | nd | nd |

In order to confirm their efficacy, the compounds can be tested in the following in vivo assay.

In Vivo Assay

Subcutaneous tumors in nude mice were induced by injecting a total of $5 \times 10^6$ cells in 100 µl HBSS containing 50% Matrigel in the flank of nude mice. Treatment with compounds starts approximately 3 weeks post cell injection with an average tumor size of around 150-200 mm³. Animals are randomized into groups of n=6 for vehicle control and each tested dose of the compound. Animals were treated for at least 14 days to assess anti-tumor effect and tolerability. Measurement of tumor size was performed with a caliper 2 times per week. Tumor volume (TVol) was calculated in mm³ using the formula (Length×Width)×π/6. Tumor response was quantified by calculating the change in tumor volume (endpoint minus starting value) as the T/C, i.e. (ΔTVoldrug/ΔTVolvehicle×100). In the case of tumor regression, the tumor response was quantified by the percentage of regression of the starting tumor volume, i.e. (ΔTVoldrug/ΔTVolday0×100). Statistical analysis was performed by comparing the treatment groups to the vehicle control group at endpoint using Kruskal-Wallis followed by Dunn's post hoc test. At least one compound of the invention showed 70% tumour regression.

Assay for Biomarkers (FGFR4, FGF19 and KLB)

FGF19 protein levels are measured using the human FGF-19 DuoSet DY969 from R&D Systems following the indications of the manufacturer.

Briefly, the capture antibody was diluted in PBS to a working dilution of 4 µg/mL and used to coat a 96-well plate (Costar #2592) with 100 µl/well at room temperature overnight. Plates were washed 6 times with 400 µl/well of PBS/0.05% Tween20 and blocked by adding 300 µl/well of assay diluent (1% BSA in PBS) for 2 hours at room temperature. Plates were washed 6 times with 400 µl/well of PBS/0.05% Tween20.

Cell lines were lysed using MPER lysis buffer (Pierce #78501) supplemented with Complete protease inhibitor tablets (Roche #11836145001) and PhosStop phosphatase inhibitor tablets (Roche #04906837001) on ice for 30 minutes. Lysates were clarified by centrifugation at 12000×g for 15 minutes and protein concentration was determined using the DC protein assay reagents (Bio Rad #500-0116) and a BSA standard. Cell lysates were diluted in PBS/1% BSA to add 100 µg/well and 10 µg/well in 100 µL. A 7-points standard ranging from 1000 pg/mL to 15.625 pg/mL was prepared. Samples and standards were added onto the coated plate, covered with a plate sealer and incubated for 2 hours on a plate mixer followed by 4 washings with 400 µl/well of PBS/0.05% Tween20.

The detection antibody, diluted to a working concentration of 100 ng/mL in PBS/1% BSA, was added in 100 µl/well and incubated at room temperature for 2 hours on a plate mixer followed by 4 washings with 400 µl/well of PBS/0.05% Tween20.

The streptavidin solution diluted in PBS/1% BSA was added onto the plate and incubated at room temperature, protected from light for 20 minutes followed by 3 washing with 400 µl/well of PBS/0.05% Tween20.

100 µl/well of substrate solution were added and incubated at room temperature, protected from light for 20 minutes followed by 50 µl/well of Stop solution.

The optical density of the plate was determined using a microplate reader set at 450 nm.

FGFR4 protein levels are quantified by performing sandwich-type capture ELISA on cell lysate. Cells were lysed as above.

96-well ELISA plates (NUNC #437111) were pre-coated with mouse anti-FGFR4 mAb (R&D Systems #MAB685), 100 µl each diluted 1:100 in PBS without Ca2+/Mg2+. Following incubation for 1 hour at room temperature on an orbital shaker, 150 µl 3% MSD blocker A (MesoScale Discovery #R93BA-4) in TBS complemented with 0.05% Tween-20 (TBST-T) was added for 1 hour at room temperature. The wells were washed with 3 changes of 200 µl TBST-T.

Equal aliquots of the protein lysates were added to two pre-coated 96-well ELISA plates. Additional wells to assess the assay background were incubated with 100 µl lysis buffer/MSD Blocker A 1% (3:1) buffer mix. After an overnight incubation at 4° C., wells were washed with 3 changes of 200 µl TBS-T. ELISA-plates pre-coated with the capture antibody were then incubated for 1.5 hours with 100 µl rabbit anti-FGFR4 mAb (Cell Signaling Technology #8562) diluted 1:1000 in 1% MSD blocking buffer at room temperature on an orbital shaker. Following 3 washes with 200 µl TBS-T, wells were incubated for 1.5 hours with 100 µl of alkaline phosphatase conjugated F(ab')2 fragment of goat anti-rabbit IgG (Invitrogen #F-21456) diluted 1:20,000 in 1% MSD blocking buffer at room temperature on an orbital shaker. After washing with 3 changes of 200 µl TBS-T and a final wash with 200 µl distilled water, wells were incubated with 90 µl of Tropix CDP-Star Ready to use with Emerald II (Applied Biosystems #T2216) for 40 minutes in the dark. Luminescence was recorded on an InfiniteM1000 plate reader (TECAN). Values obtained in the wells containing lysis/BSA-buffer only were averaged and subtracted from the wells containing lysate samples.

KLB protein levels are quantified by western blot. Cells were lysed as above. 50 µg of cell lysates were loaded onto 4-12% gradient NuPAGE Bis-Tris gels (Invitrogen #WG1402BX10) and blotted onto PVDF membranes. Filters were blocked in 5% milk for 1 hour at room temperature. The primary anti-human Klotho-β antibody (R&D Systems #AF5889) was used at 2 µg/mL. Signal detection was done using a secondary anti-goat-HRP antibody (Sigma #A5420). 1-tubulin was used as an internal control, and the detection was performed with anti-β-tubulin antibody (Sigma clone 2.1) followed by a secondary anti-mouse-HRP antibody (Amersham NA931). Membranes were imaged using the Fusion FX7 imaging system, and KLB levels were expressed as % of 1-tubulin levels. The detection was done with super-signal west dura substrate (Thermo Signal, #34076).

| Cell line | FGF19 (pg/mL) | FGFR4 (luminescence units) | KLB (% of β-tubulin) |
|---|---|---|---|
| HUH7 | 1080 | 1305930 | 3.36 |
| Hep3B | 399 | 700932 | 4.13 |
| JHH7 | 4410 | 537741 | 1.12 |

-continued

| Cell line | FGF19 (pg/mL) | FGFR4 (luminescence units) | KLB (% of β-tubulin) |
|---|---|---|---|
| Fu97 | 841 | 1164087 | 6.39 |
| JHH6 | BLQ | 853 | BLQ |

BLQ indicates below limit of detection using the corresponding assay.

Negative Control

The compounds of the invention can be measured in a JHH6 cell proliferation assay (described above). A compound of the invention measured in this assay showed an IC50>10000 nM.

The invention claimed is:

1. A compound which is a citrate salt of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide.

2. A compound which is a citrate salt of N-(5-cyano-4-((2-methoxyethyl)-amino)pyridin-2-yl)-7-formyl-6-((4-methyl-2-oxopiperazin-1-yl)methyl)-3,4-dihydro-1,8-naphthyridine-1(2H)-carboxamide wherein the stoichiometric ratio of citric acid to N-(5-cyano-4-methoxyethyl)-amino)pyridin-2-yl)-7-formyl-6-((4-methyl-2-oxopiperazin-1-yl)methyl)-3,4-dihydro-1,8-naphthyridine-1(2H)-carboxamide is 0.5:1 or 1:1.

3. A pharmaceutical composition comprising a citrate salt of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide; and one or more pharmaceutically acceptable carriers.

4. A pharmaceutical composition comprising a citrate salt of N-(5-cyano-4-((2-methoxyethyl)-amino)pyridin-2-yl)-7-formyl-6-((4-methyl-2-oxopiperazin-1-yl)methyl)-3,4-dihydro-1,8-naphthyridine-1(2H)-carboxamide wherein the stoichiometric ratio of citric acid to N-(5-cyano-4-((2-methoxyethyl)-amino)pyridin-2-yl)-7-formyl-6-((4-methyl-2-oxopiperazin-1-yl)methyl)-3,4-dihydro-1,8-naphthyridine-1(2H)-carboxamide is 0.5:1 or 1:1; and one or more pharmaceutically acceptable carriers.

* * * * *